(12) United States Patent
Lee et al.

(10) Patent No.: US 12,392,776 B2
(45) Date of Patent: Aug. 19, 2025

(54) METHODS AND KITS FOR DETECTING EXOSOMAL PROTEIN

(71) Applicant: City University of Hong Kong, Kowloon (HK)

(72) Inventors: Youngjin Lee, Seoul (KR); Abhimanyu Thakur, West Bengal (IN); Chi-Man Lawrence Wu, Kowloon (HK); Guangyu Qiu, Zurich (CH); Chen Xu, Nantong (CN); Siu-Pang Ng, Kowloon (HK); Tian Yang, New Territories (HK)

(73) Assignee: City University of Hong Kong, Kowloon (HK)

( * ) Notice: Subject to any disclaimer, the term of this patent is extended or adjusted under 35 U.S.C. 154(b) by 0 days.

(21) Appl. No.: 16/889,623

(22) Filed: Jun. 1, 2020

(65) Prior Publication Data

US 2021/0373022 A1    Dec. 2, 2021

(51) Int. Cl.
  *G01N 33/574*    (2006.01)
  *B82Y 5/00*    (2011.01)
  (Continued)

(52) U.S. Cl.
  CPC .......... *G01N 33/57407* (2013.01); *B82Y 5/00* (2013.01); *G01Q 60/24* (2013.01)

(58) Field of Classification Search
  CPC .............. G01N 33/47; G01N 33/57407; G01N 2333/705; G01N 2333/70596;
  (Continued)

(56) References Cited

U.S. PATENT DOCUMENTS 7,897,356 B2 * 3/2011 Klass ................. G01N 33/6848
                                                435/7.1
2014/0148350 A1 * 5/2014 Spetzler ............ G01N 33/6893
                                                436/501

(Continued)

OTHER PUBLICATIONS

Hartjes in Extracellular Vesicle Quantification and Characterization: Common Methods and Emerging Approaches. Bioengineering review. 1-2 (Year: 2019).*

(Continued)

*Primary Examiner* — Rebecca M Fritchman
(74) *Attorney, Agent, or Firm* — Renner, Kenner, Greive, Bobak, Taylor & Weber

(57) ABSTRACT

A method of detecting one or more exosomal protein in a sample includes the steps of: a) introducing the sample on at least a part of a first sensor having a nanostructure thereon, subjecting the first sensor to an optical radiation in a certain spectral range to produce a localized surface plasmon resonance and measuring an induced phase response; and b) introducing the sample on a second sensor having a nanostructure thereon, and obtaining an image via atomic force microscopy analysis with a probe functionalized with an antibody targeting the exosomal protein. A kit for detecting at least one exosomal protein in a sample includes a first sensor having a nanostructure thereon; a second sensor having a nanostructure thereon, and a probe functionalized with an antibody targeting the exosomal protein.

9 Claims, 65 Drawing Sheets
(3 of 65 Drawing Sheet(s) Filed in Color)

(51) Int. Cl.
*G01Q 60/24* (2010.01)
*G01N 33/543* (2006.01)

(58) Field of Classification Search
CPC .. G01N 33/54373; G01Q 60/44; G01Q 60/24; G01Q 60/42; B82Y 5/00
See application file for complete search history.

(56) References Cited

U.S. PATENT DOCUMENTS

2016/0047812 A1* 2/2016 Ohta ............... C07K 16/2803
530/388.22
2017/0191125 A1* 7/2017 Vijayan ............ G01N 21/554

OTHER PUBLICATIONS

Thakur. Direct detection of two different tumor-derived extracellular vesicles by SAM-AuNls LSPR biosensor. Biosensors and bioelectronics. 2017. (Year: 2017).*

* cited by examiner

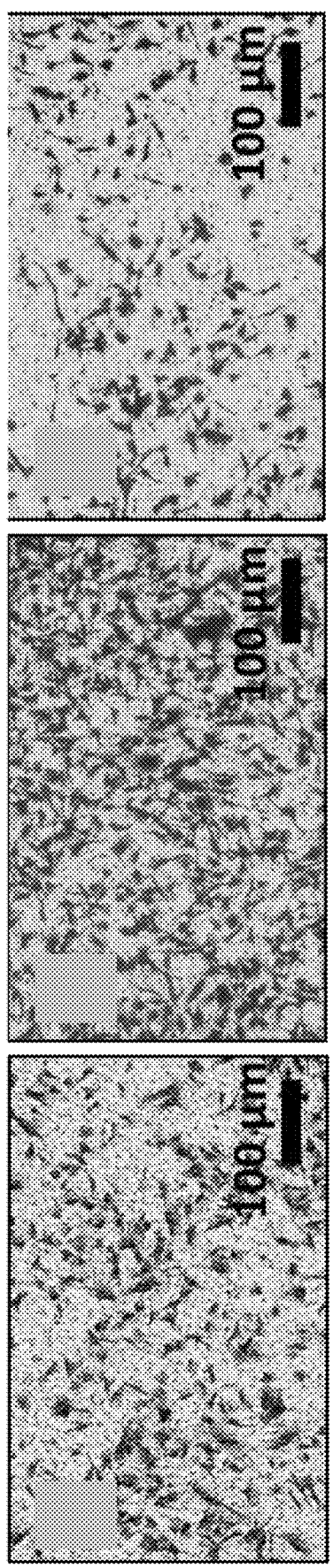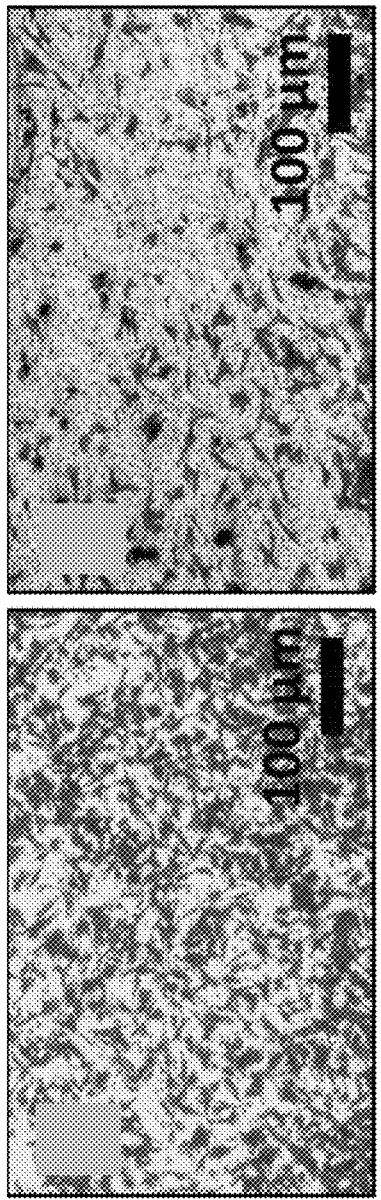
Figure 15A
Figure 15B
Figure 15C
Figure 15D
Figure 15E

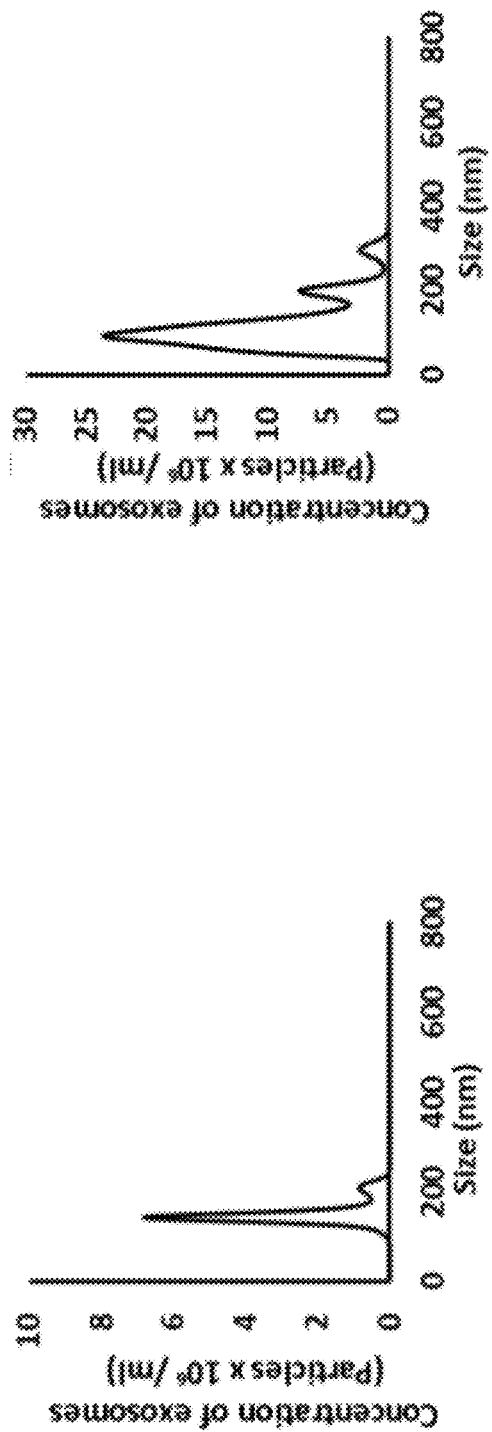
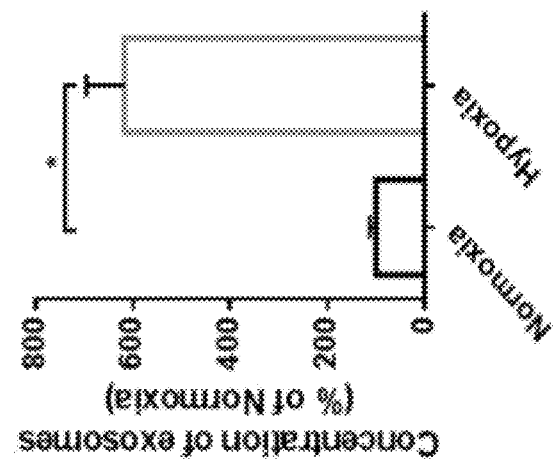
Figure 17A
Figure 17B
Figure 17C

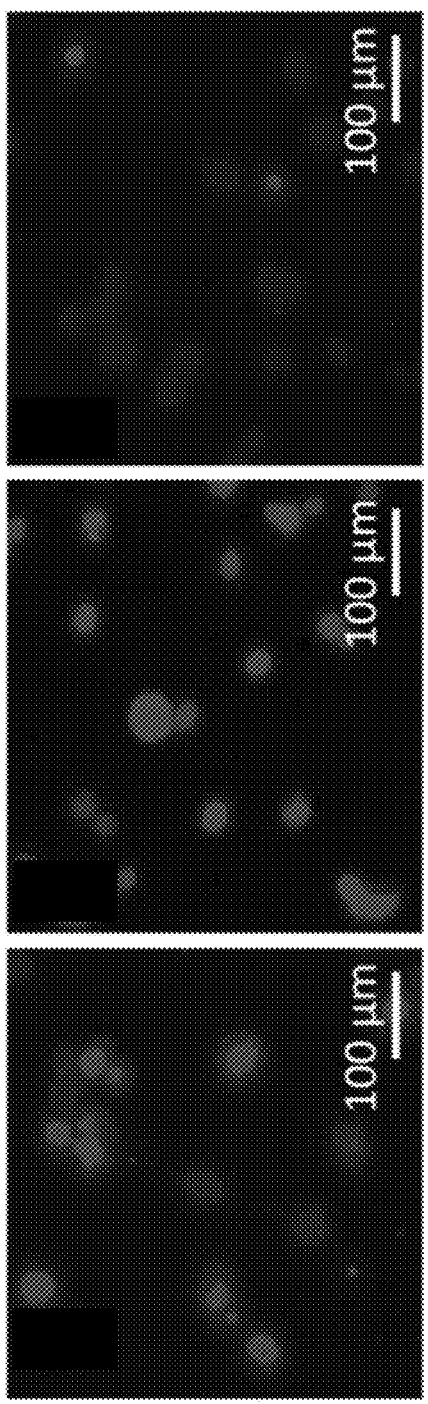
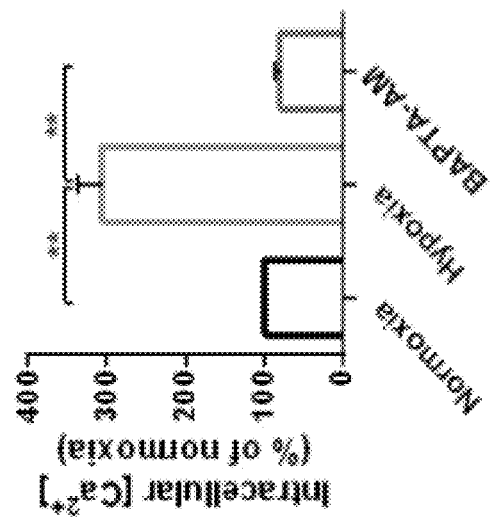
Figure 20A  Figure 20B  Figure 20C  Figure 20D

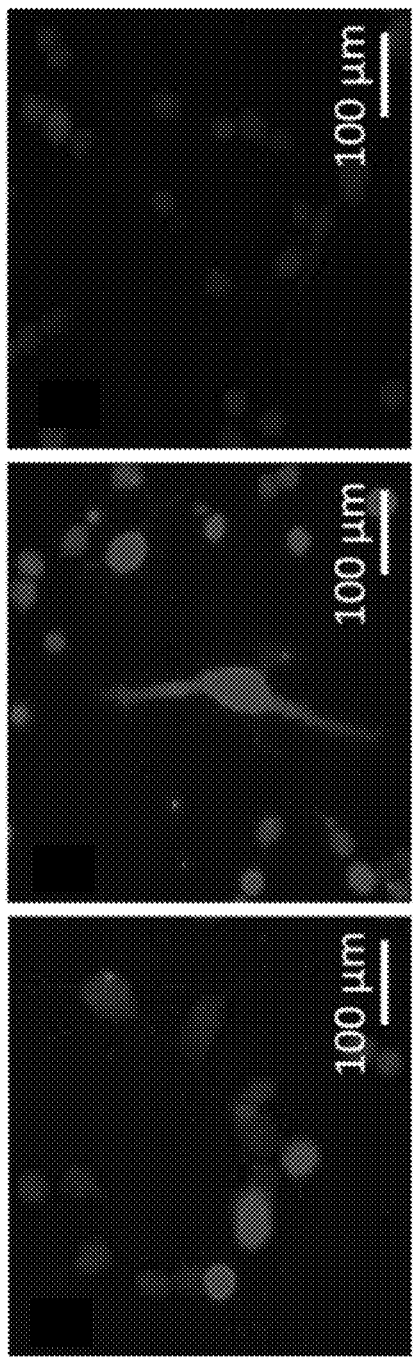
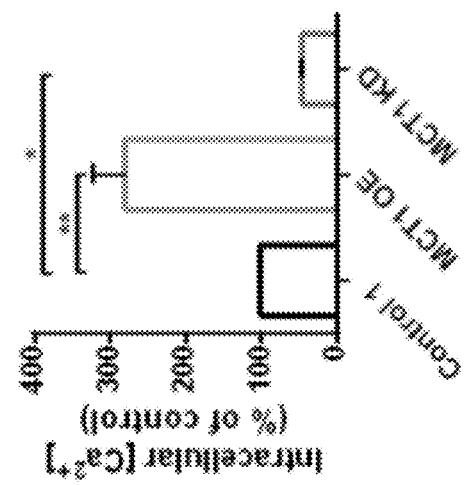
Figure 21A  Figure 21B  Figure 21C  Figure 21D

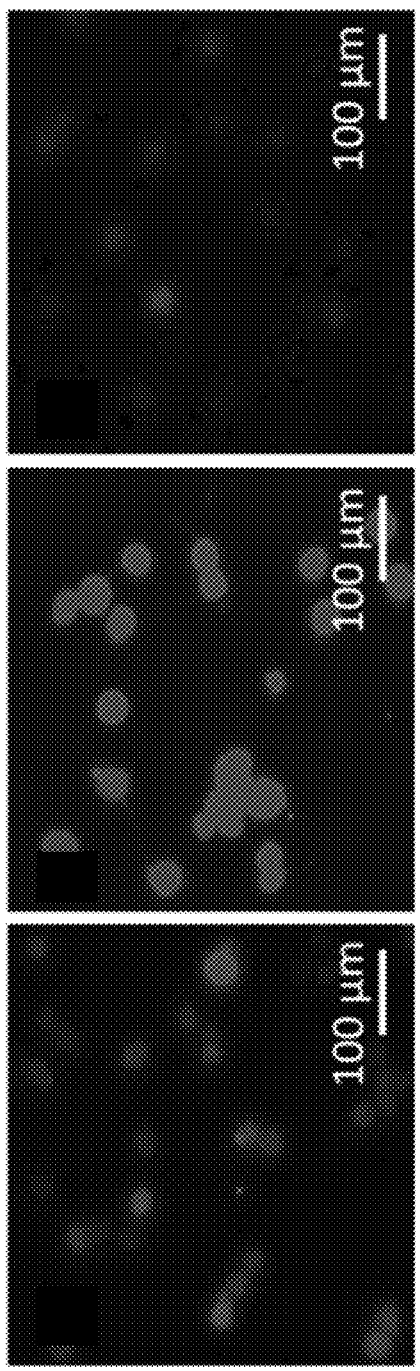
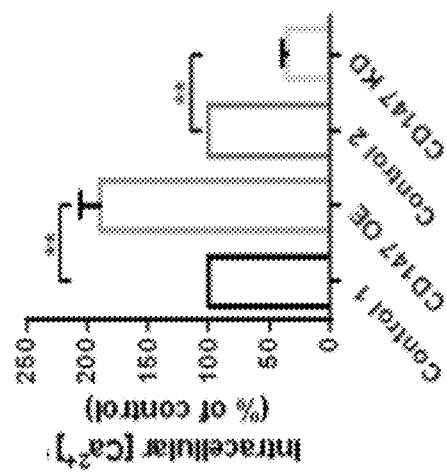
Figure 22A  Figure 22B  Figure 22C  Figure 22D

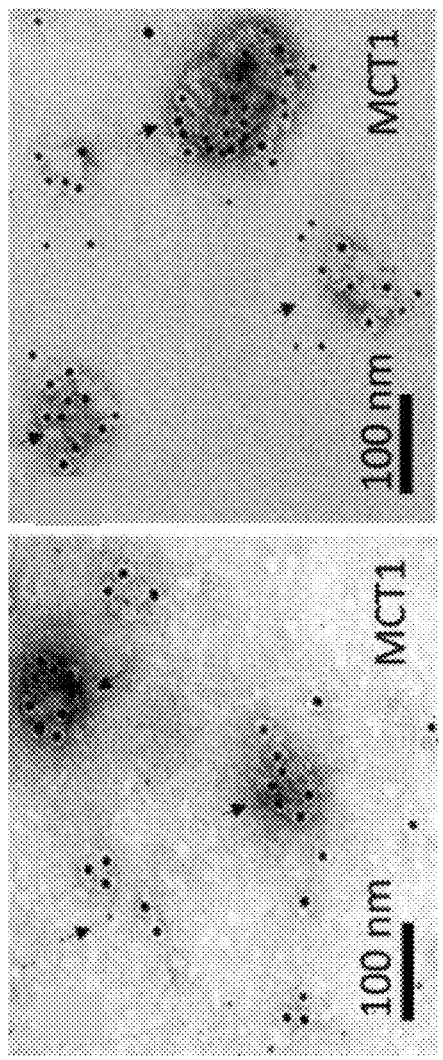
Figure 26A
Figure 26B
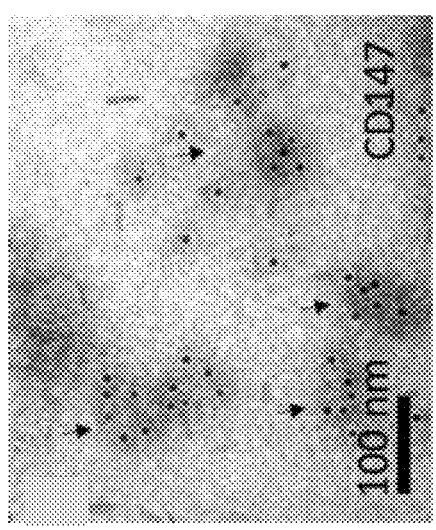
Figure 26D
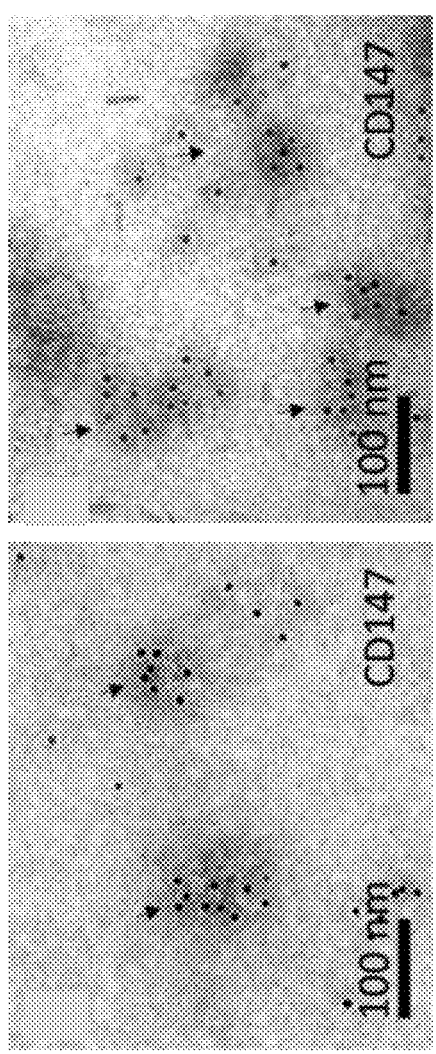
Figure 26C

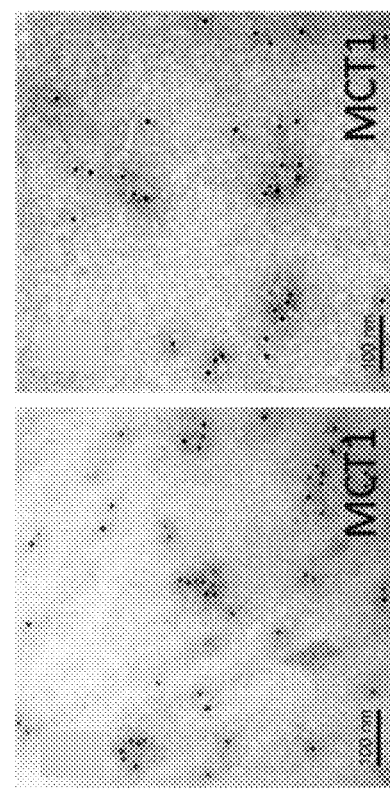
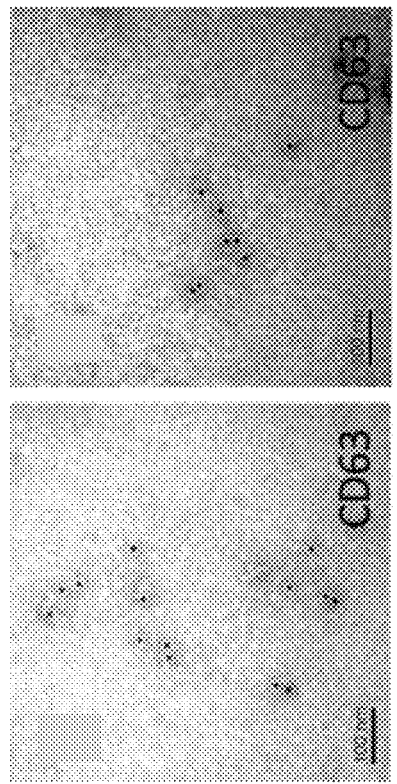
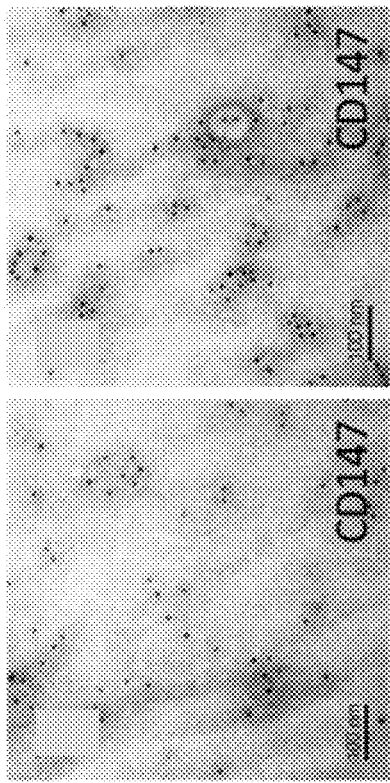
Figure 27A  Figure 27B  Figure 27C  Figure 27D  Figure 27E  Figure 27F

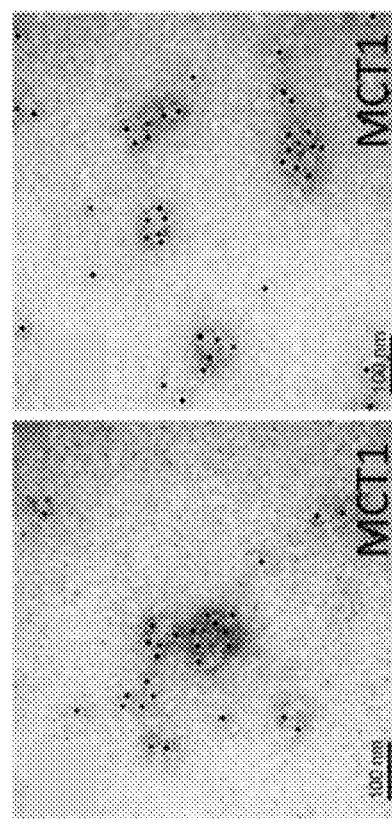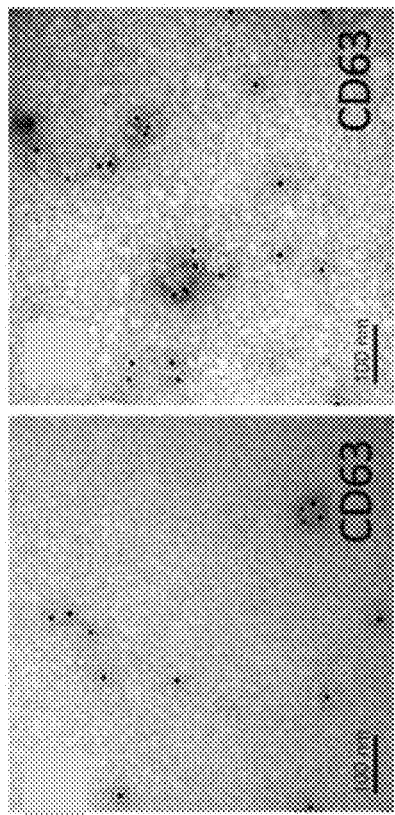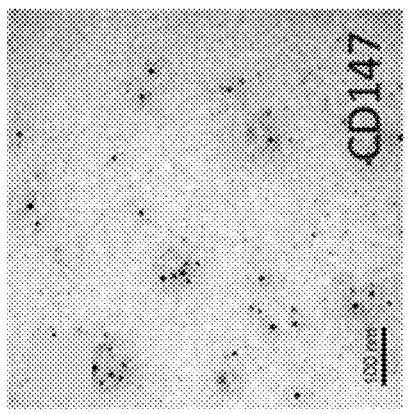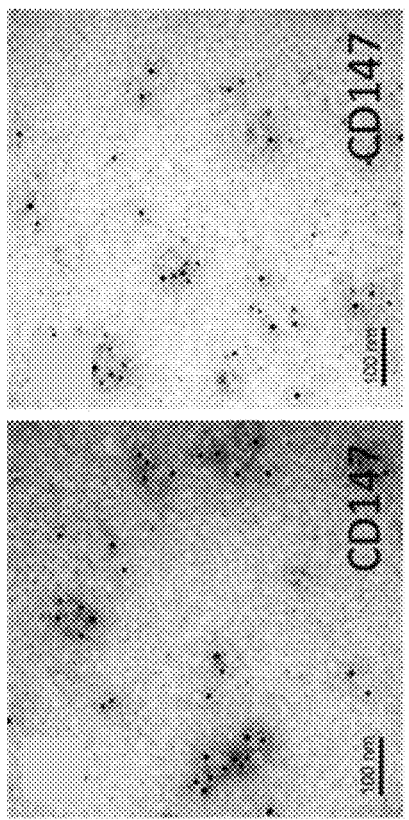
Figure 29A Figure 29B Figure 29C Figure 29D Figure 29E Figure 29F

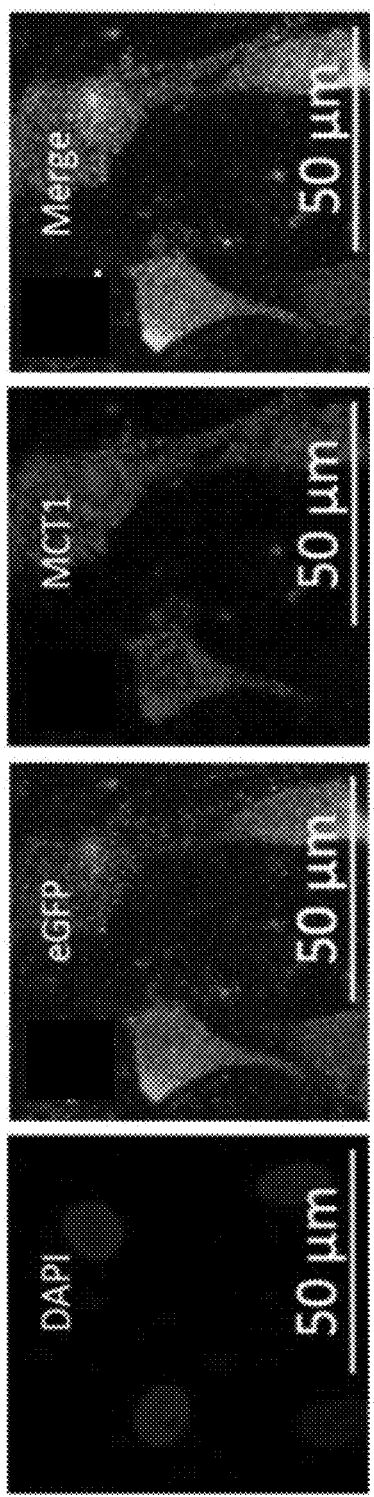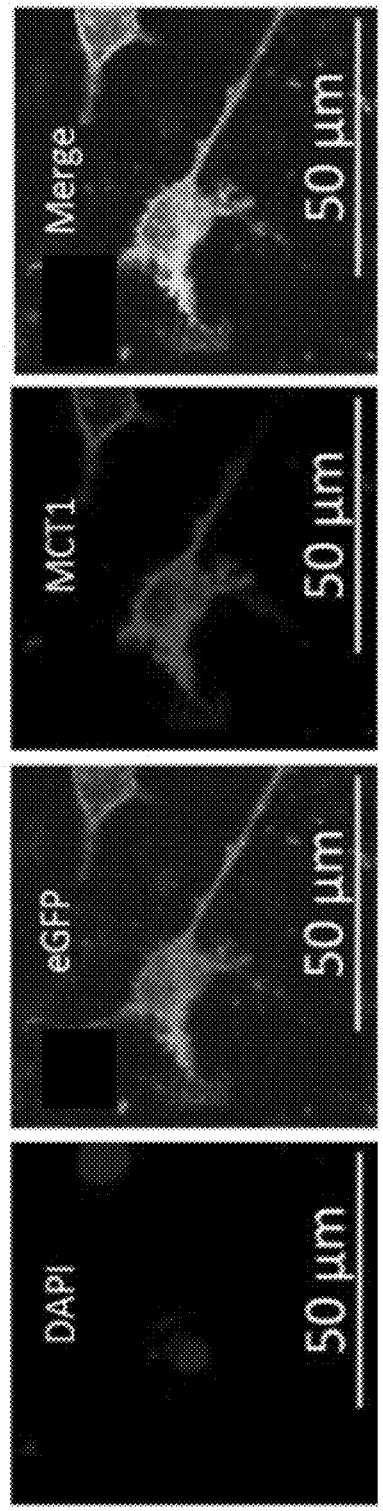
Figure 39A Figure 39B Figure 39C Figure 39D
Figure 39E Figure 39F Figure 39G Figure 39H

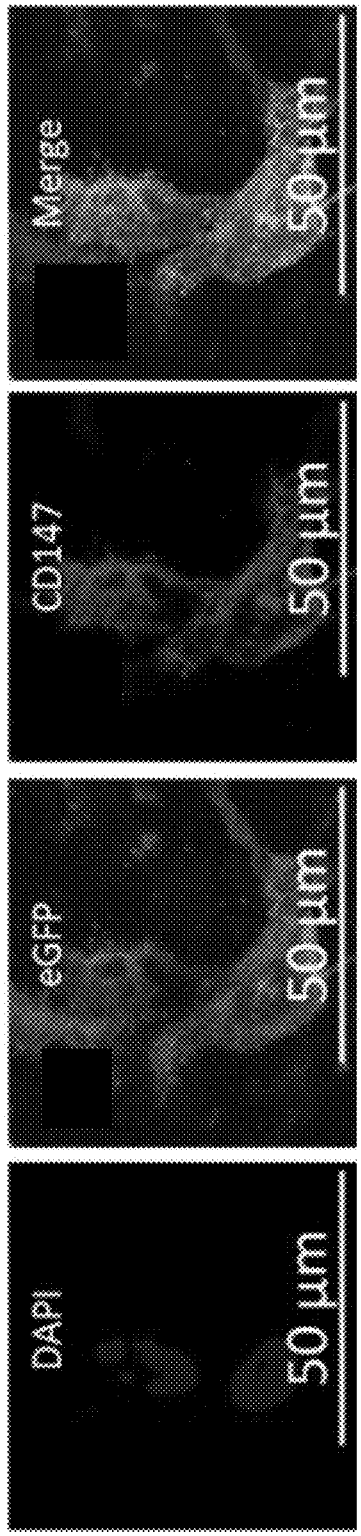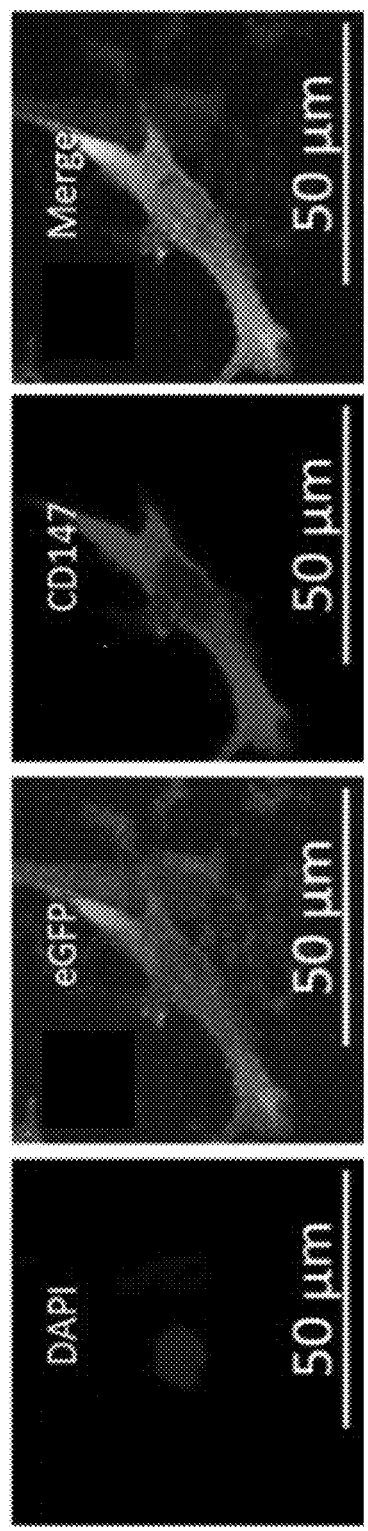

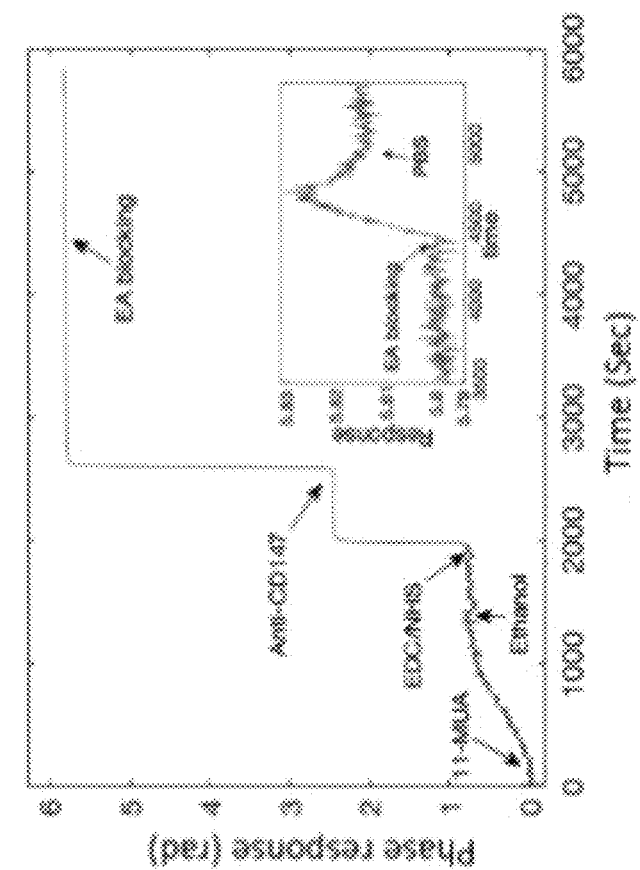
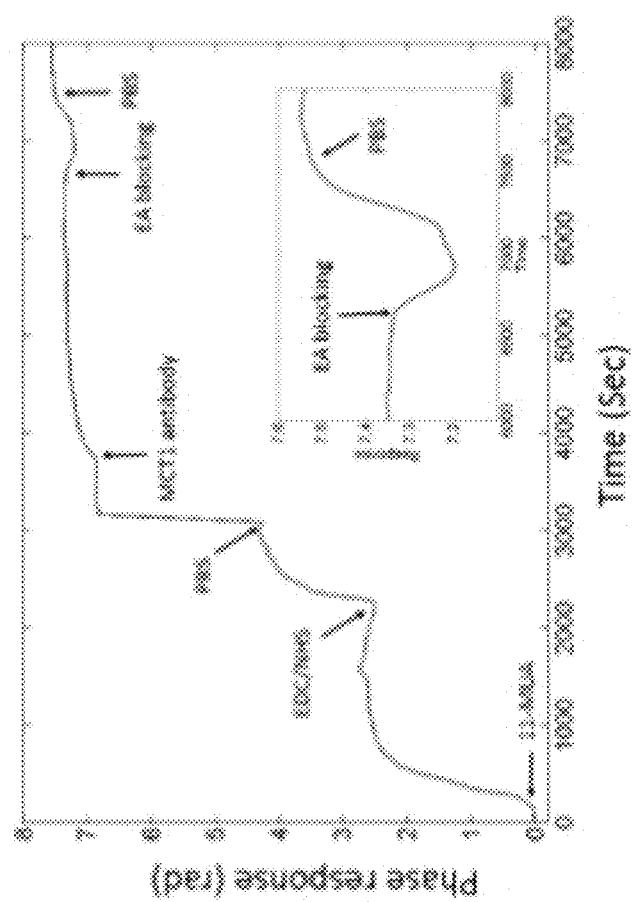
Figure 43B
Figure 43A

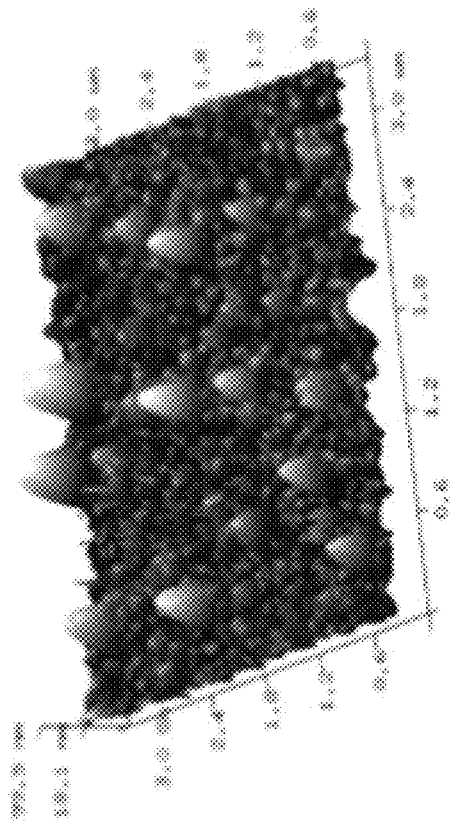
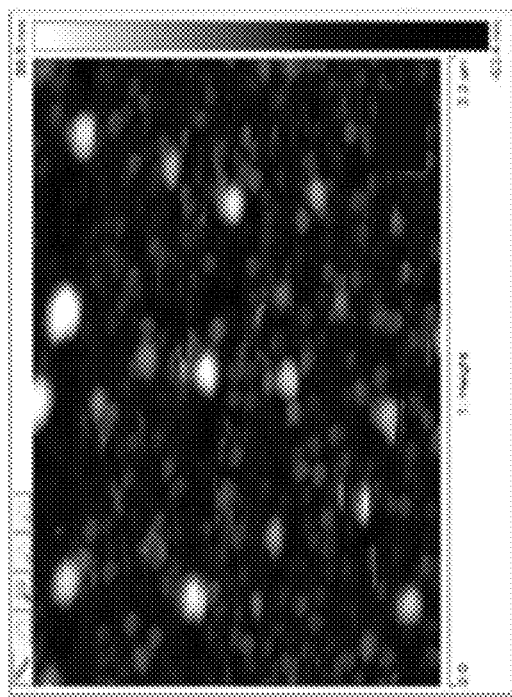
Figure 49A
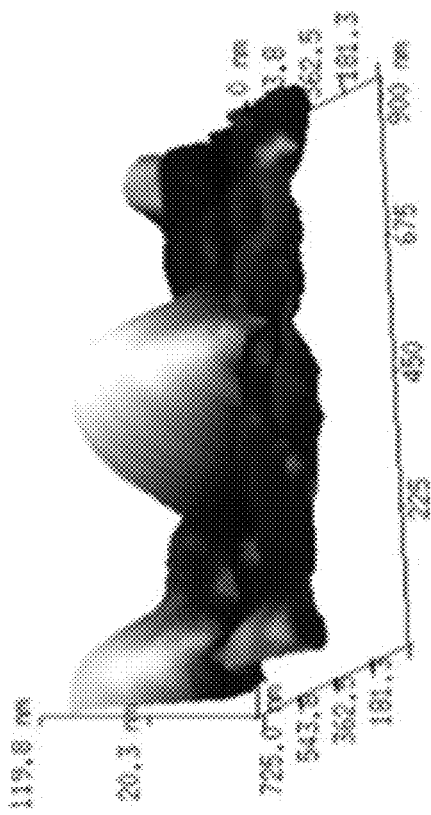
Figure 49B
Figure 49C

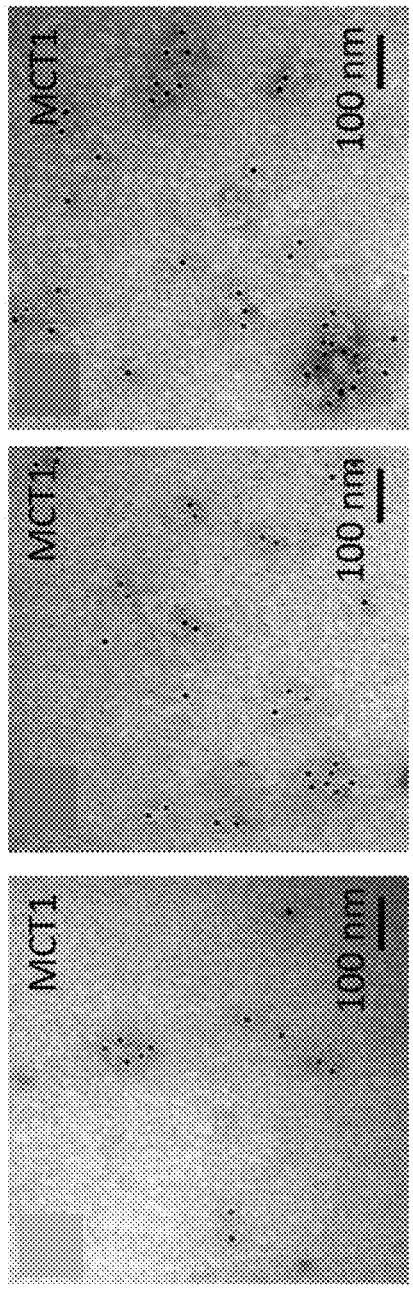
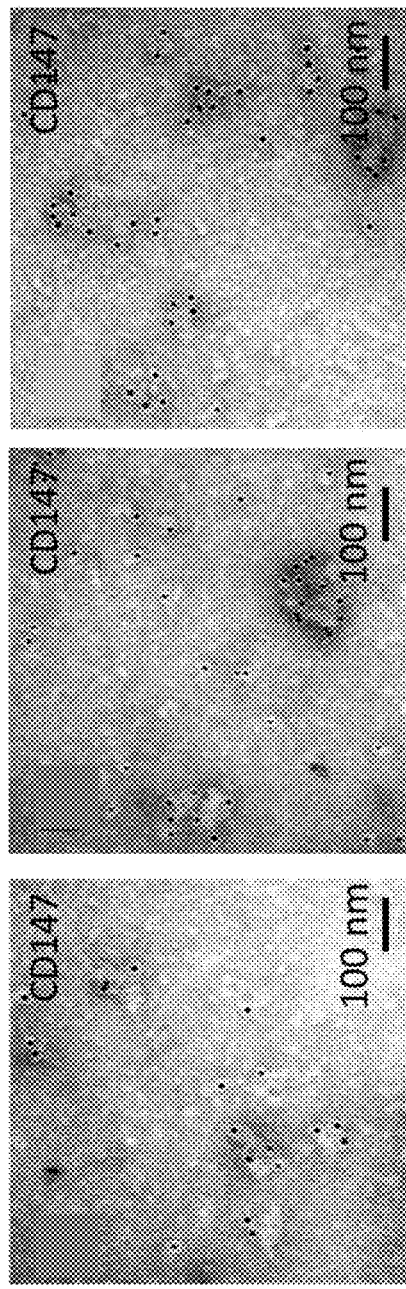
Figure 59A, Figure 59B, Figure 59C, Figure 59D, Figure 59E, Figure 59F

METHODS AND KITS FOR DETECTING EXOSOMAL PROTEIN

TECHNICAL FIELD

The present invention relates to a method for detecting an exosomal protein in a sample particularly a biological sample. The present invention also relates to a kit applicable for performing said method.

BACKGROUND OF THE INVENTION

Conventionally, the diagnosis and prognosis of glioma have been mainly dependent on magnetic resonance imaging (MRI) and computed tomography (CT) scans as well as intracranial biopsies. However, the detection of precise molecular signature of glioma progression and metabolic adaptation has been challenged. Depending on the goal of experiments, EVs, including exosomes and microvesicles (MVs), have commonly been characterized by the multiple techniques and tools, such as nanoparticle tracking analysis (NTA), dynamic light scattering (DLS), scanning electron microscopy (SEM), transmission electron microscopy (TEM), cryo-electron microscopy (cro-EM), immunogold electron microscopy (immunogold EM), flow cytometry, western blotting, and enzyme-linked immunosorbent assay (ELISA). However, these methods have their own limitations.

NTA is a technique which depends on the ability to monitor the Brownian motion of particles (such as exosomes) in a suspension by the detection of light scattering. The movement of illuminated exosomes in a suspension is recorded by camera fitted with an optical microscope. Dynamic movement of exosomes is monitored from the recording video, and the displacement of exosomes versus time is plotted for the analysis. The size distribution of exosomes is calculated by the application of Stokes-Einstein equation. In addition, NTA also provides useful information about both average size and concentration of particles per ml. However, this method has fundamental limitations for the application in biosensing disease-biomarkers, although it can be used to quantify exosome release. In some cases, it technically produces some artefacts in result by the aggregation of exosomes.

Dynamic light scattering (DLS) is a technique which relies on the scattering of a laser beam. It is also referred as photon correlation spectroscopy, where a monochromatic laser beam passes through a suspension of particles. The laser beam becomes dispersed and scattered by the interaction of any particle in its path. The intensity of scattered light is recorded as a function of the reaction time. It can measure the size distribution and zeta potential of exosomes. However, it cannot be used to detect exosomal biomarkers. Also, this method can detect the particles in the size range of 1 nm to 6 μm, however, the data obtained are more reliable when the sample is monodispersed, indicating its limitation in the application for heterogeneous exosomes.

Flow cytometry is a high throughput technique, which can detect EVs quickly. However, it has limited sensitivity and resolution. For instance, it generally precisely detects particles above 500 nm in size with high resolution. Another problem is related the identification and dissection of multiple vesicles as a single event, referred as the "swarming effect". Some other related techniques are impedance-based flow cytometry and imaging flow cytometry for the analysis of EVs.

Western blot has been commonly employed for long time for the quantification of a protein in the study of biochemical and molecular biology, but it has several limitations in the application of exosomal proteins. First, isolated exosome solution has occasionally protein contamination, leading to the production of false positive signal. In addition, for the isolation of exosomal proteins, a huge amount of exosomes is required and isolation of high quality of exosomal proteins, such membrane proteins, is very difficult. Therefore, it is not recommended to quantify exosomal proteins by western blot for detecting disease-biomarkers.

ELISA has also been utilized for the quantification of exosomal proteins by employing plates pre-coated with specific antibodies for various samples. However, it is also challenged due to its relative low sensitivity and potential protein contamination.

All the above-mentioned methods are neither non-invasive nor highly sensitive. Accordingly, there is still an emerging need for alternative approach in detecting exosomes, particularly a non-invasive approach, which can also provide a precise detection and/or is suitable for monitoring a disease progression or diagnosis.

SUMMARY OF THE INVENTION

The inventors, through a number of experiments, found that MCT1 and CD147 are possible biomarkers for tracking the progression of a glioma particularly a malignant glioma in a subject. These biomarkers may also be suitable for disease diagnosis and clinical studies.

In a first aspect of the invention, there is provided a method of detecting one or more exosomal protein in a sample comprising steps of:
  a) introducing the sample on at least a part of a first sensor having a nanostructure thereon, subjecting the first sensor to an optical radiation in a certain spectral range to produce a localized surface plasmon resonance and measuring an induced phase response; and
  b) introducing the sample on a second sensor having a nanostructure thereon, and obtaining an image via atomic force microscopy analysis with a probe functionalized with an antibody targeting the exosomal protein.

In an embodiment, the at least one exosomal protein is MCT1 protein, CD147 protein or a fragment thereof.

In an embodiment, both the first and second sensors have self-assembly gold nanostructure on a surface in contact with the sample.

In an embodiment, the first sensor is immobilized with an antibody capable of binding with the exosomal protein present in the sample.

In an embodiment, the second sensor is immobilized with an antibody for capturing exosomes in the sample for facilitating AFM analysis with the probe.

In an embodiment, the sample is a serum sample comprising exosomes.

In an embodiment, the exosomal protein is indicative of the presence or absence, or pathological progression of a tumor or a cancer.

In an embodiment, the tumor is glioma, and the cancer is malignant glioma.

In an embodiment, the first sensor in step a) is subjected to a common-path interferometric sensing system and differential phase detection.

In an embodiment, the image is a two-dimensional or three-dimensional topographic image.

In a second aspect of the invention, there is provided a kit for detecting at least one exosomal protein in a sample, said kit comprising:
- a first sensor having a nanostructure thereon;
- a second sensor having a nanostructure thereon, and
- a probe functionalized with an antibody targeting the exosomal protein.

In an embodiment, the kit further comprises an activation agent for activating the first sensor, and a mixture containing an antibody targeting the at least one exosomal protein.

In an embodiment, the at least one exosomal protein is MCT1 protein, CD147 protein or a fragment thereof.

In an embodiment, the first sensor is immobilized with an antibody capable of binding with the exosomal protein present in the sample.

In an embodiment, the second sensor is immobilized with an antibody for capturing exosomes in the sample for facilitating AFM analysis with the probe.

In an embodiment, both the first and second sensors have self-assembly gold nanostructures on their surfaces.

In an embodiment, the probe is a silver nitride tip for atomic force microscopy and functionalized with anti-MCT1 antibody or anti-CD147 antibody.

BRIEF DESCRIPTION OF THE DRAWINGS

The patent or application file contains at least one drawing executed in color. Copies of this patent or patent application publication with color drawing(s) will be provided by the Office upon request and payment of the necessary fee Embodiments of the invention will now be described, by way of example, with reference to the accompanying drawings in which:

FIG. 15A is a microscopic image of U251 cells in the control group after 24-hour incubation, as detected by transwell migration assay;

FIG. 15B is a microscopic image of MCT1-overexpressed (MCT1 OE) U251 cells after 24-hour incubation, as detected by transwell migration assay;

FIG. 15C is a microscopic image of MCT1-knockdown (MCT1 KD) U251 cells after 24-hour incubation, as detected by transwell migration assay;

FIG. 15D is a microscopic image of CD147 overexpressed (CD147 OE) U251 cells after 24-hour incubation, as detected by transwell migration assay;

FIG. 15E is a microscopic image of CD147 knockdown (CD147 KD) U251 cells after 24-hour incubation, as detected by transwell migration assay;

FIG. 17A is a plot showing the size distribution and the quantity of exosomes released from cultured normoxic GMs as analyzed by Nanoparticle Tracking Analysis (NTA);

FIG. 17B is a plot showing the size distribution and the quantity of exosomes released from cultured hypoxic GMs as analyzed by NTA;

FIG. 17C is a plot showing the enhanced release of exosomes from hypoxic GMs compared to normoxic GMs;

FIG. 20A is an image of Fura Red calcium dye-loaded hypoxic U251 cells;

FIG. 20B is an image of Fura Red calcium dye-loaded normoxic U251 cells;

FIG. 20C is an image of Fura Red calcium dye-loaded BAPTA-treated U251 cells;

FIG. 20D is a graph showing the effect of increasing hypoxia with both intracellular $Ca^{2+}$ levels;

FIG. 21A is an image of Fura Red calcium dye-loaded GMs with empty backbone;

FIG. 21B is an image of Fura Red calcium dye-loaded U251 cells with the induction of MCT1 OE;

FIG. 21C is an image of Fura Red calcium dye-loaded U251 cells with the induction of MCT1 KD;

FIG. 21D is a graph showing the effect of the induction of MCT1 OE or MCT1 KD with both intracellular $Ca^{2+}$ levels;

FIG. 22A is an image of Fura Red calcium dye-loaded GMs with antisense oligonucleotides control;

FIG. 22B is an image of Fura Red calcium dye-loaded GMs with the induction of CD147 OE;

FIG. 22C is an image of Fura Red calcium dye-loaded GMs with the induction of CD147 KD;

FIG. 22D is a graph showing the effect of the induction of CD147 OE or CD147 KD with both intracellular $Ca^{2+}$ levels;

FIG. 26A is an immunogold EM image of MCT1 in exosomes from normoxic U251 cells;

FIG. 26B is an immunogold EM image of MCT1 in exosomes from hypoxic U251 cells;

FIG. 26C is an immunogold EM image of CD147 in exosomes from normoxic U251 cells;

FIG. 26D is an immunogold EM image of CD147 in exosomes from hypoxic U251 cells;

FIG. 27A is an immunogold EM micrograph of CD63 in exosomes derived from normoxic U87 cells;

FIG. 27B is an immunogold EM micrograph of CD63 in exosomes derived from hypoxia U87 cells;

FIG. 27C is an immunogold EM micrograph of MCT1 in exosomes derived from normoxic U87 cells;

FIG. 27D is an immunogold EM micrograph of MCT1 in exosomes derived from hypoxia U87 cells;

FIG. 27E is an immunogold EM micrograph of CD147 in exosomes derived from normoxic U87 cells;

FIG. 27F is an immunogold EM micrograph of CD147 in exosomes derived from hypoxia U87 cells;

FIG. 29A is an immunogold EM micrograph of CD 63 in exosomes derived from normoxic A172 cells;

FIG. 29B is an immunogold EM micrograph of CD 63 in exosomes derived from hypoxia A172 cells;

FIG. 29C is an immunogold EM micrograph of MCT1 in exosomes derived from normoxic A172 cells;

FIG. 29D is an immunogold EM micrograph of MCT1 in exosomes derived from hypoxia A172 cells;

FIG. 29E is an immunogold EM micrograph of CD147 in exosomes derived from normoxic A172 cells;

FIG. 29F is an immunogold EM micrograph of CD147 in exosomes derived from hypoxia A172 cells;

FIGS. 39A-39D show the immunofluorescent staining for MCT1 in GMs with treated with empty backbone-lentivirus as determined immunocytochemistry (ICC);

FIGS. 39E-39H show the immunofluorescent staining for MCT1 in GMs with treated with MCT1 OE lentivirus as determined immunocytochemistry (ICC);

FIGS. 40A-40D show the immunofluorescent staining for CD147 in GMs with treatment with antisense oligonucleotides control as determined immunocytochemistry (ICC);

FIGS. 40E-40H show the immunofluorescent staining for CD147 in GMs with treatment with CD147 OE antisense oligonucleotides as determined immunocytochemistry (ICC);

FIG. 43A is a graph showing the baseline phase response of the localized surface plasmon resonance (LSPR) biosensor with the functionalized SAM-AuNIs sensing chip with anti-MCT1 antibody after sequential treatment with 11-MUA and EDC/NHS;

FIG. 43B is a graph showing the baseline phase response of the localized surface plasmon resonance (LSPR) biosensor with the functionalized SAM-AuNIs sensing chip with anti-CD147 antibody after sequential treatment with 11-MUA and EDC/NHS;

FIG. 47B shows the separation force responses of the atomic force microscopy (AFM) biosensor with the functionalized silicon nitride tip with anti-CD147 antibody toward equal amount of daughter exosomes from parent U251 GMs with no-treatment, CD147 OE, and CD147 KD;

FIG. 48A is a graph showing the relative strength of atomic force microscopy (AFM) forces toward exosomal MCT1;

FIG. 48B is a graph showing the relative strength of atomic force microscopy (AFM) forces toward exosomal CD147;

FIG. 49A is a two-dimensional image for U251 GMs-derived exosomes immobilized on the SAM-AuNIs sensing chip;

FIG. 49B is a three-dimensional image for U251 GMs-derived exosomes immobilized on the SAM-AuNIs sensing chip;

FIG. 49C is a high resolution of three-dimensional atomic force microscopy (AFM) topographic image for U251 GMs-derived exosomes immobilized on the SAM-AuNIs sensing chip;

FIG. 50 shows the height profile of single U251 GMs-derived exosome by atomic force microscopy (AFM) scanning;

FIG. 51A shows the atomic force microscopy (AFM) separation curves between the functionalized sensing tip with anti-MCT1 antibody toward exosomes on the SAM-AuNIs sample discs;

FIG. 51B is a correlation curve between exosome concentration and the strength of atomic force microscopy (AFM) forces toward exosomal MCT1;

FIG. 52A shows the atomic force microscopy (AFM) separation curves between the functionalized sensing tip with anti-CD147 antibody toward exosomes on the SAM-AuNIs sample discs;

FIG. 52B is a correlation curve between exosome concentration and the strength of atomic force microscopy (AFM) forces toward exosomal CD147;

FIG. 53A shows the separation force responses of the atomic force microscopy (AFM) biosensor with the functionalized cantilever sensing tip with anti-MCT1 antibody toward equal amount of normoxic and hypoxic GMs-derived exosomes;

Figures 53A, 53B:
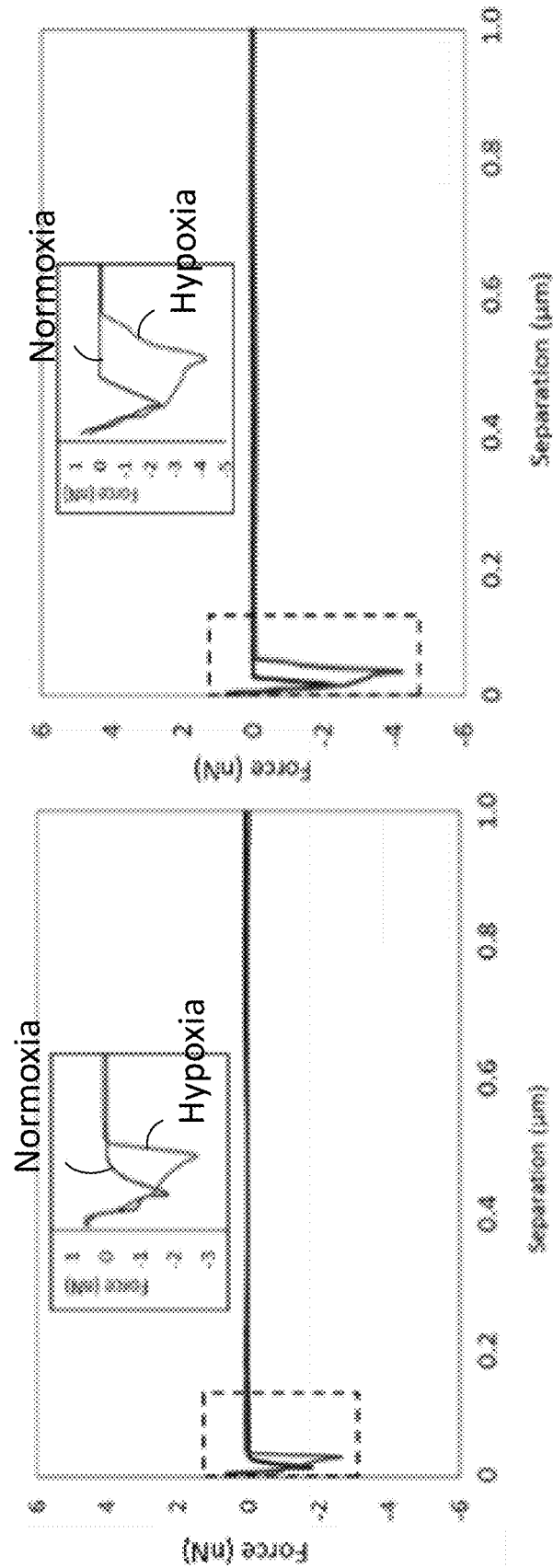
Figure 54B:
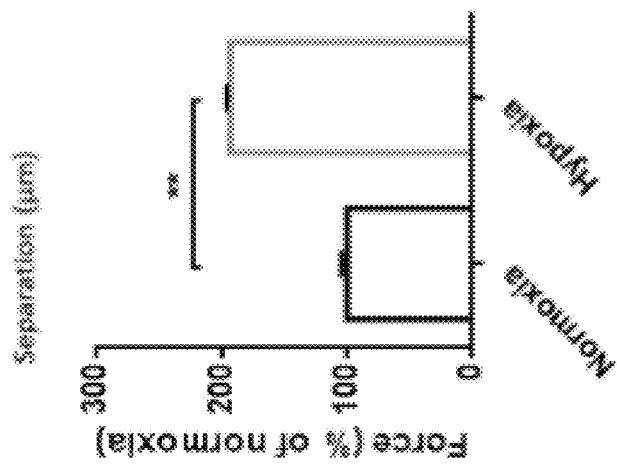
Figure 54A:
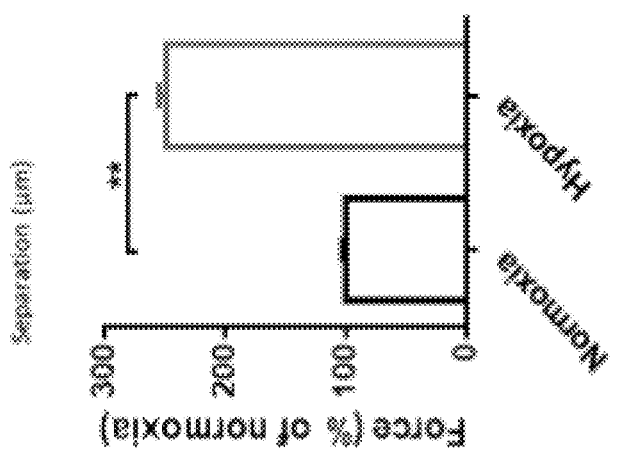
Figures 55A, 55B:
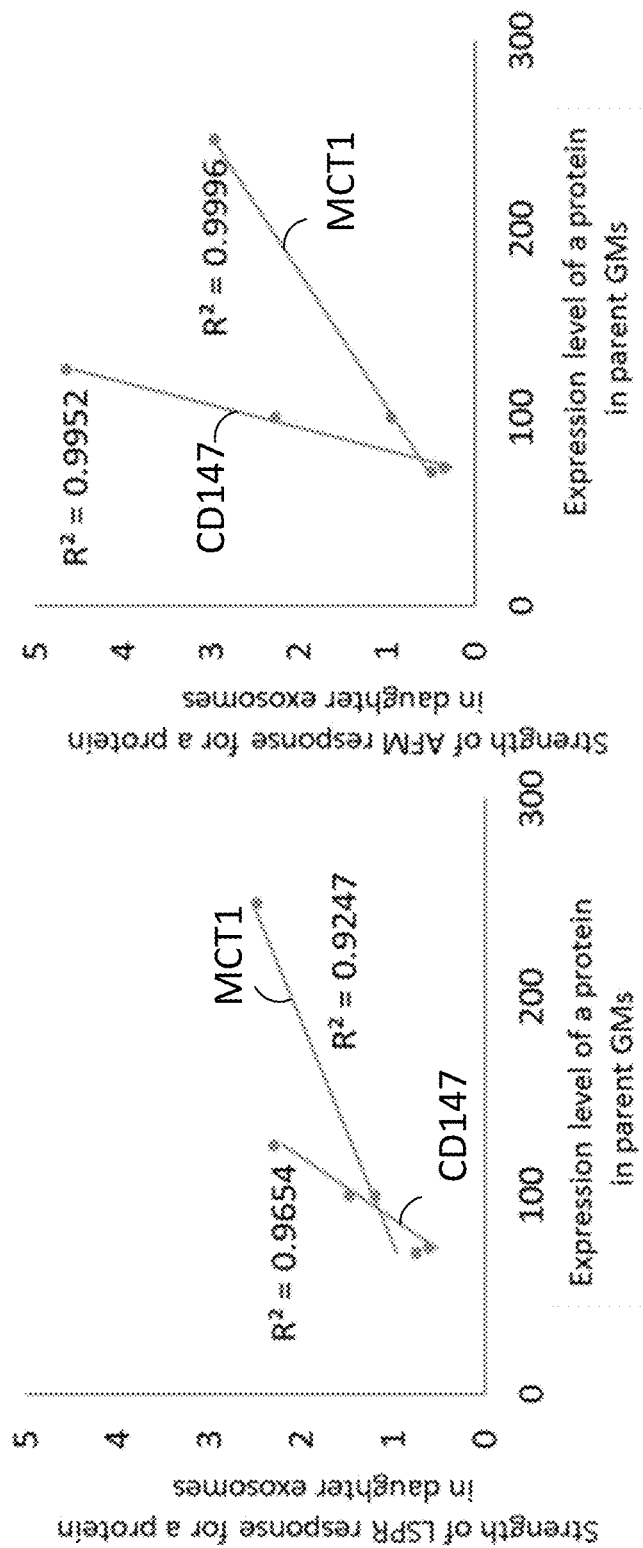
Figure 56C:
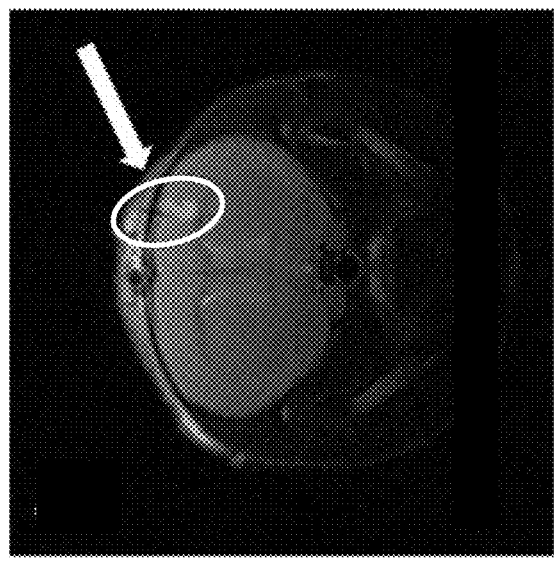
Figure 56B:
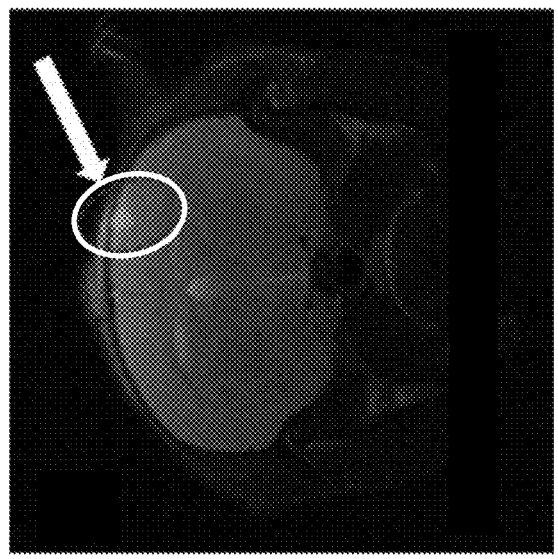
Figure 56A:
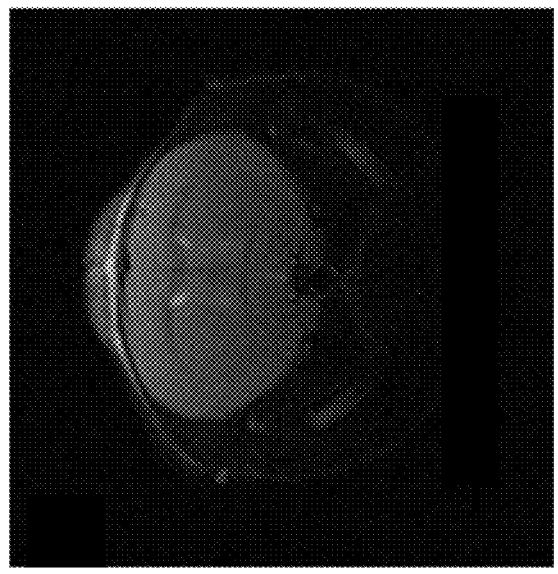
Figure 57C:
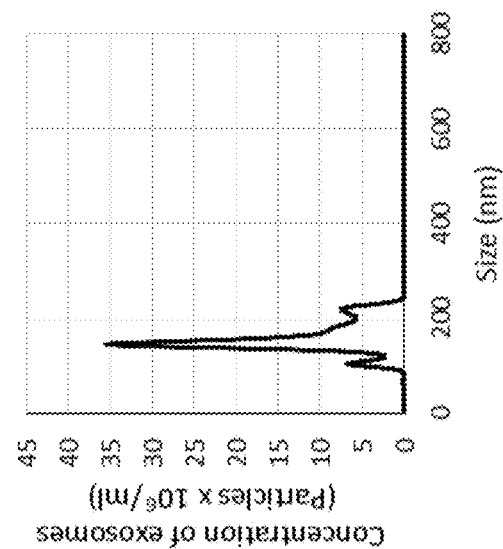
Figure 57B:
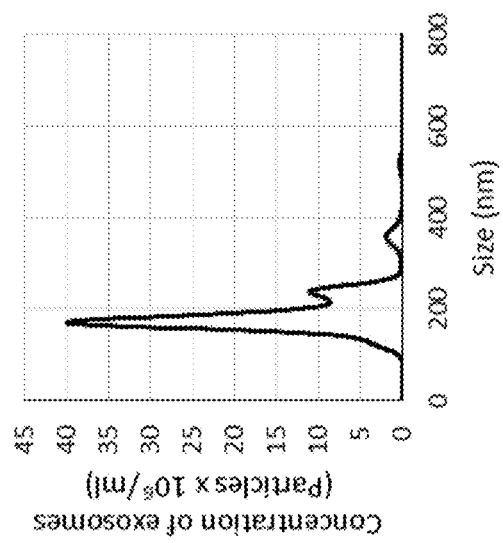
Figure 57A:
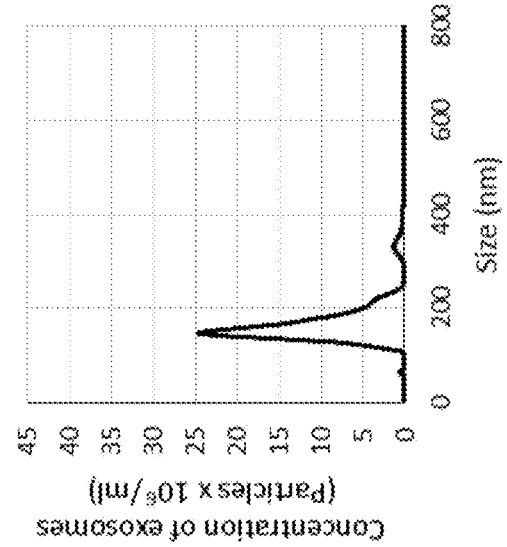
Figures 58A, 58B, 58C:
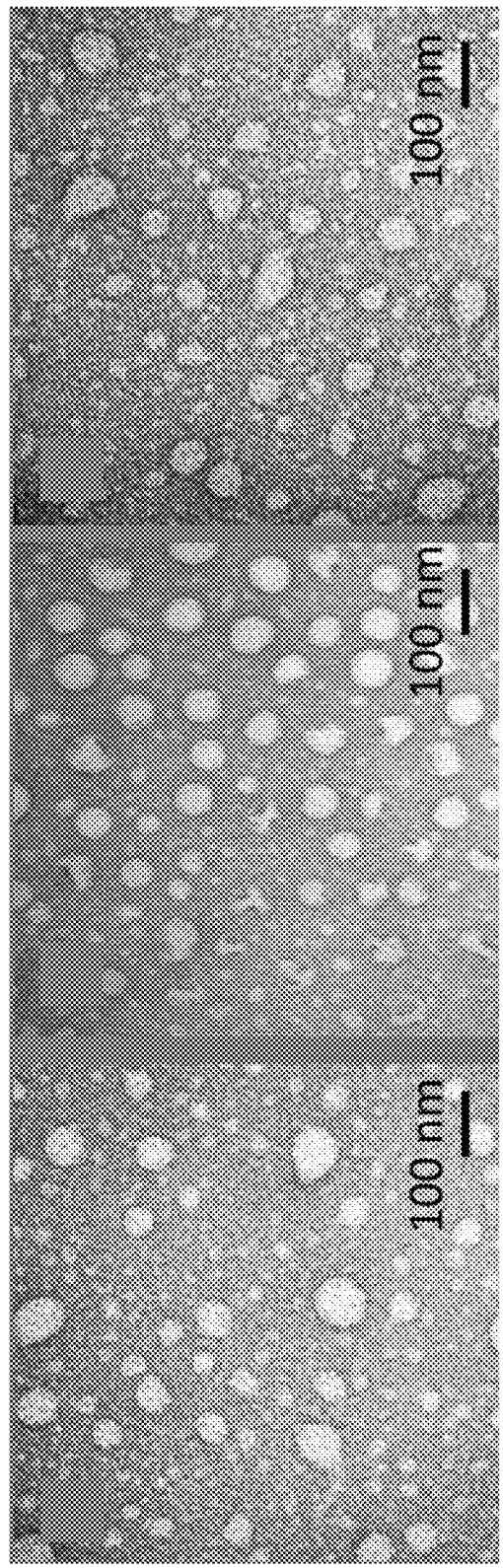
Figure 60B:
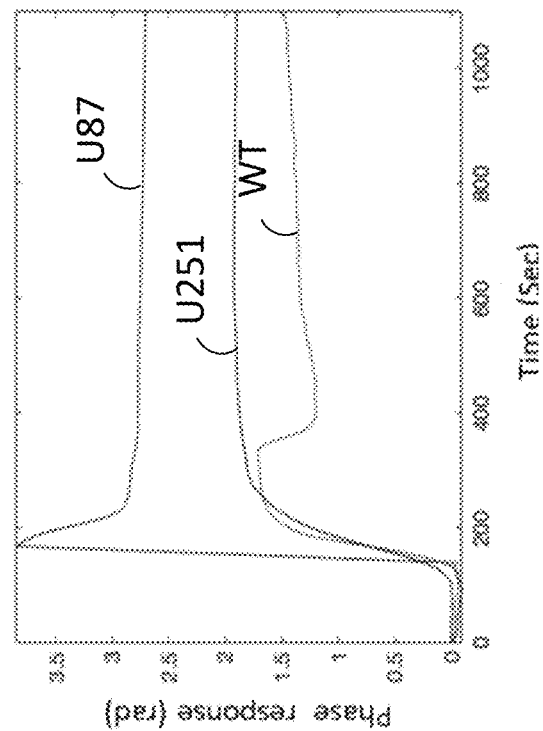
Figure 60A:
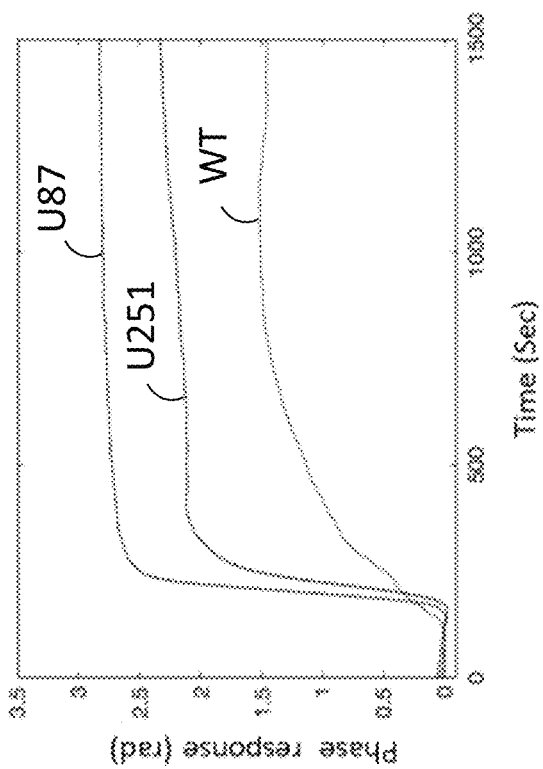
Figure 61A:
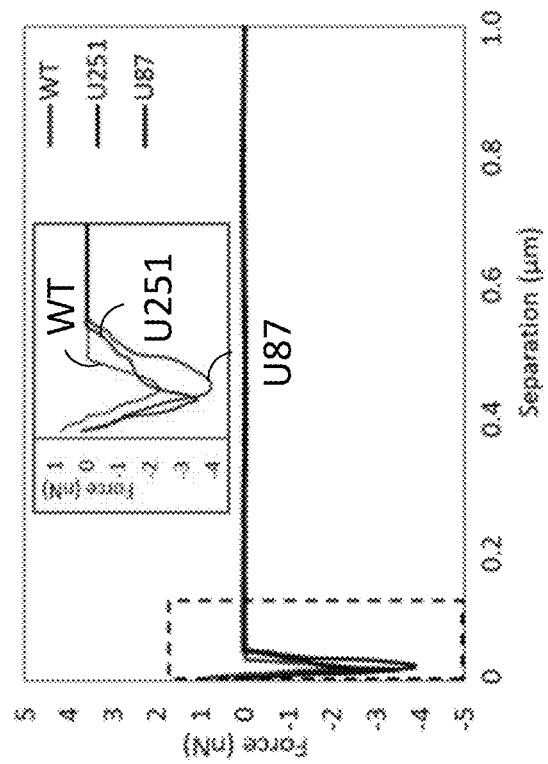
Figure 61B:
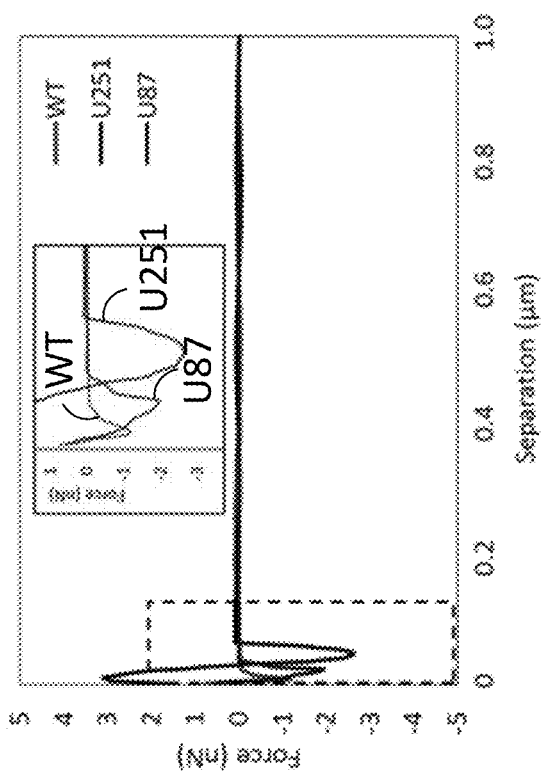

FIG. 53B shows the separation force responses of the atomic force microscopy (AFM) biosensor with the functionalized cantilever sensing tip with anti-CD147 antibody toward equal amount of normoxic and hypoxic GMs-derived exosomes;

FIG. 54A is a graph showing the relative strength of atomic force microscopy (AFM) separation force responses toward exosomal MCT1 from normoxic or hypoxic GMs;

FIG. 54B is a graph showing the relative strength of atomic force microscopy (AFM) separation force responses toward exosomal CD147 from normoxic or hypoxic GMs;

FIG. 55A is a correlation curve between MCT1 or CD147 level in parent GMs and the strength of localized surface plasmon resonance (LSPR) responses toward exosomal MCT1 or CD147;

FIG. 55B is a correlation curve between MCT1 or CD147 level in parent GMs and the strength of atomic force microscopy (AFM) forces toward exosomal MCT1 or CD147;

FIG. 56A is a magnetic resonance imaging (MRI) image for the brain of sham-operated mice;

FIG. 56B is a magnetic resonance imaging (MRI) image for the brain of U251 mouse model of glioma;

FIG. 56C is a magnetic resonance imaging (MRI) image for the brain of U87 mouse model of glioma;

FIG. 57A shows the size distribution and release quantity of exosomes from sham-operated mice, as detected by Nanoparticle Tracking Analysis (NTA);

FIG. 57B shows the size distribution and release quantity of exosomes from U251-glioma model of mice, as detected by Nanoparticle Tracking Analysis (NTA);

FIG. 57C shows the size distribution and release quantity of exosomes from U87-glioma model of mice, as detected by Nanoparticle Tracking Analysis (NTA);

FIG. 58A shows the morphology of exosomes from sham-operated mice, as detected by transmission electron microscopy (TEM) and immunogold electron microscopy (EM);

FIG. 58B shows the morphology of exosomes from U251-glioma model of mice, as detected by transmission electron microscopy (TEM) and immunogold electron microscopy (EM);

FIG. 58C shows the morphology of exosomes from U87-glioma model of mice, as detected by transmission electron microscopy (TEM) and immunogold EM electron microscopy (EM);

FIG. 59A is an image showing the gold dots for MCT1 in exosomes from sham-operated mice, as detected by transmission electron microscopy (TEM) and immunogold electron microscopy (EM);

FIG. 59B is an image showing the gold dots for MCT1 in exosomes from U251-glioma model of mice, as detected by transmission electron microscopy (TEM) and immunogold electron microscopy (EM);

FIG. 59C is an image showing the gold dots for MCT1 in exosomes from U87-glioma model of mice, as detected by transmission electron microscopy (TEM) and immunogold electron microscopy (EM);

FIG. 59D is an image showing the gold dots for CD147 in exosomes from sham-operated mice, as detected by transmission electron microscopy (TEM) and immunogold electron microscopy (EM);

FIG. 59E is an image showing the gold dots for CD147 in exosomes from U251-glioma model of mice, as detected by transmission electron microscopy (TEM) and immunogold EM;

FIG. 59F is an image showing the gold dots for CD147 in exosomes from U87-glioma model of mice, as detected by transmission electron microscopy (TEM) and immunogold electron microscopy (EM);

FIG. 60A shows the phase responses of the localized surface plasmon resonance (LSPR) biosensor with the functionalized SAM-AuNIs sensing chip with anti-MCT1 AB;

FIG. 60B shows the phase responses of the localized surface plasmon resonance (LSPR) biosensor with the functionalized SAM-AuNIs sensing chip with anti-CD147 AB;

FIG. 61A shows the separation force curves of the atomic force microscopy (AFM) biosensor with the functionalized silicon nitride cantilever tip with anti-MCT1 antibody toward serum-derived exosomes from sham-operated mice, U251 and U87 mouse model of glioma; and FIG. 61B shows the separation force curves of the atomic force microscopy (AFM) biosensor with the functionalized silicon nitride cantilever tip with anti-CD147 antibody toward serum-derived exosomes from sham-operated mice, U251 and U87 mouse model of glioma.

Those skilled in the art will appreciate that the invention described herein is susceptible to variations and modifications other than those specifically described. The invention includes all such variations and modifications. The invention also includes all steps and features referred to or indicated in the specification, individually or collectively, and any and all combinations of the steps or features.

DETAILED DESCRIPTION OF THE PREFERRED EMBODIMENT

Unless otherwise defined, all technical terms used herein have the same meaning as commonly understood by one skilled in the art to which the invention belongs.

As used herein, "comprising" means including the following elements but not excluding others. "Essentially consisting of" means that the material consists of the respective element along with usually and unavoidable impurities such as side products and components usually resulting from the respective preparation or method for obtaining the material such as traces of further components or solvents. "Consisting of" means that the material solely consists of, i.e. is formed by the respective element. As used herein, the forms "a," "an," and "the," are intended to include the singular and plural forms unless the context clearly indicates otherwise. Other than in the working examples, or where otherwise indicated, all numbers used herein should be understood as modified in all instances by the term "about".

The present invention provides a method of detecting one or more exosomal protein in a sample, said method comprises:
a) introducing the sample on at least a part of a first sensor having a self-assembly structure thereon, subjecting the first sensor to an optical radiation in a certain spectral range to produce a localized surface plasmon resonance and measuring an induced phrase response; and
b) introducing the sample on a second sensor having a self-assembly structure thereon, and obtaining an image via atomic force microscopy analysis with a probe functionalized with an antibody targeting the exosomal protein.

The term "exosomal protein" refers to a protein that is present in or on an exosome. Exosomes are extracellular vesicles that are produced in the endosomal compartment of cells. They are, in general, small vesicles in a range of about 10 nm to about 100 nm and are derived from the multivesicular bodies. Preferably, the exosomal protein referred to in this invention is indicative of the presence or absence, or pathological progression of a disease particularly a tumor or a cancer. In an embodiment, the exosomal protein is monocarboxylate transporter 1 (MCT1) or cluster of differentiation 147 (CD147). These proteins are especially advantageous in monitoring the progress of a glioma or diagnosis of malignant glioma including, but is not limited to, glioblastoma.

The sample used herein is preferably a biological sample obtained from a living source including, but is not limited to, a human and an animal. It can be obtained from a patient suffering from a disease including a tumor or a cancer. The sample can be in any form and may be a biological fluid. In an embodiment, the sample comprises or consists of blood, serum, saliva, urine, or tissue fluid and particularly the sample is a serum sample. In a particular embodiment, the sample is a serum sample obtained from a subject suffering from glioma or malignant glioma.

The term "sensor" used herein refers to a substance that facilitates detection of an analyte in a direct or indirect manner. The sensor may be equipped with a sensing molecule that can bind or interact with the analyte to facilitate detection or provide signals including, but are not limited to, visible or electrical signals for detection. In an embodiment, the sensor includes a substrate providing a surface for interacting with the analyte in the sample. The substrate may be made from an inert material such as glass and silica, and in the form of a film, a sheet, a mesh, or a cube. In an embodiment, the sensor includes a glass substrate configured with nanostructures. In another embodiment, the first sensor is different or independent from the second sensor.

The term "nanostructures" used herein refers to any solid or flexible elements formed on the surface of the sensor which have an average diameter or maximum length of from about 1 nm to about 1000 nm, from about 1 nm to about 100 nm, or from about 5 nm to about 50 nm. In an embodiment, the nanostructures comprise or consist of gold, and may be self-assembly gold nanostructures. The provision of self-assembly gold nanostructures on the sensor allows precise detection of phase response in LSPR detection. In particular, self-assembly gold nano-islands (abbreviated as SAM AuNIs) can be fabricated on a glass substrate to form a sensor by two-step thin-film deposition-annealing method as described in T. Karakouz, et al., Adv. Mater. 20, 3893 (2008).

Step a) of the method in particular makes use of an improved localized surface plasmon resonance (LSPR) technology to detect the presence, absence or amount of the target exosomal protein in the sample. It may include a step of introducing the sample on the first sensor which is configured to have self-assembly gold nanostructures thereon and immobilized with one or more antibodies against the one or more exosomal proteins in the sample. The first sensor may be a glass substrate functionalized with SAM AuNIs and one or more antibodies. The immobilized antibodies are capable of binding with the loose or free-moving exosomes in the sample which is preferably a sample solution.

In an embodiment, the sample solution is introduced to the first biosensor in a LSPR system by using a peristaltic pump at a constant rate. During the introduction, the first sensor is subjected to an optical radiation in a spectral range, for example under various refractive indices, to generate phase responses. The detected phase response can then be correlated to the level of the exosomal protein in the sample.

In an embodiment, the first sensor is particularly subjected to a common-path interferometric sensing system and differential phase detection so as to measure the differential phase induced by LSPR effect of the SAM gold nano-isolands (SAM AuNIs) at various refractive indices.

Step b) of the method includes a further analysis making use of an improved atomic force microscopy (AFM) technology to reconfirm the results obtained in step a). In particular, the sample or another portion of the sample is introduced to the second sensor which may be another substrate functionalized with SAM AuNIs fabricated as described above. This second sensor is preferably arranged as an AFM biosensor to immobilize exosomes on the surface first before carrying out detection. Preferably, the second sensor is immobilized with an antibody capable of capturing exosomes in the sample for facilitating AFM analysis with the probe. For example, the second sensor is immobilized with anti-CD63 antibody to capture the exosomes or hold them in place for subsequent detection.

Step b) also includes the step of obtaining the image by using the probe which is functionalized with an antibody targeting the exosomal protein to measure the intermolecular force between the exosomal protein and the antibody for detection. The probe is preferably a silver nitride AFM probe having a tip functionalized with an antibody against the exosomal protein of interest.

Based on the detected responses, step b) generates a two-dimensional and/or three-dimensional topographic image of the sample. This is advantageous in that a user can study the morphologies of the cells as well as confirm the results based on the images.

In an embodiment where the exosomal protein of interest is MCT1 protein or a fragment thereof, the antibody immobilized on the first sensor and the probe is anti-MCT1 antibody. In an embodiment where the exosomal protein of interest is CD147 protein or a fragment thereof, the antibody immobilized on the first sensor and the probe is anti-CD147 antibody.

The method herein generally involves label-free sensing of exosomal MCT1 and CD147 as novel surrogate biomarkers for metabolic reprogramming and malignant progression of glioma. The presently invention is suitable for disease diagnosis particular diagnosis of glioma or malignant glioma, and is suitable for monitoring the health condition of a subject suffering from said disease. Since a blood sample or a serum sample is sufficient for detection, this invention allows a feasible non-invasive approach for clinical or therapeutic applications.

The present invention also provides a kit for detecting at least one exosomal protein as described above in a sample. The kit can be utilized to perform the method as described herein. In particular, the kit comprises a first sensor having a nanostructure thereon; a second sensor having a nanostructure thereon, and a probe functionalized with an antibody targeting the exosomal protein.

In particular, the first and second sensors are as described above. Preferably, both the first and second sensors have self-assembly gold nanostructures on their surfaces for interacting with the exosomal proteins in the sample.

In an embodiment, both the first sensor and the probe is immobilized with the same antibody capable of binding with the exosomal protein present in the sample. The second sensor is immobilized with an antibody for capturing exosomes in the sample for facilitating AFM analysis with the probe.

In an embodiment where the exosomal protein of interest is MCT1 protein, CD147 protein or a fragment thereof, the probe is a silver nitride tip for AFM analysis and functionalized with anti-MCT1 antibody or anti-CD147 antibody.

In an embodiment where the first sensor is not immobilized with an antibody yet, the kit may further comprise an activation agent for activating the first sensor, and a mixture containing an antibody targeting the at least one exosomal protein for immobilization on the first sensor.

The kit can be packaged with a user manual or label to teach a user to use the sensors and probe properly in the corresponding LSPR and AFM detections.

The examples set out below further illustrate the present invention. The preferred embodiments described above as well as examples given below represent preferred or exemplary embodiments and a skilled person will understand that the reference to those embodiments or examples is not intended to be limiting.

Figure 1:
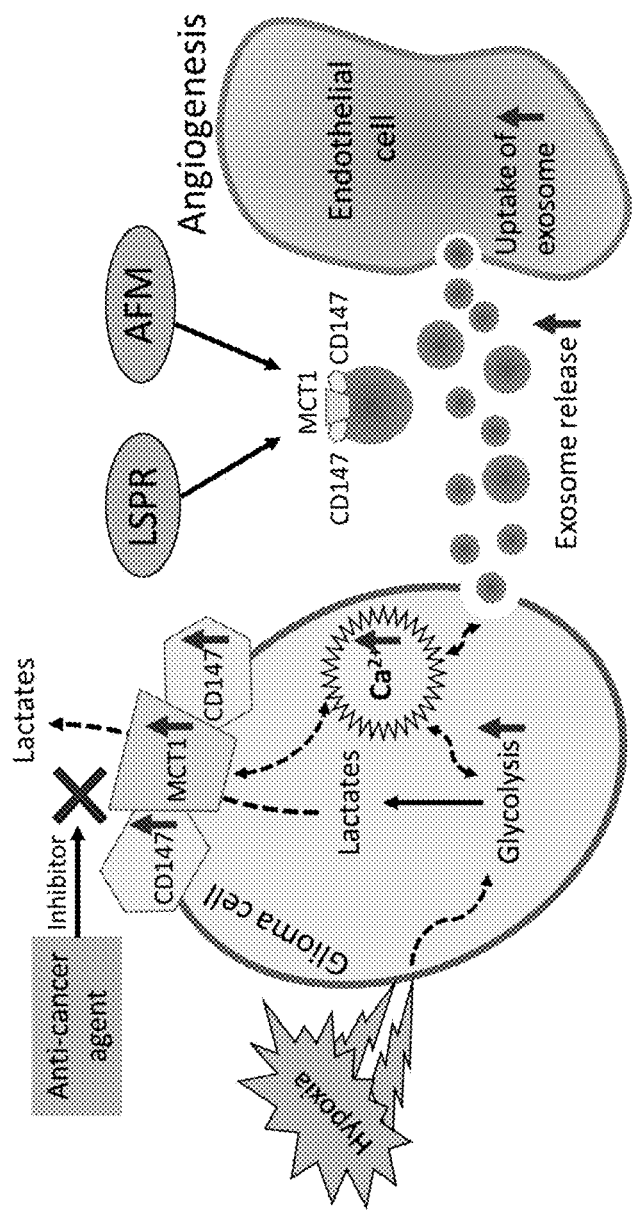
FIG. 1 is a schematic diagram illustrating at a glioma cell has enriched MCT1 and CD147 on the plasma membrane facilitating the formation of daughter exosomes with enhanced exosomal MCT1 and CD147 expressions, and the daughter cells can be uptaken by an endothelial cell.
Figure 2C:
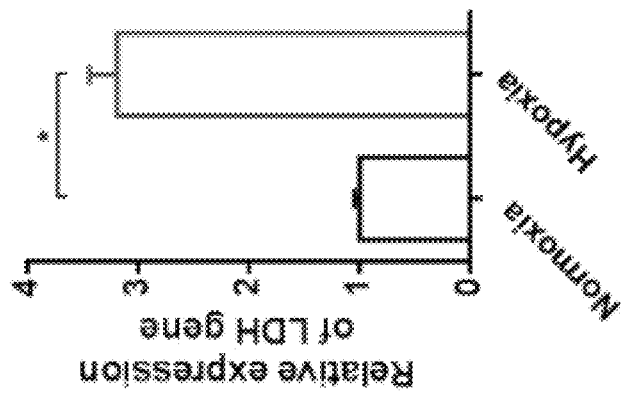
FIG. 2C shows the change in the mRNA expression of LDH in U251 GMs in response to hypoxia.
Figure 2B:
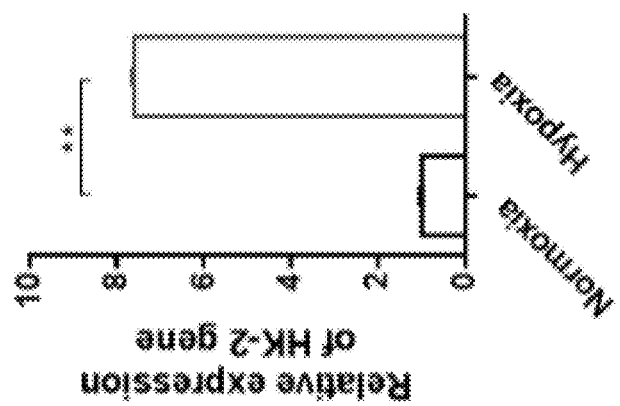
FIG. 2B shows the change in the mRNA expression of HK-2 in U251 GMs in response to hypoxia.
Figure 2A:
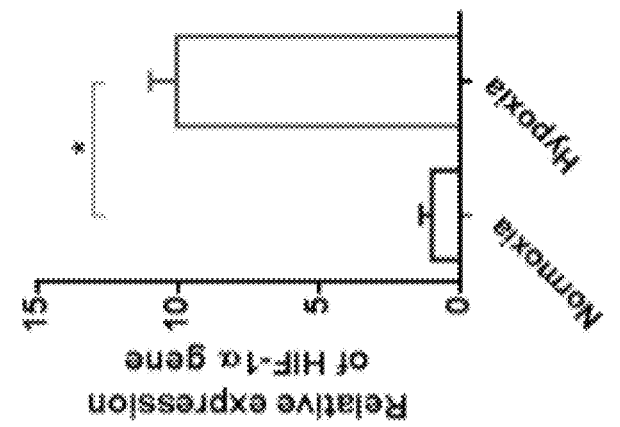
FIG. 2A shows the change in the mRNA expression of HIF-1α in U251 GMs in response to hypoxia.
Figure 2F:
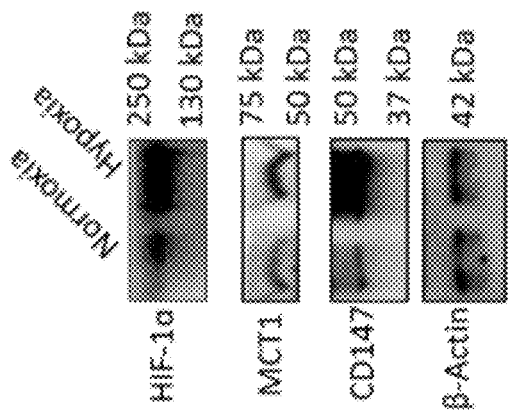
FIG. 2F shows the protein-level change of HIF-1α, MCT1, and CD147 in U251 GMs in response to hypoxia.
Figure 2E:
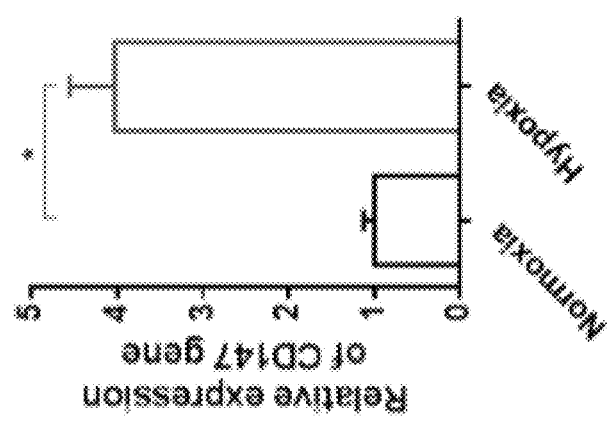
FIG. 2E shows the change in the mRNA expression of CD147 in U251 GMs in response to hypoxia.
Figure 2D:
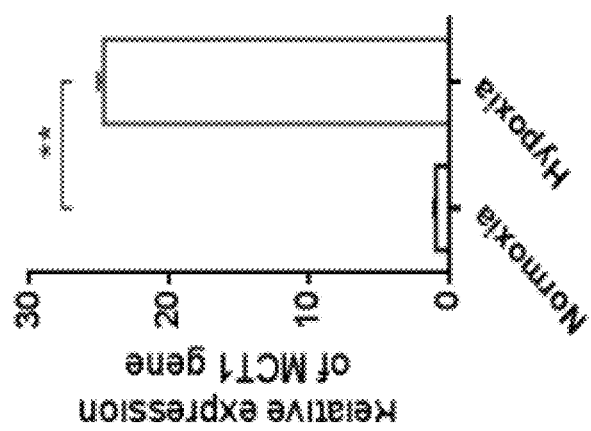
FIG. 2D shows the change in the mRNA expression of MCT1 in U251 GMs in response to hypoxia.

With reference to FIG. 1, the inventors found that under hypoxia, one of the major hallmarks of tumor microenvironment, the expression monocarboxylate transporter 1 (MCT1) and cluster of differentiation 147 (CD147) in malignant glioma cells (abbreviated as GMs) are upregulated along with other glycolytic genes to facilitate the exocytosis of increased intracellular lactates. The release of exosomes is enhanced from GMs, which is controlled by MCT1 and CD147 along with calcium dependent manner. The enhanced exosomal MCT1 and CD147 can be precisely detected by label free self-assembly gold nanoislands (SAM-AuNIs) localized surface plasmon resonance (LSPR) and SAM-AuNIs atomic force microscopy (AFM) biosensors to monitor the metabolic reprogramming and malignant progression of glioma.

Example 1

Effect of Hypoxia on Tumor Progression of Malignant Glioma

It was first determined the effect of hypoxia on the progression of tumor particularly malignant glioma by using human glioblastoma cell lines. In the experiment, malignant glioma cells (abbreviated as GMs) were divided into two groups: hypoxia group and control group. Hypoxia group refers to GMs being exposed to hypoxic chamber (1% O2), or $CoCl_2$ (100 µM) to induce hypoxia. Control group, i.e. normoxia group, refers to GMs being exposed to ordinary incubation conditions without hypoxia induction. Different GM cell lines were used in the experiment including U251 cells, U87 cells, U118 cells, and A172 cells.

After incubation with or without hypoxia induction, the cells in each group were then collected and lysed. The expression of hypoxia inducible factor1 alpha (HIF-1α) gene, glycolytic genes including hexokinase 2 (HK-2) gene, lactate dehydrogenase (LDH) gene, MCT1 gene and CD147 gene in GMs of each group were determined by using quantitative real-time polymerase chain reaction (qRT-PCR), Western blot analysis, and immunofluorescent staining. These analysis methods can be carried out according to standard protocols available in the field.

The results are as shown in FIGS. 2A to 11. In particular, FIG. 2A-2E show the change in the mRNA expression of HIF-1α, HK-2, LDH, MCT1, and CD147, respectively, in U251 cells in response to hypoxia (1% O2) (n=3), as determined by qRT-PCR. FIG. 2F shows the protein-level change of HIF-1α, MCT1, and CD147 in U251 cells in response to hypoxia (1% 02), as determined by Western Blot (WB). These results show that the mRNA expression of HIF-1α, HK-2, LDH, MCT1, and CD147 increases under hypoxia as compared to that under normoxia.

Figure 3:
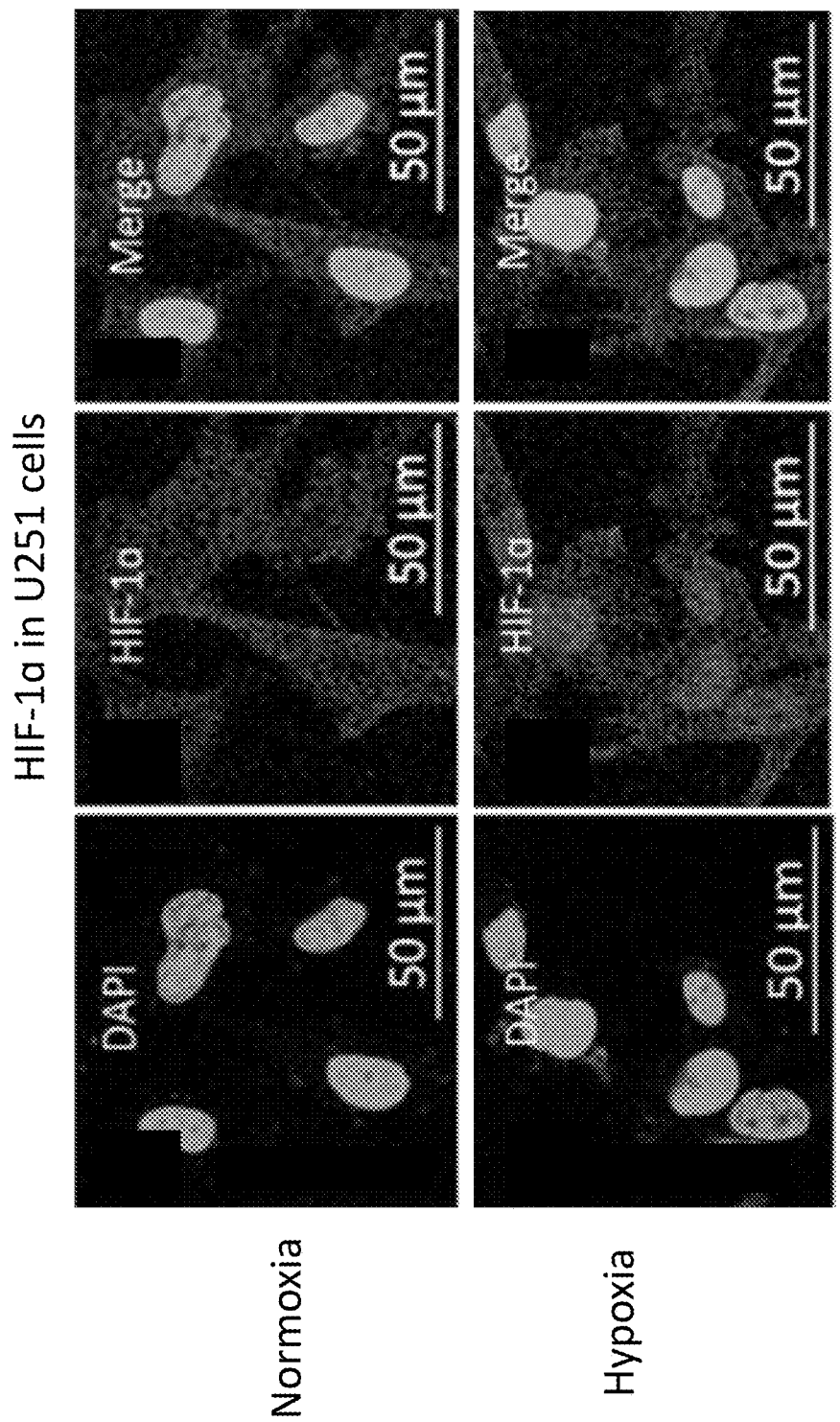
FIG. 3 shows the expression of HIF-1α in U251 cells under normoxia (upper panel) or hypoxia (lower panel) after immunofluorescent staining, in which the cells were treated with 4,6'-diamidino-2-phenylindole (DAPI) to locate the nucleus, and an antibody of HIF-1α.
Figure 4:
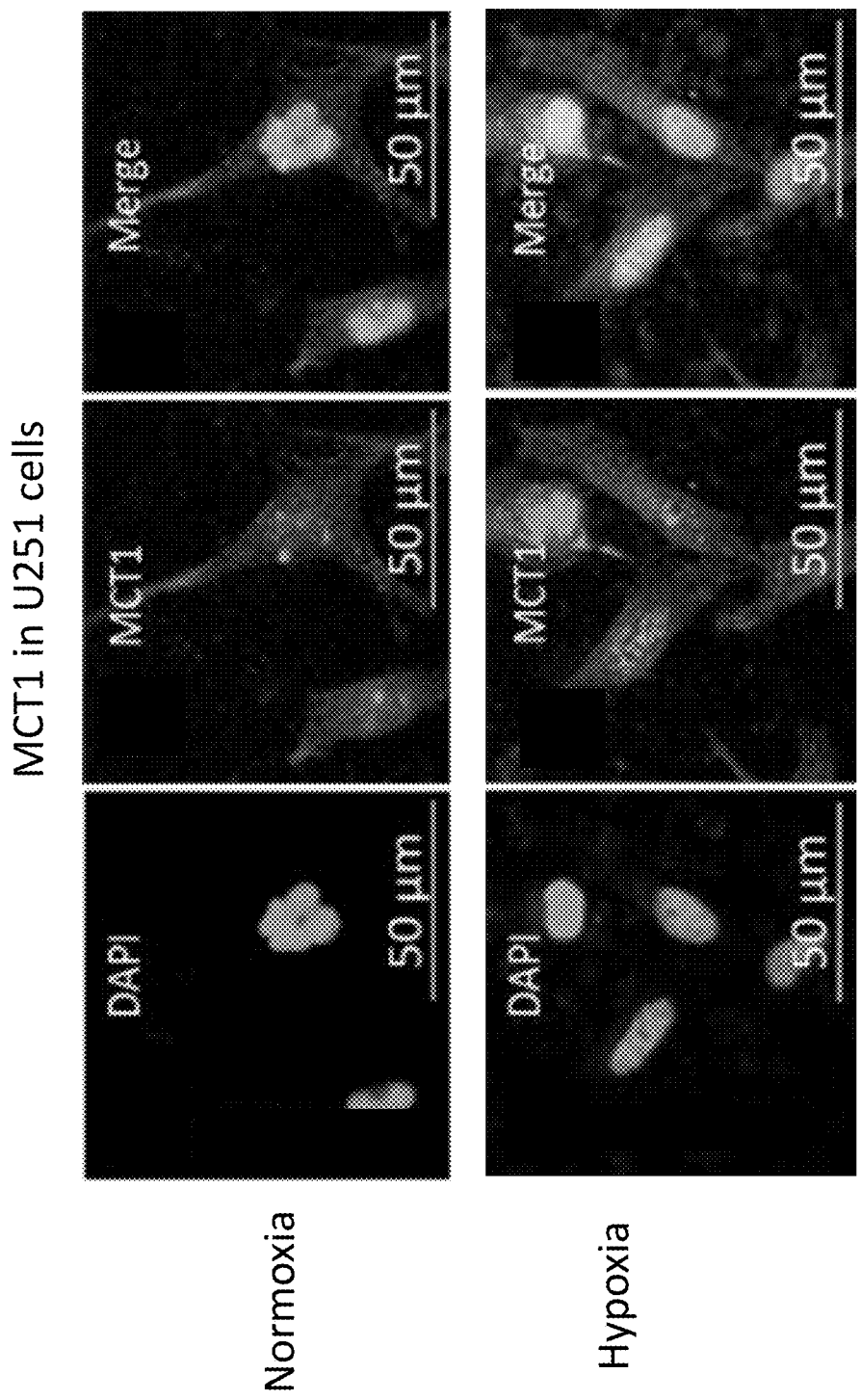
FIG. 4 shows the expression of MCT1 in U251 cells under normoxia (upper panel) or hypoxia (lower panel) after immunofluorescent staining, in which the cells were treated with DAPI to locate the nucleus, and Alexa 488 to indicate the presence of MCT1 in the cells.
Figure 5:
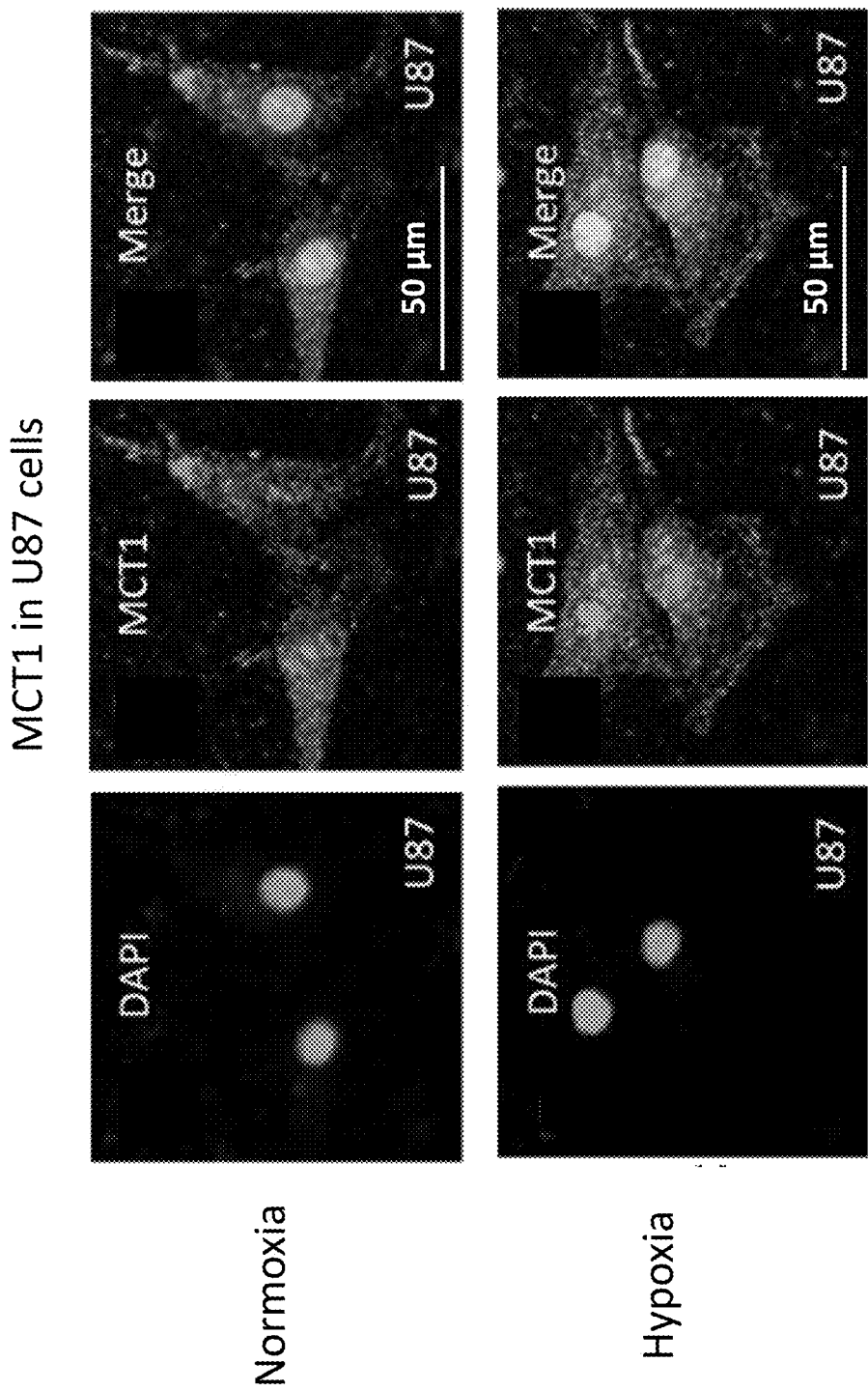
FIG. 5 shows the expression of MCT1 in U87 cells under normoxia (upper panel) or hypoxia (lower panel) after immunofluorescent staining, in which the cells were treated with DAPI to locate the nucleus, and Alexa 488 to indicate the presence of MCT1 in the cells.
Figure 6:
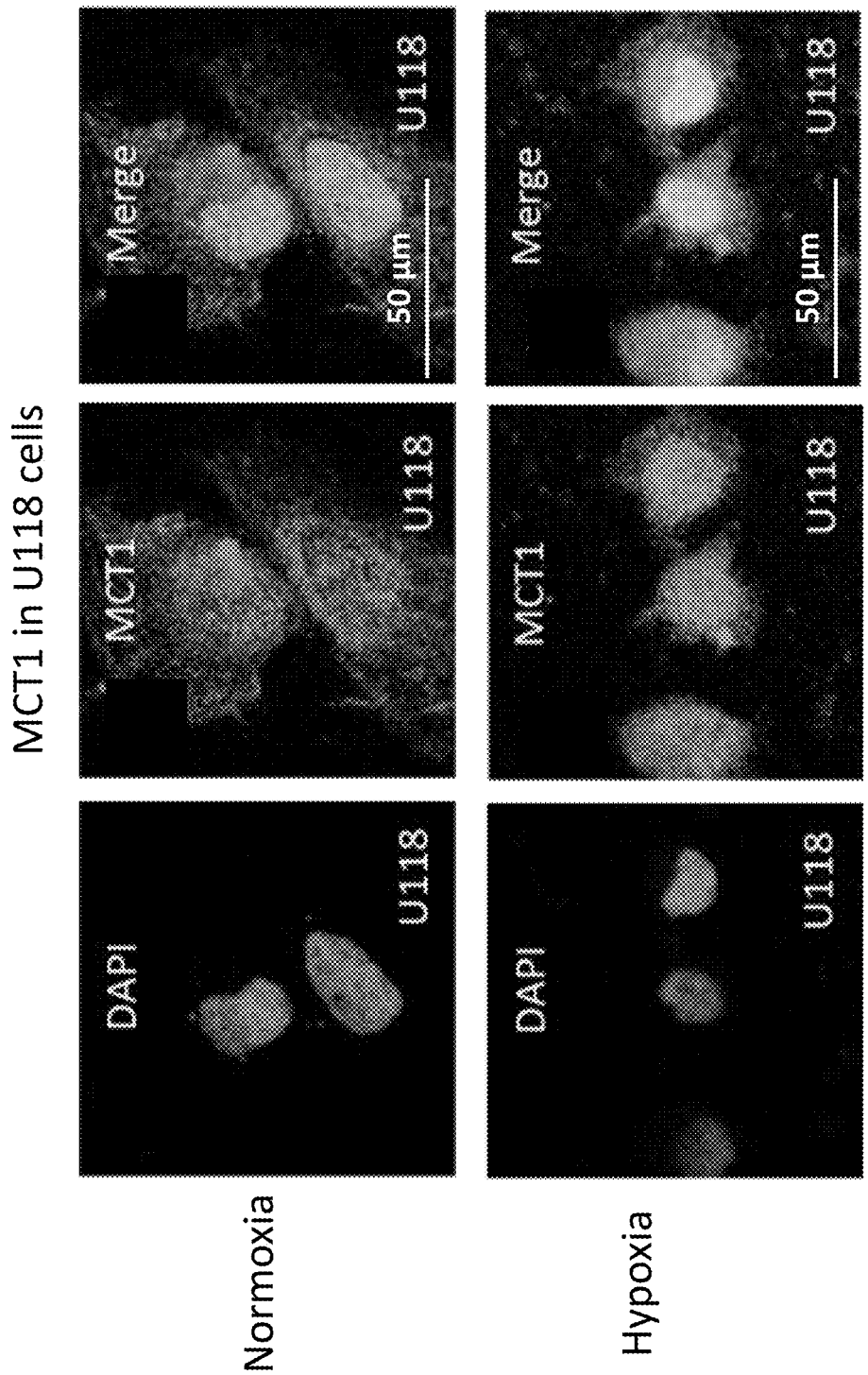
FIG. 6 shows the expression of MCT1 in U118 cells under normoxia (upper panel) or hypoxia (lower panel) after immunofluorescent staining, in which the cells were treated with DAPI to locate the nucleus, and Alexa 488 to indicate the presence of MCT1 in the cells.
Figure 7:
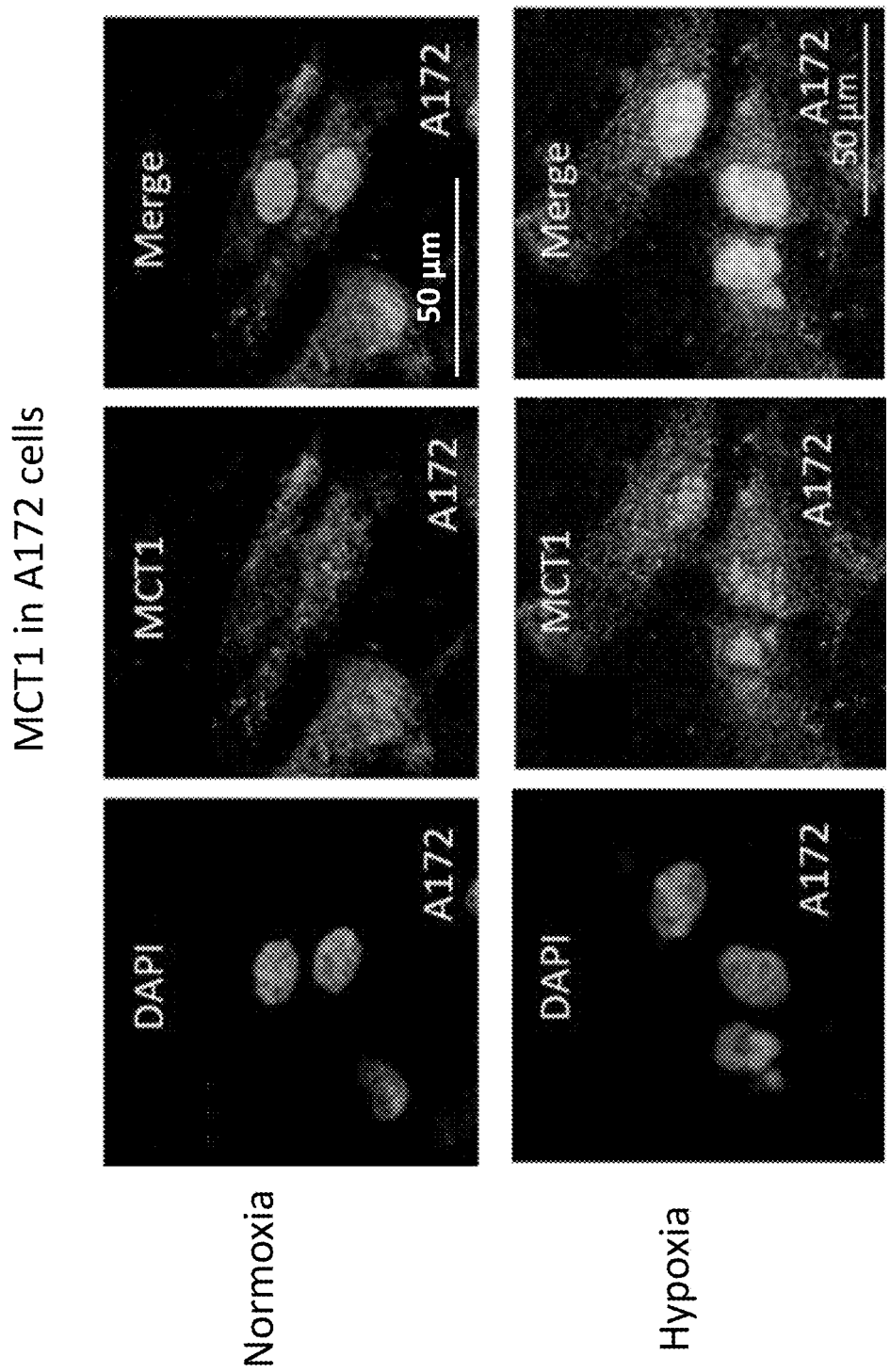
FIG. 7 shows the expression of MCT1 in A172 cells under normoxia (upper panel) or hypoxia (lower panel) after immunofluorescent staining, in which the cells were treated with DAPI to locate the nucleus, and Alexa 488 to indicate the presence of MCT1 in the cells.
Figure 8:
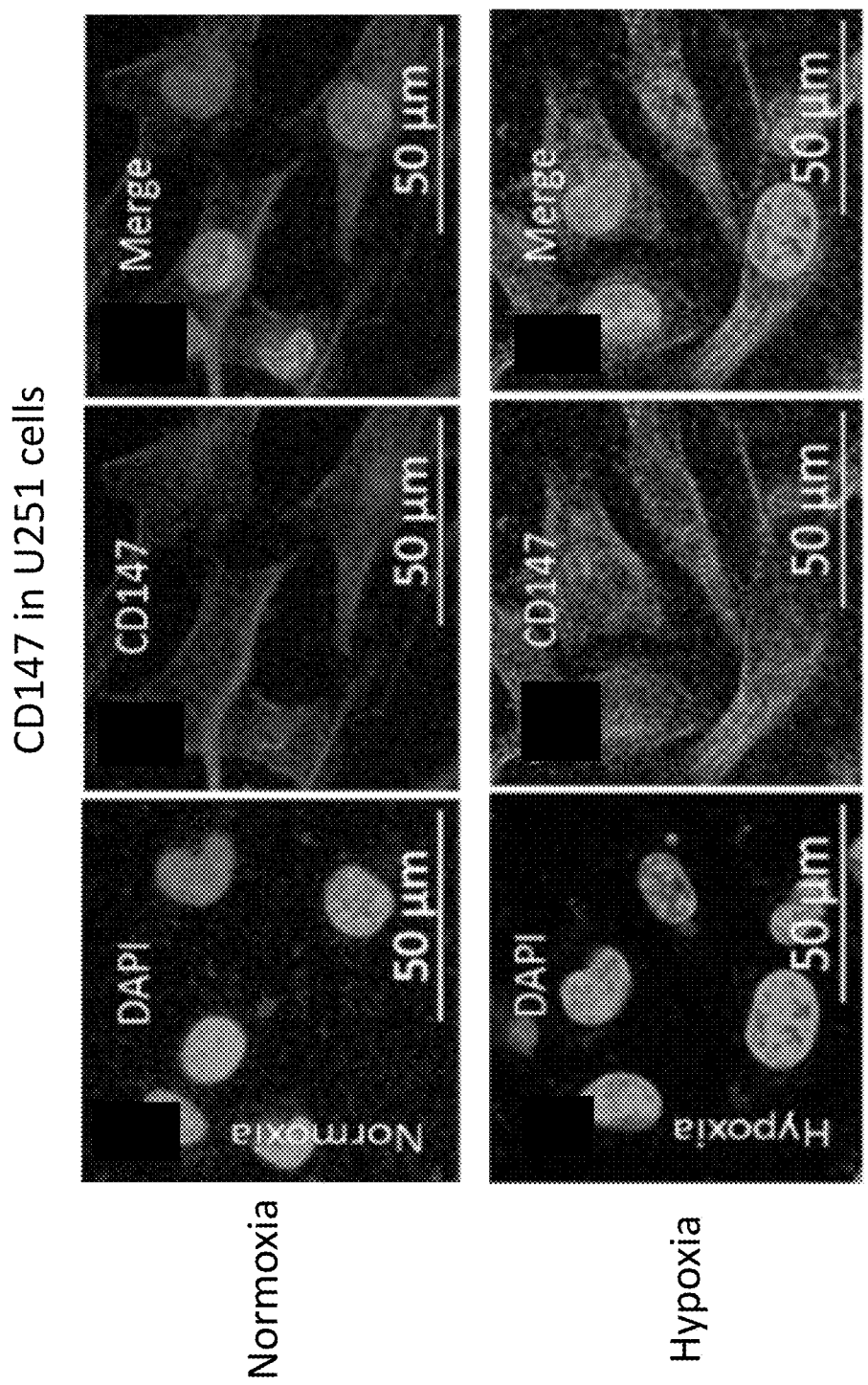
FIG. 8 shows the expression of CD147 in U251 cells under normoxia (upper panel) or hypoxia (lower panel) after immunofluorescent staining, in which the cells were treated with DAPI to locate the nucleus, and Alexa 488 to indicate the presence of CD147 in the cells.
Figure 9:
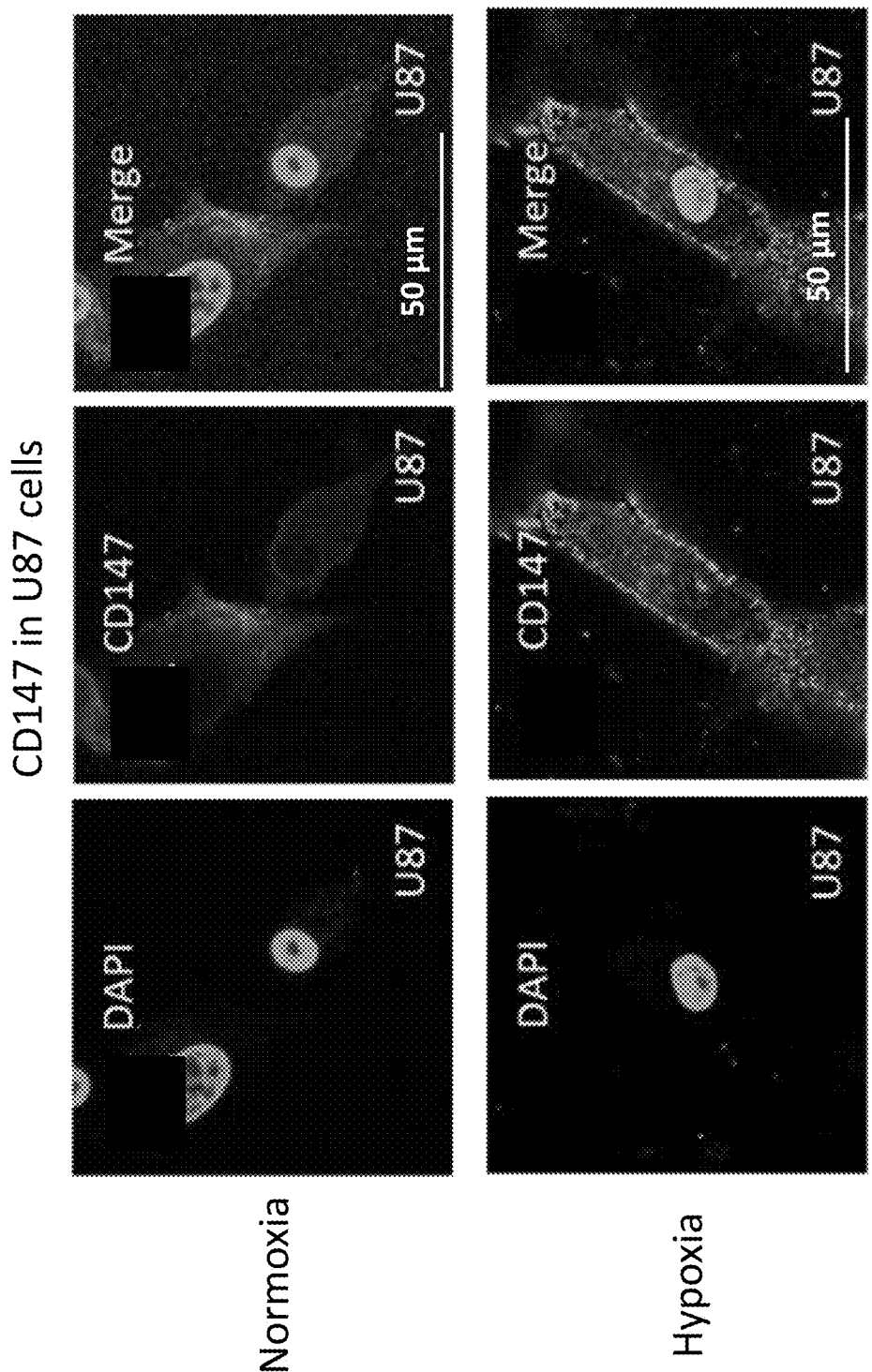
FIG. 9 shows the expression of CD147 in U87 cells under normoxia (upper panel) or hypoxia (lower panel) after immunofluorescent staining, in which the cells were treated with DAPI to locate the nucleus, and Alexa 488 to indicate the presence of CD147 in the cells.
Figure 10:
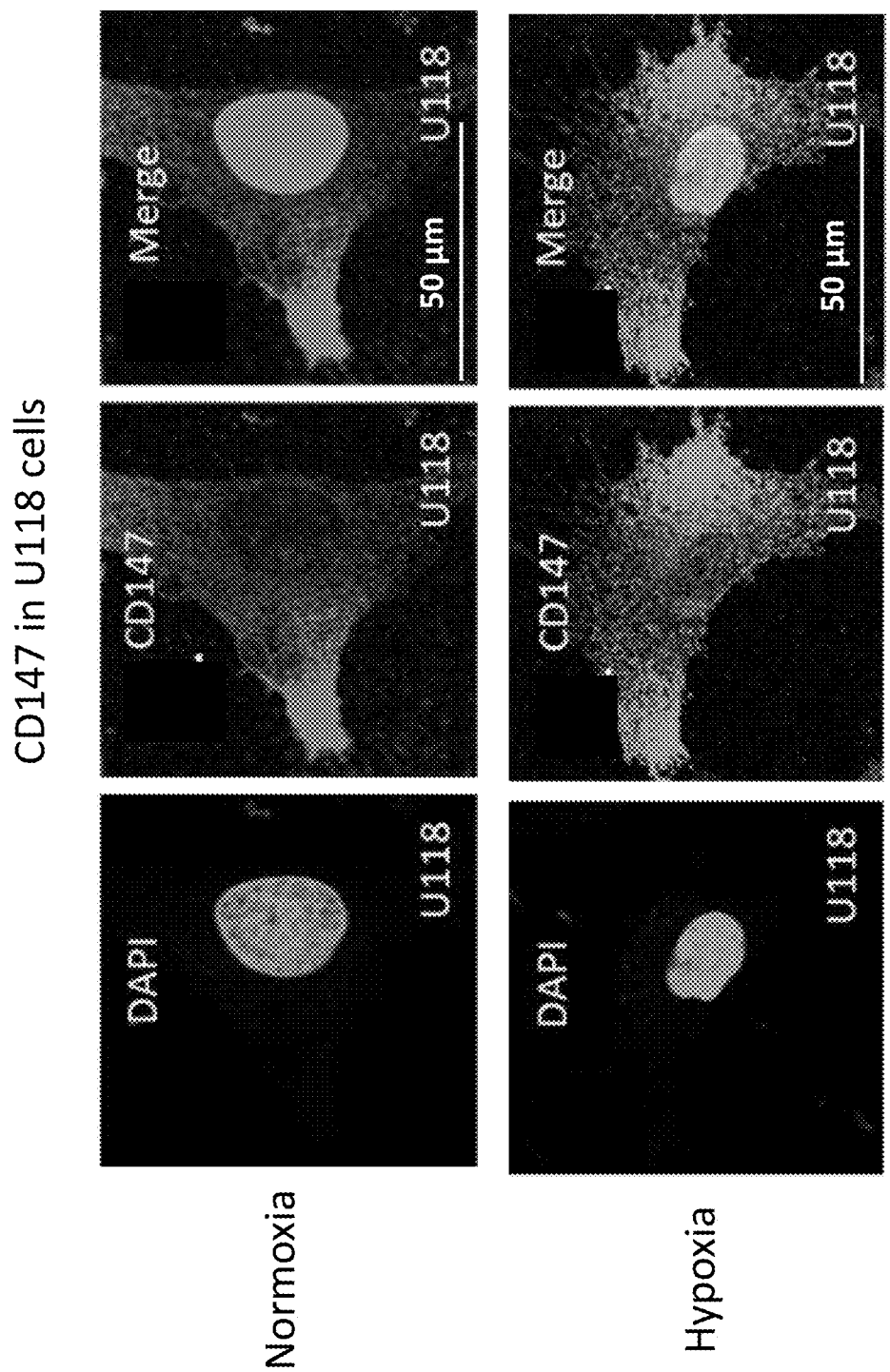
FIG. 10 shows the expression of CD147 in U118 cells under normoxia (upper panel) or hypoxia (lower panel) after immunofluorescent staining, in which the cells were treated with DAPI to locate the nucleus, and Alexa 488 to indicate the presence of CD147 in the cells.
Figure 11:
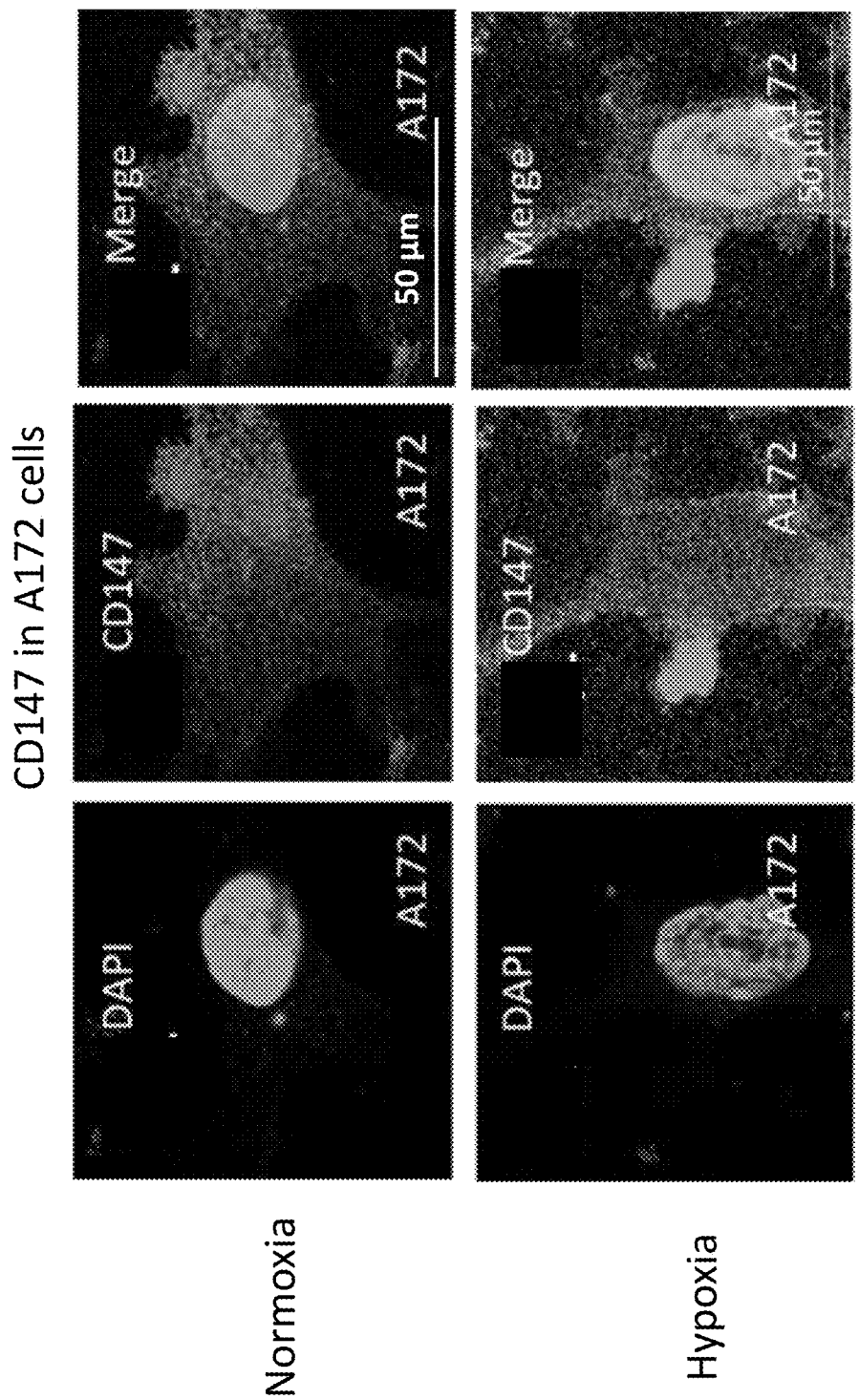
FIG. 11 shows the expression of CD147 in A172 cells under normoxia (upper panel) or hypoxia (lower panel) after immunofluorescent staining, in which the cells were treated with DAPI to locate the nucleus, and Alexa 488 to indicate the presence of CD147 in the cells.

FIG. 3 shows that the U251 cells being exposed to hypoxic chamber or $CoCl_2$, i.e. hypoxia group, had an increased HIF-1α expression and enhanced nuclear localization of HIF-1α. This result also confirms that the cells were in hypoxic environment.

FIGS. 4 to 7 show the presence of MCT1 in different cell lines including U251 cells, U87 cells, U118 cells, and A172 cells, under normoxic oxygen or hypoxic condition. These results further support that the level of MCT1 was significantly enhanced under hypoxia. Similarly, FIGS. 8 to 11 show the presence of CD147 in different cell lines under normoxic oxygen or hypoxic condition, and demonstrate a significant increase in CD147 level in the cells under hypoxia. Based on the results, it is thus demonstrated that hypoxia promotes MCT1 and CD147 expressions in GMs.

Example 2

Effect of MCT1 and CD147 on Migration and Proliferation of GMs

A further experiment was carried out to determine whether the enhanced expressions of MCT1 and CD147 have any effect on promoting the malignant progression of hypoxia-induced GMs particularly on migration and proliferation of GMs.

Figure 14B:
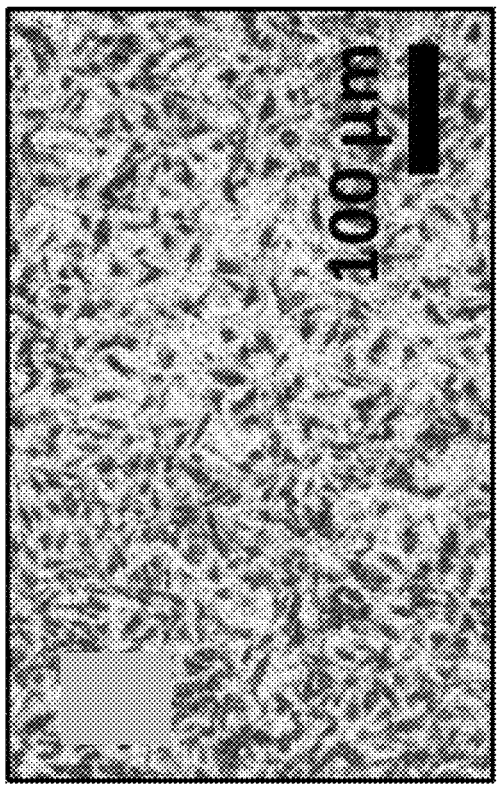
FIG. 14B is a microscopic image of migration of U251 cells under hypoxia as detected by transwell migration assay.
Figure 14A:
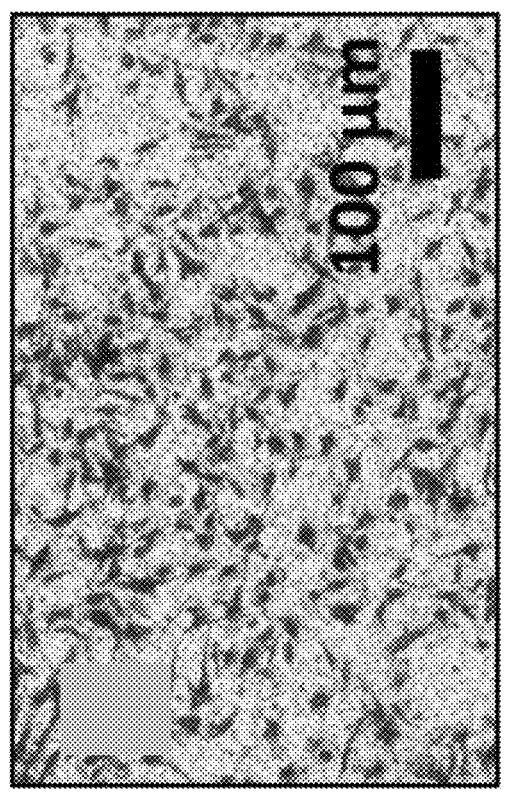
FIG. 14A is a microscopic image of migration of U251 cells under normoxia as detected by transwell migration assay.
Figure 14D:
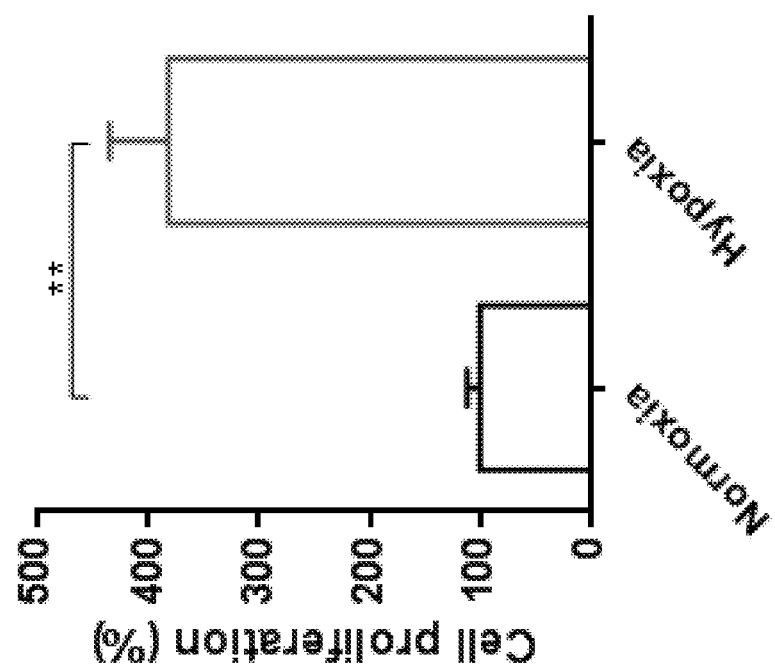
FIG. 14D is a plot showing the relative percentage of cell proliferation of U251 cells under hypoxia or normoxia.
Figure 14C:
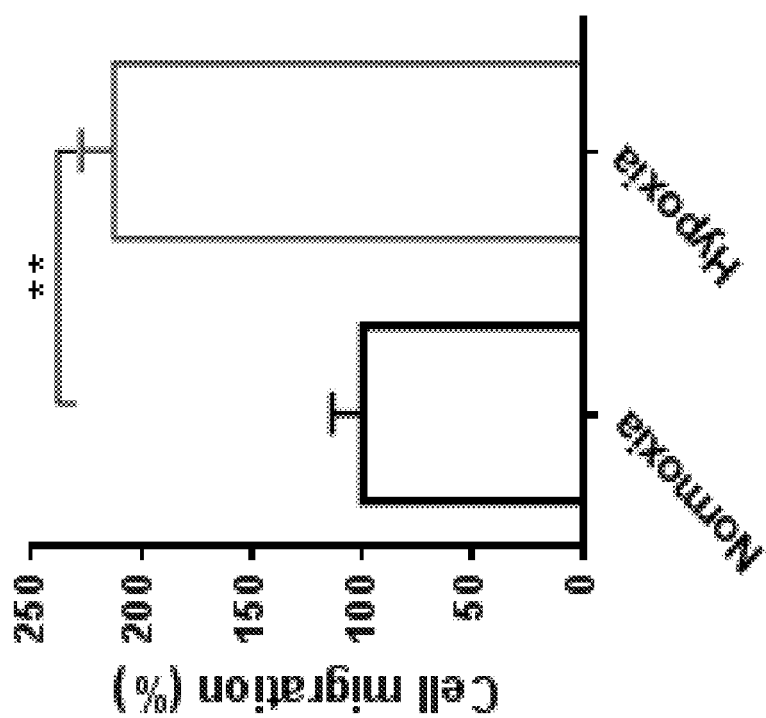
FIG. 14C is a plot showing the relative migration of U251 cells under hypoxia or normoxia, prepared by counting the number of migrated cells in the transwell assay.

To begin with, U251 cells were divided into two groups including normoxia group, and hypoxia group (induced with 1% oxygen). After incubation, the cells were subjected to transwell migration assay. FIGS. 14A and 14B are representative microscopic images of the cells' migration under normoxia or hypoxia for 24 hours. FIG. 14C is obtained by counting the number of migrated cells in the transwell assay (n=6 with Image) software). Relative migration (%) is expressed as the percent change relative to a respective control (100%).

The cell proliferation of U251 cells under hypoxia or normoxia was then detected by conducting MTT cell proliferation assay (n=6). The MTT cell proliferation assay was conducted based on standard protocol. FIG. 14D shows the results that U251 cells proliferated at a larger extent compared to the control group.

Based on the results in FIGS. 14A to 14D, it is demonstrated that GMs under hypoxia has a higher proliferation rate and migration rate.

The inventors then proceeded to determine the effect of MCT1 and its binding partner CD147 on the migration and proliferation, the transwell analysis and MTT assay were repeated with the following five groups of U251 cells:
- a control group with U251 cells;
- a MCT1 overexpression (MCT1 OE) group in which the U251 cells were induced to overexpress MCT1 gene;
- a MCT1 knockdown (MCT1 KD) group in which the U251 cells were treated to have a knockdown of MCT1 gene;
- a CD147 overexpression (CD147 OE) group in which the U251 cells were induced to overexpress CD147 gene; and
- a CD147 knockdown (CD147 KD) group in which the U251 cells were treated to have a knockdown of CD147 gene.

All these cells were separately treated and subjected to 24-hour incubation for transwell migration assay. The results are shown in FIGS. 15A to 15E. The scale bars in FIGS. 15A-15E represent 100 μm.

According to the results, MCT1 and its binding partner, CD147, play a crucial role in the hypoxia-induced malignant progression of U251 GMs.

Figure 15G:
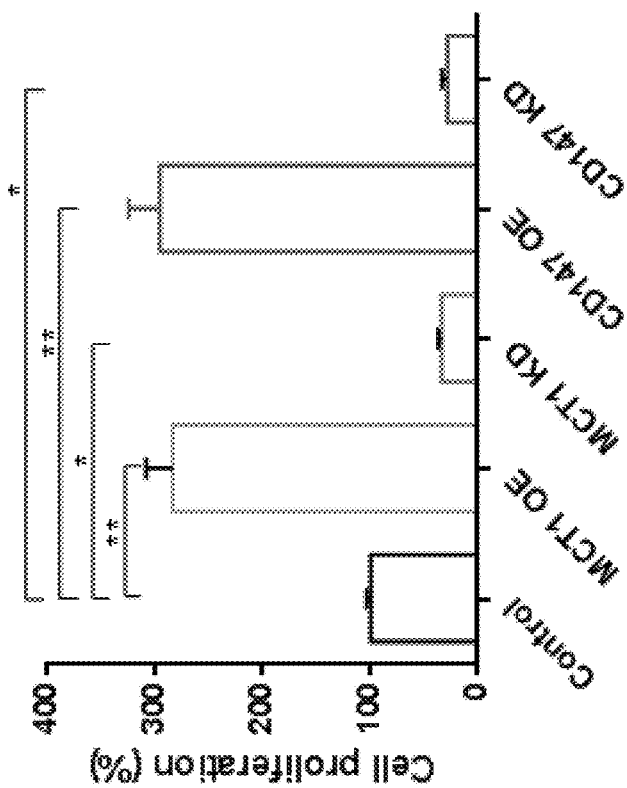
FIG. 15G is a plot showing the cell proliferation, in a quantitative manner, by comparing U251 cells' proliferation different groups, compared to control, via using MTT cell proliferation assay.
Figure 15F:
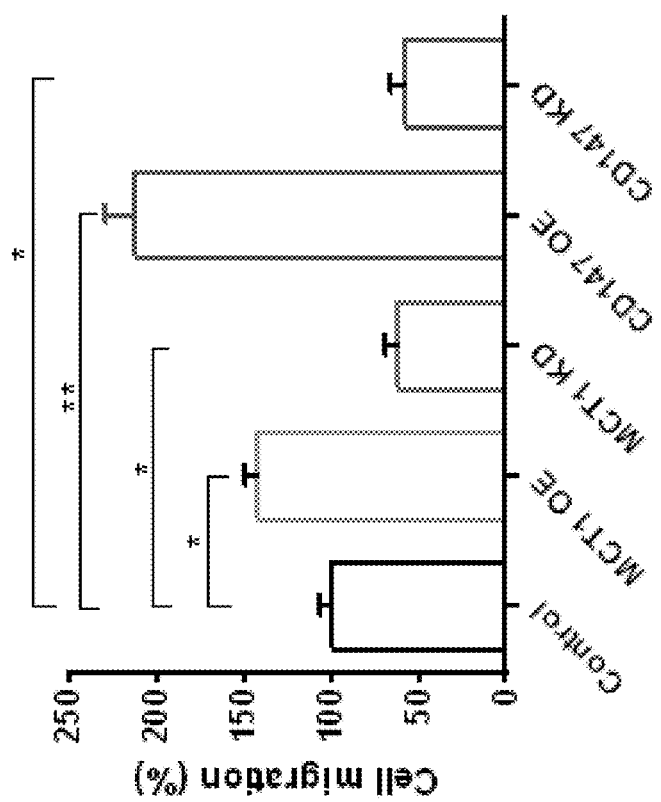
FIG. 15F is a plot showing the cell migration of U251 cells under different treatment, in a quantitative manner, based on the results obtained from transwell assay in FIG. 15A to FIG. 15E.

Also, FIG. 15F is the quantitative analysis of GMs' migration particularly the migration of U251 cells by counting the number of migrated cells in transwell assay (n=6 with Image) software). Relative GMs' migration (%) is expressed as the percent change relative to a respective control (100%). FIG. 15G is the comparative analysis of GMs' proliferation among MCT1 OE-, MCT1 KD-, CD147 OE-, and CD147 KD- induced GMs, compared to control, via using MTT cell proliferation assay (n=6).

Figure 16:
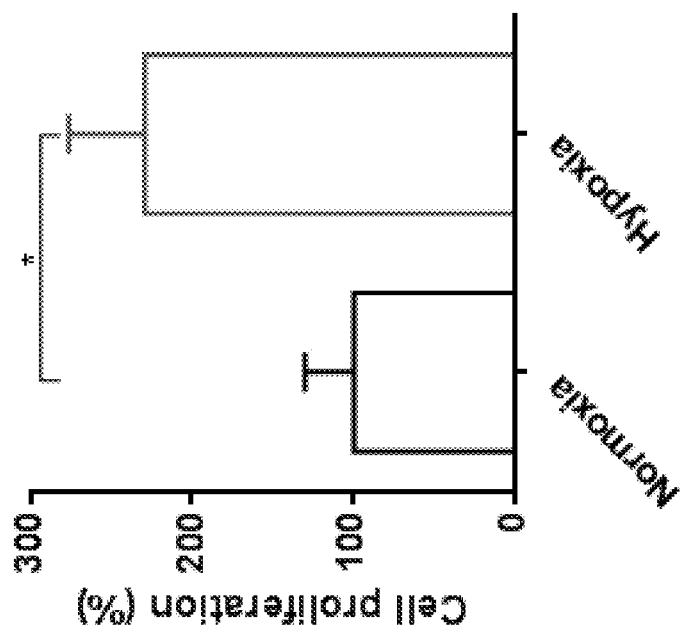
FIG. 16 is a plot showing the cell proliferation of the bromodeoxyuridine/5-bromo-2'-deoxyuridine (BrdU) cell proliferation assay for GMs under normoxia or hypoxia.

A bromodeoxyuridine/5-bromo-2'-deoxyuridine (BrdU) cell proliferation assay was conducted to determine the cell proliferation of GMs under normoxia or hypoxia. FIG. 16 shows the relative cell proliferation of the GMs (n=6) which is expressed as the percent change relative to a respective control (100%).

Data shown in FIGS. 15F-16 are presented as the mean±standard error of the mean (SEM) of 2 independent experiments. Significance level: **P<0.01, *P<0.05, hypoxia vs. normoxia. MCT1 OE-, MCT1 KD-, CD147 OE-, or CD147 KD- group vs. control.

Example 3

Effect of Hypoxia in Glycolytic Reprogramming

Figure 12:
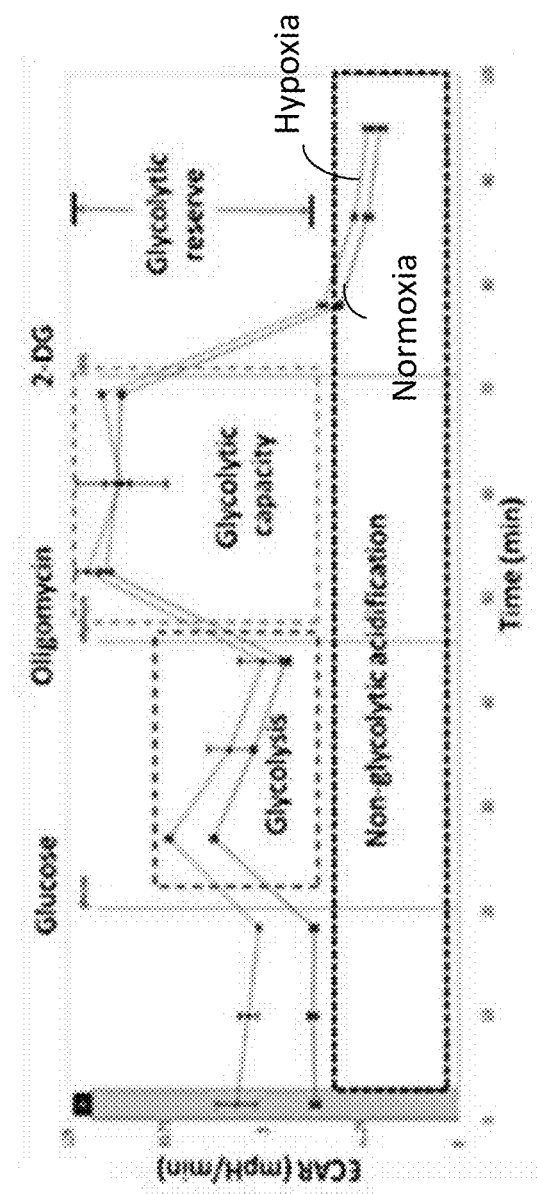
FIG. 12 is a representative graph demonstrating the extracellular acidification rate (ECAR) of normoxic and hypoxic U251 GMs and their response to glucose, oligomycin, and 2-DG in the measurement of the status of the glycolytic metabolism.
Figure 13:
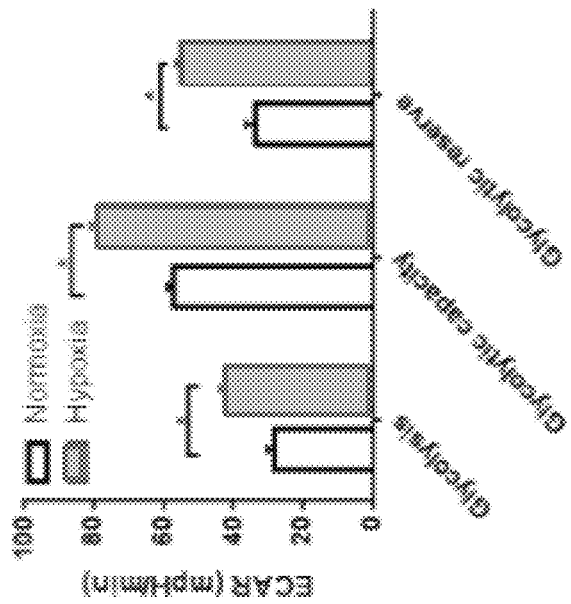
FIG. 13 is a plot showing the ECAR of the U251 cells in glycolysis, glycolytic capacity, and glycolytic reserve under normoxic and hypoxic condition respectively (n=3)

The inventors further determined the extracellular acidification rate (ECAR) of normoxic and hypoxic U251 cells respectively by using XF24-Extracellular Flux analyzer. FIG. 12 shows the ECAR of the cells in response to glucose, oligomycin, and 2-DG in the measurement of the status of the glycolytic metabolism. FIG. 13 is a plot prepared based on the detected rates, which shows that the cells generally had a higher rate in glycolysis, glycolytic capacity and glycolytic reserve when they were under hypoxic condition.

Accordingly, the GMs have enhanced glycolytic reprogramming activity under hypoxic condition. Glycolytic reprogramming of GMs is crucial for their survival in the hypoxic tumor microenvironment (TME). There are reports discussing that hypoxic GMs release tremendous numbers of exosomes, which might support their survival through the autologous or heterologous interactions with surrounding cells. Therefore, the next experiment was conducted to determine the effect of hypoxia in production and release of exosomes from GMs.

Example 4

Effect of Malignant Transition on Production and Release of Exosomes

To investigate the correlation between the malignant transition of hypoxic GMs and their production and release of exosomes, the secretion assay of exosomes was conducted via using nanoparticle tracking analysis (NTA). U251 cells were tested under normoxic or hypoxic condition.

FIGS. 17A and 17B show the size distribution and quantity of exosomes released from cultured normoxic and hypoxic GMs for 24 hours, as analyzed by NTA. FIG. 17C shows the enhanced release of exosomes from hypoxic GMs compared to normoxic GMs for 24 hours.

It is shown that as compared with normoxic U251 cells, hypoxic U251 cells released significantly higher number of exosomes (248.9%). In particular, it is believed that the enhanced MCT1 and CD147 in hypoxic U251 cells promote intracellular $Ca^{2+}$-dependent exosome release.

Figure 18C:
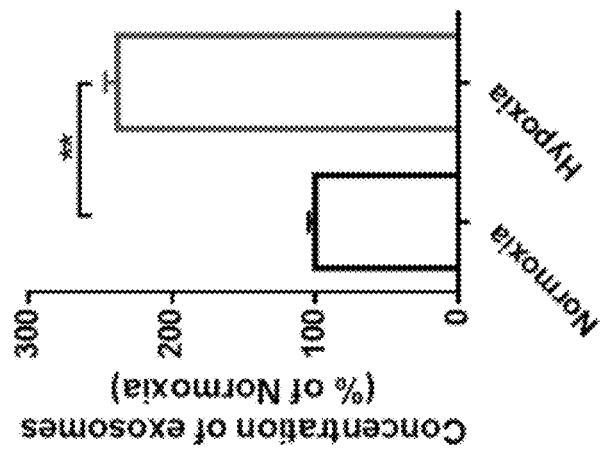
FIG. 18C is a plot showing the enhanced release of exosomes from A172 cells under hypoxia compared to normoxia, as detected by NTA.
Figure 18B:
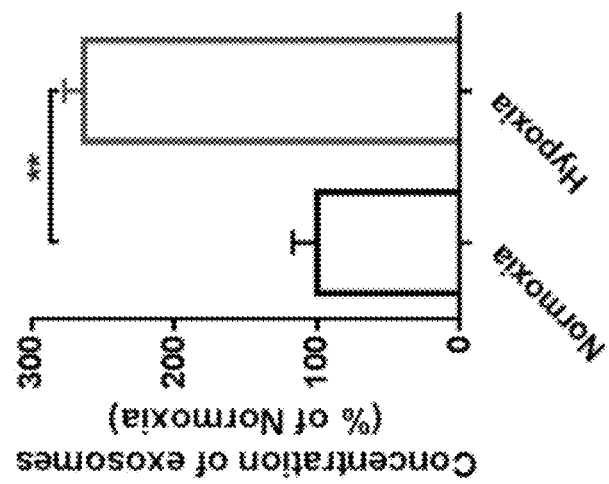
FIG. 18B is a plot showing the enhanced release of exosomes from U118 cells under hypoxia compared to normoxia, as detected by NTA.
Figure 18A:
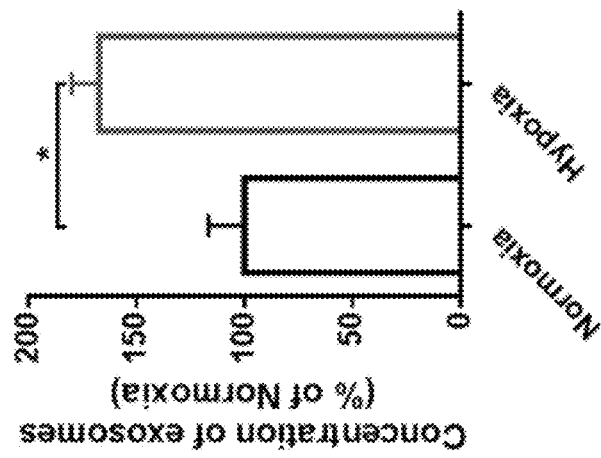
FIG. 18A is a plot showing the enhanced release of exosomes from U87 cells under hypoxia compared to normoxia, as detected by NTA.

FIGS. 18A-18C show the detection of exosome release and exosomal CD63, MCT1, and CD147 from different GMs under normoxic and hypoxic conditions. The tested GMs include U87 cells, U118 cells and A1721 cells. Specifically, the exosome release is enhanced in U87 cells, U118 cells, and A172 cells under hypoxia compared to normoxia, as detected by NTA (n=9). It is shown that enhanced exosome release (67.52%, 163.61%, and 138.16%) was also observed in hypoxic U87-, U118-, and A172- cells, respectively.

Example 5

Effect of Gain or Loss of MCT1 or CD147 Functions in Exosomes Release

To determine whether MCT1 and CD147 in GMs could be involved in regulating exosome release, the effect of gain or loss of MCT1 or CD147 functions in the release of exosomes from U251 cells was investigated.

Figure 19:
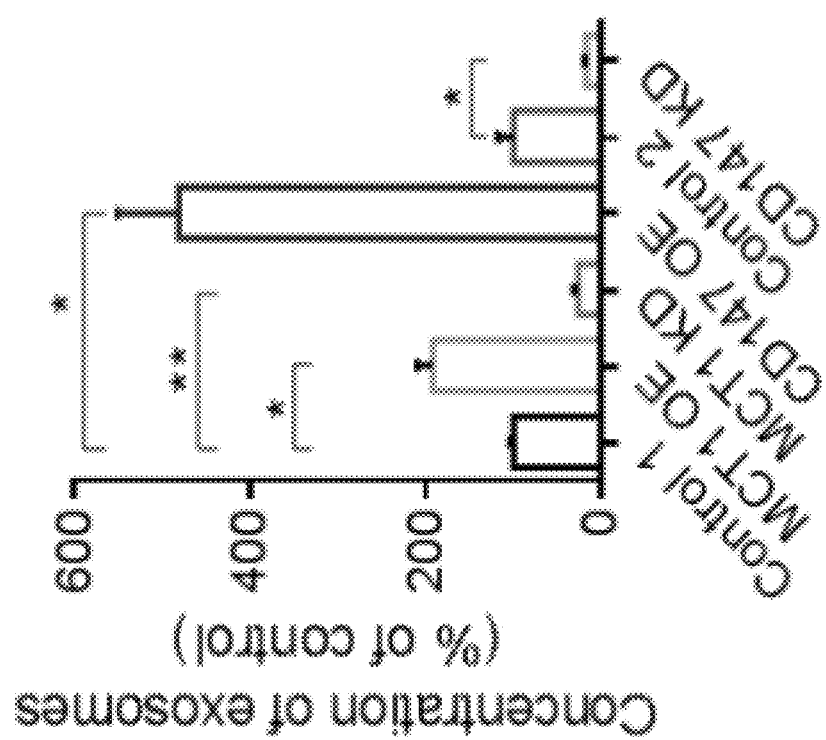
FIG. 19 is a plot showing the concentration of exosomes released from U251 cells with treated with empty backbone, MCT1 OE, MCT1 KD, CD147 OE, antisense oligonucleotides control and CD147 KD constructs.

FIG. 19 shows the results of the comparative analysis of exosome release from U251 cells treated with empty backbone (control 1 for lentivirus), MCT1 OE (lentivirus), MCT1 KD (lentivirus), CD147 OE (lentivirus), antisense oligonucleotides control (control 2) and CD147 KD (antisense oligonucleotides) constructs. The overexpression (OE) of MCT1 and CD147 in U251 cells dramatically increased exosome release (92.57% and 381.16%, respectively). In contrast, the KD of MCT1 or CD147 reduced exosome release from U251 cells by 73.84% and 82.49%, respectively, indicating the essential role of MCT1 and CD147 in controlling exosome release.

Examples 1-5 collectively demonstrate that MCT1 and CD147 control the release of exosomes from hypoxia induced malignant glioma cells.

Example 6

Effect of Hypoxia-Driven Enhanced Exosome Release on Change of Intracellular $Ca^{2+}$ Concentrations To further investigate whether the change of intracellular $Ca^{2+}$ concentrations could be associated with hypoxia-driven enhanced exosome release, Fluo Red™, AM $Ca^{2+}$ imaging and Fluo-4 AM $Ca^{2+}$ assay were conducted with normoxic- and hypoxic-U251 cells.

FIGS. 20A-20C are the representative images of Fura Red calcium dye-loaded hypoxic GMs compared to that of normoxic GMs, and BAPTA-AM (20 μM)-treated GMs. FIG. 20D is a graph showing the effect of increasing hypoxia with both intracellular $Ca^{2+}$ levels.

Taking FIGS. 17A-17C, 19, and 20A-20D into account, it is demonstrated that hypoxia increased both exosome release and intracellular $Ca^{2+}$ levels in U251 cells and, furthermore, chelating intracellular $Ca^{2+}$ with BAPTA-AM blocked the enhanced release of exosomes from U251 cells, suggesting the important role of intracellular $Ca^{2+}$ levels in exosome release.

Example 7

Effect of MCT1 and CD147 in Regulating Intracellular $Ca^{2+}$ Levels

To examine whether MCT1 and CD147 take part in the regulation of intracellular $Ca^{2+}$ levels in GMs under normoxia or hypoxia, Fluo Red™, AM $Ca^{2+}$ imaging was conducted with the normoxic- and hypoxic-U251 cells, in which MCT1 and CD147 were increased by expressing Lenti-CMVP-MCT1 cDNA-IRES-eGFP and Lenti-CMVP-CD147 cDNA-IRES-eGFP, and reduced by expressing Lenti-H1-MCT1shRNA-CMV-eGFP, or CD147 antisense LNA GapmeR.

FIGS. 21A-21D are the representative images of Fura Red calcium dye-loaded GMs with the induction of MCT1 OE or MCT1 KD (vs. control 1). FIGS. 22A-22D are the representative images of Fura Red calcium dye-loaded GMs with the induction of CD147 OE or CD147 KD (vs control 1 & 2).

The result showed that the OE of MCT1 or CD147 in GMs increased both intracellular $Ca^{2+}$ levels and exosome release with a strong correlation, whereas KD of MCT1 or CD147 in GMs reduced both intracellular $Ca^{2+}$ levels and exosome release with a strong correlation, indicating that MCT1 and CD147 in GMs could control exosome release in a calcium-dependent manner.

Figure 23B:
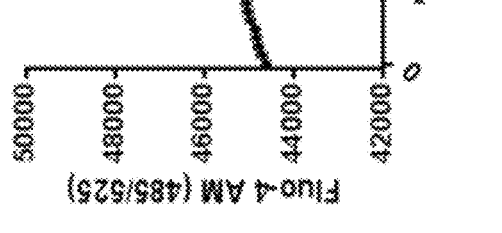
FIG. 23B is a plot showing the enhanced intracellular $Ca^{2+}$ level in GMs by the addition of sodium-L-lactate, followed by distinctive decline in intracellular $Ca^{2+}$ level by the application of BAPTA-AM.
Figure 23C:
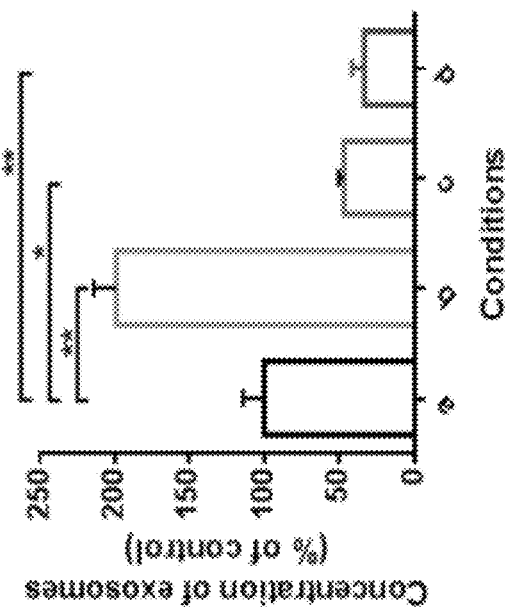
FIG. 23C is a plot showing the NTA exosome release assay from GMs exposed to four different conditions, in which a refers to GMs exposed to Exo-FBS medium, b refers to GMs exposed to sodium-L-lactate (20 mM), c refers to GMs exposed to BAPTA-AM, d refers to GMs exposed to BAPTA-AM with the pretreatment of sodium-L-lactate (20 mM)
Figure 23A:
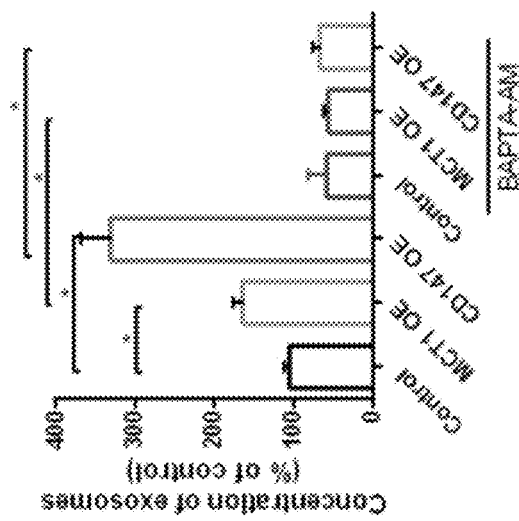
FIG. 23A is a plot showing the enhanced exosome release from GMs by the induction of MCT1 OE and CD147 OE, followed by marked decline in exosome release by the application of BAPTA-AM.

FIG. 23A shows the enhanced exosome release from GMs by the induction of MCT1 OE and CD147 OE compared to control, followed by marked decline in exosome release by the application of BAPTA-AM (20 μM, 100 μl) to the medium (2.1 ml), suggesting the association of MCT1 and CD147 in the enhanced release of exosomes from GMs through intracellular $Ca^{2+}$.

To recapitulate the hypoxia-induced acidic TME, sodium-L-lactates (20 mM) were applied to the culture medium of GMs. FIG. 23B shows the enhanced intracellular $Ca^{2+}$ level in GMs by the addition of sodium-L-lactate (20 mM, 100 μl) to the medium (2 ml), followed by distinctive decline in intracellular $Ca^{2+}$ level by the application of BAPTA-AM (20 μM, 100 μl) to the medium (2.1 ml). Interestingly, high level of extracellular lactates enhanced intracellular Ca2+ concentrations in GMs as determined by Fluo-4 AM $Ca^{2+}$ assay.

FIG. 23C shows the NTA exosome release assay conducted by exposing GMs to four different conditions for 10 min. Briefly, a represents Exo-FBS medium, b represents Sodium-L-lactate (20 mM), c represents BAPTA-AM, d represents BAPTA-AM with the pretreatment of Sodium-L-lactate (20 mM). All chemicals were dissolved in the Exo-FBS medium containing 1% DMSO. All data were shown as the mean±SEM. Significance level: **P<0.01, *P<0.05, hypoxia vs. normoxia, No-treatment vs. BAPTA-AM, MCT1 KD virus vs. Empty backbone virus (control 1), CD147 antisense vs. antisense control (control 2).

It is shown that increased intracellular $Ca^{2+}$ levels further stimulated exosome release which was blocked by BAPTA-AM, demonstrating that accumulated lactates in TME could promote exosome release in a calcium-dependent manner, mimicking the mechanism of hypoxia-induced enhanced exosome release in TME.

Examples 6 and 7 collectively demonstrate that hypoxia- and lactates-induced enhanced exosome release is controlled by MCT and CD147 in a calcium-dependent manner.

Example 8

Characterization of MCT1 and CD147 in Hypoxic GMs-Derived Exosomes

Exosomes from normoxic and hypoxic U251 cells were further characterized by NTA and transmission electron microscopy (TEM) analysis.

Figures 24A, 24B:
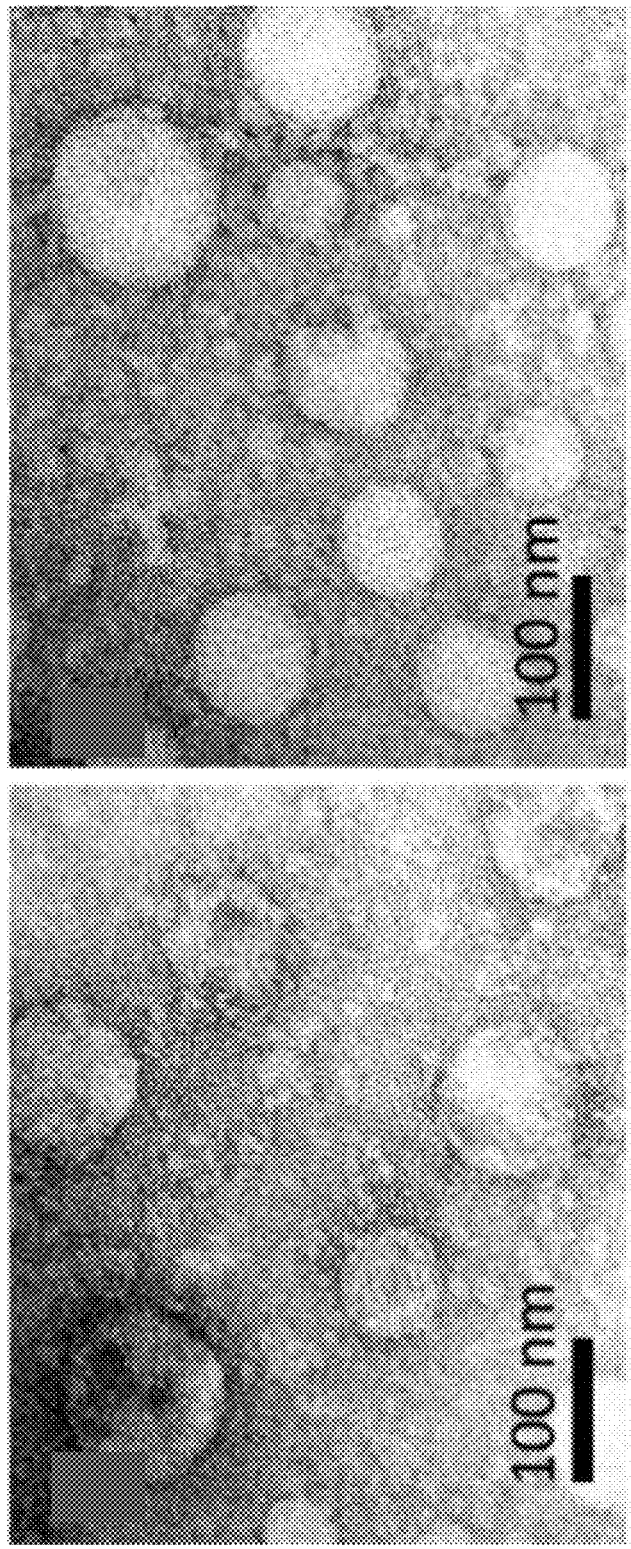
FIG. 24A is a transmission electron microscopy (TEM) image of exosomes derived from normoxic GMs.
FIG. 24B is a TEM image of exosomes derived from hypoxic GMs.
Figures 25A, 25B:
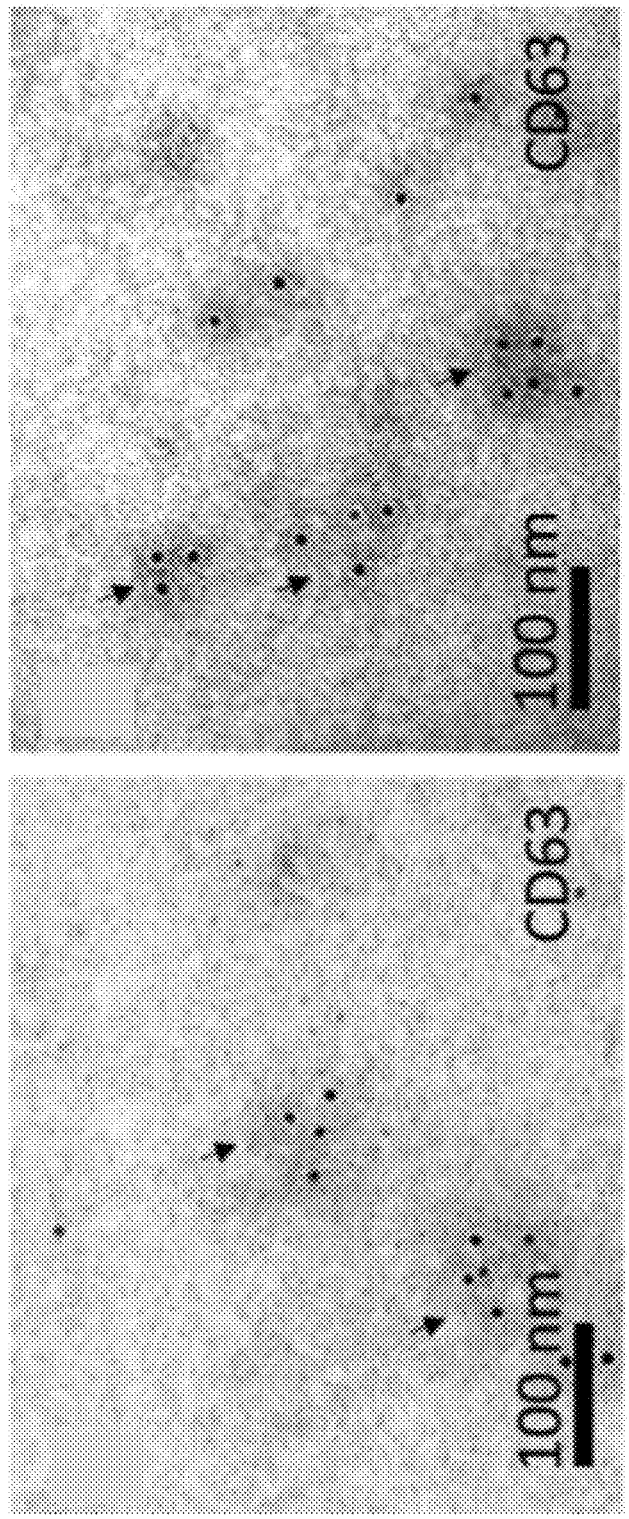
FIG. 25A is an immunogold electron microscopy (EM) image of CD63 in exosomes from normoxic GMs.
FIG. 25B is an immunogold EM image of CD63 in exosomes from hypoxic GMs.
Figure 25D:
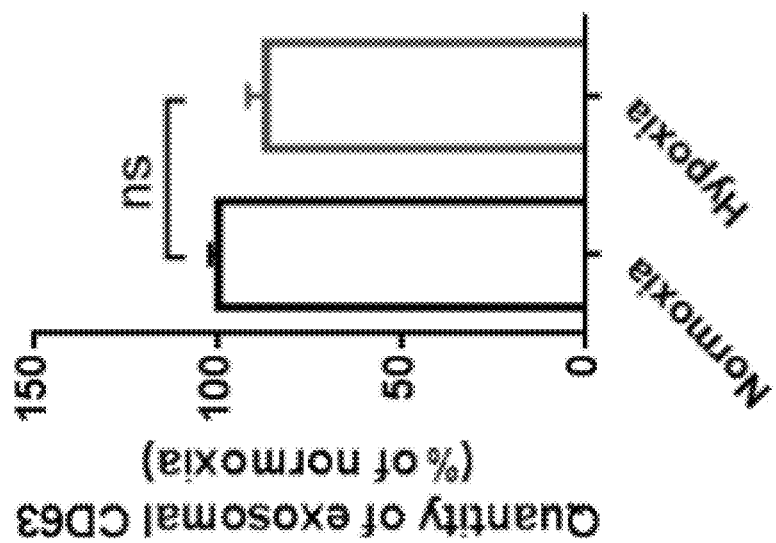
FIG. 25D is a plot showing the relative quantity of CD63 in exosomes from normoxic and hypoxic GMs as detected by enzyme-linked immunosorbent assay (ELISA)
Figure 25C:
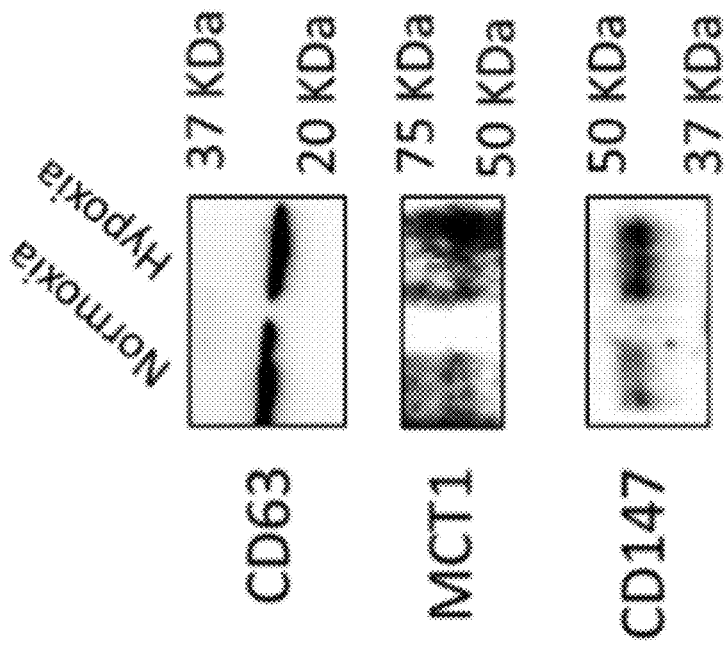
FIG. 25C is a Western Blot (WB) pattern showing the quantity of MCT1, CD147, and CD63 in exosomes from normoxic and hypoxic GMs.
Figures 28C, 28D:
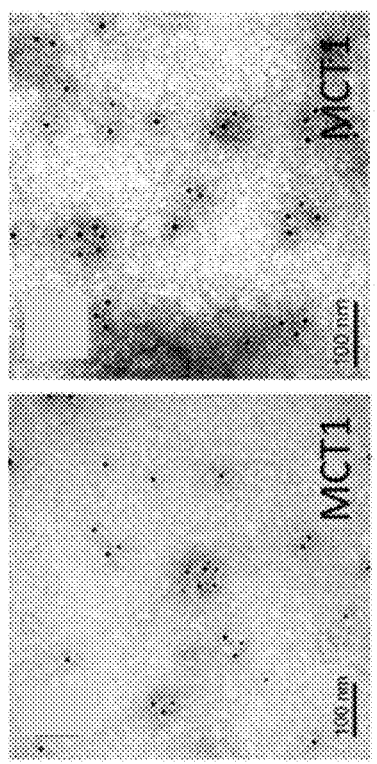
FIG. 28C is an immunogold EM micrograph of MCT1 in exosomes derived from normoxic U118 cells.
FIG. 28D is an immunogold EM micrograph of MCT1 in exosomes derived from hypoxia U118 cells.
Figures 28A, 28B:
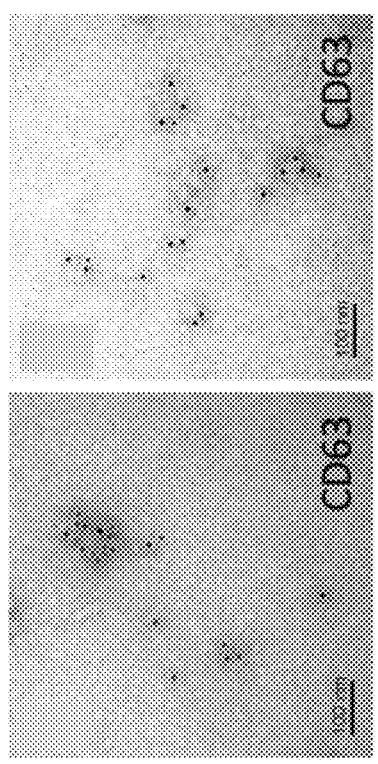
FIG. 28A is an immunogold EM micrograph of CD63 in exosomes derived from normoxic U118 cells.
FIG. 28B is an immunogold EM micrograph of CD63 in exosomes derived from hypoxia U118 cells.
Figure 28E:
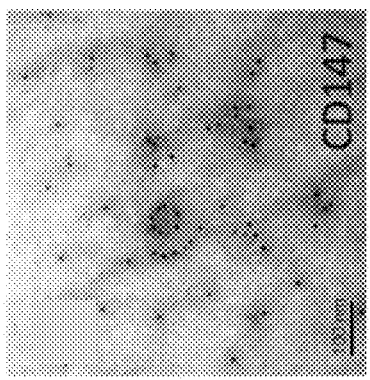
FIG. 28E is an immunogold EM micrograph of CD147 in exosomes derived from normoxic U118 cells.
Figure 28F:
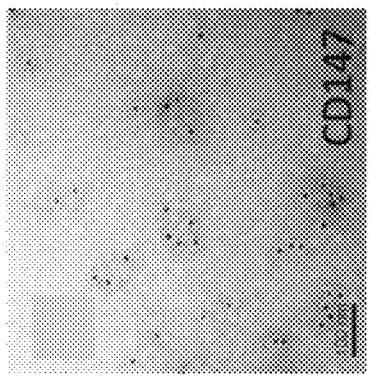
FIG. 28F is an immunogold EM micrograph of CD147 in exosomes derived from hypoxia U118 cells.

Referring back to FIGS. 17A and 17B as well as FIGS. 24A and 24B, both exosomes from normoxic and hypoxic GMs were mainly round-shaped nanoparticles with 30-200 nm in size as determined by NTA and TEM analysis. The size of hypoxic GMs-derived exosomes was relatively smaller than that of normoxic GMs-derived exosomes, indicating the potential impact of hypoxia on their size through the change of the biophysical property of exosome membrane With reference to FIGS. 25A and 25B, most GMs-derived exosomes were positive in the analysis with immunogold electron microscopy (EM) for CD63, a major exosome marker. The scale bar in FIGS. 25A and 25B represent 100 nm. FIG. 25C is a Western Blot (WB) for determination of the quantity of MCT1, CD147, and CD63 in exosomes from normoxic and hypoxic GMs, ensuring the reliability of techniques employed in their isolation and characterization. FIG. 25D is a graph showing the relative quantity of CD63 in exosomes from normoxic and hypoxic GMs (n=4) as detected by enzyme-linked immunosorbent assay (ELISA).

Example 9

Presence of MCT1 and CD147 in GMs-Derived Exosome Membrane

MCT1 and CD147, enhanced dramatically in malignant GMs, are enriched in the plasma membrane, thus, enabling them to incorporate into the membrane of daughter exosomes. Therefore, to determine whether MCT1 and CD147 were significantly present in the membrane of GMs-derived exosomes, immunogold EM analysis was conducted.

With reference to FIGS. 26A-29F, both MCT1 and CD147 were clearly present in the membrane of exosomes from all GMs cell lines tested, including U251, U87, U118, and A172 cell lines. The scale bars in FIGS. 26A-29F represent 100 nm. All data were expressed as the mean±SEM. Significance level: **P<0.01, *P<0.05, hypoxia vs. normoxia.

Example 10

Amount of MCT1 and CD147 in Parent GMs and Daughter Exosomes

Quantitative analysis was conducted with normoxic and hypoxic GMs-derived exosomes to determine whether exosomal MCT1 and CD147 could reflect their quantity in parent GMs.

Figure 30B:
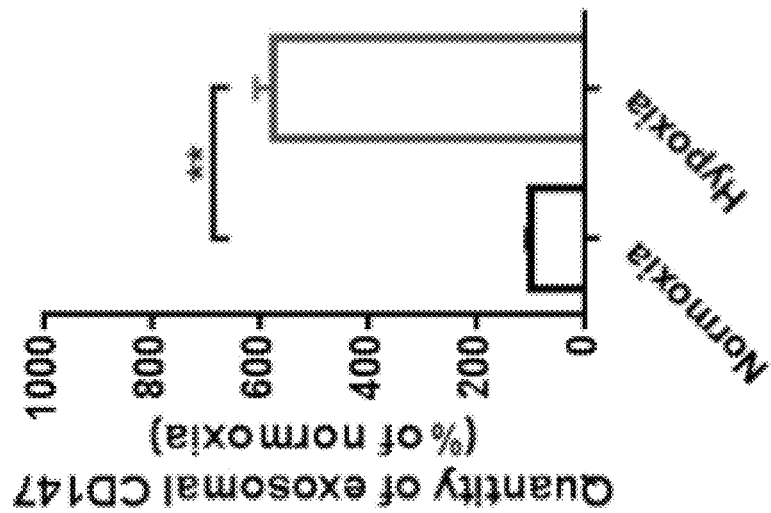
FIG. 30B is a graph showing the relative quantity of CD147 in exosomes from normoxic and hypoxic GMs as detected by ELISA.
Figure 30A:
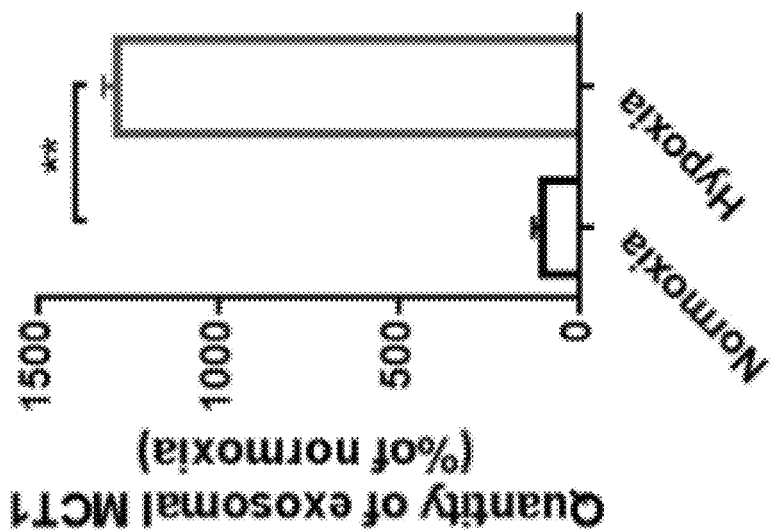
FIG. 30A is a plot showing the relative quantity of MCT1 in exosomes from normoxic and hypoxic GMs as detected by enzyme-linked immunosorbent assay (ELISA)

FIGS. 30A and 30B show the relative quantity of MCT1, and CD147 in exosomes from normoxic and hypoxic GMs (n=4) as detected by ELISA. All data were shown as the mean±SEM. Significance level: **$P<0.01$, *$P<0.05$, ns=not significant, hypoxia vs. normoxia.

Figure 31:
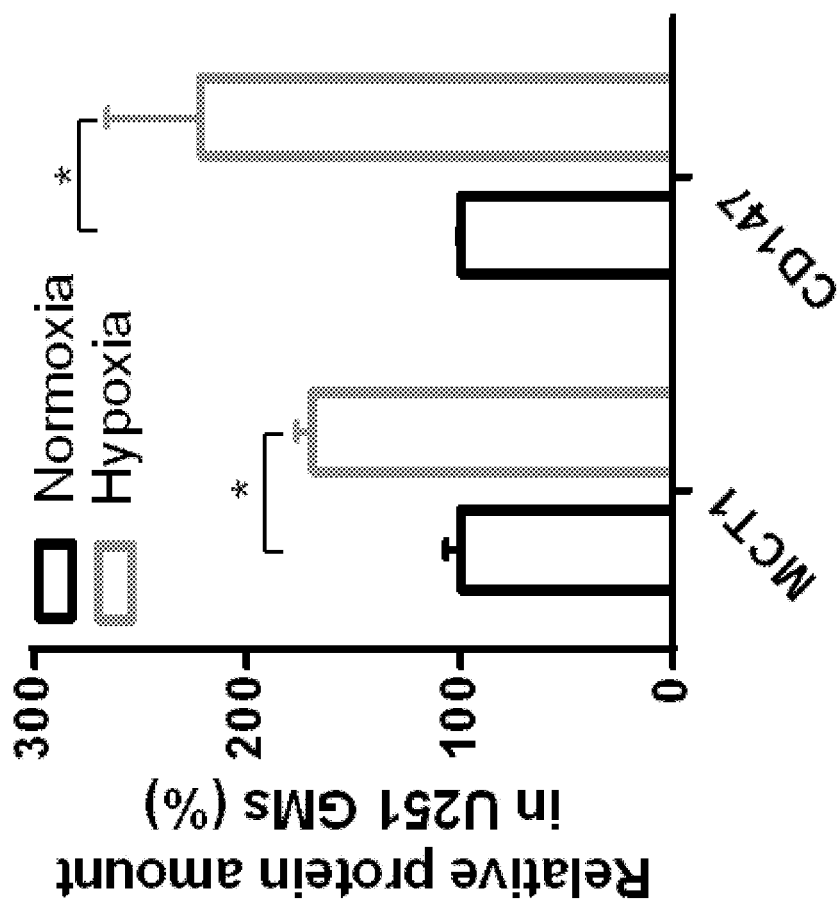
FIG. 31 is a graph showing the relative MCT1 and CD147 levels in U251 cells under normoxia and hypoxia, as detected by ELISA.

FIG. 31 shows the relative MCT1 and CD147 levels in U251 cells under normoxia and hypoxia, as detected by ELISA.

With reference to FIGS. 3A-11F, and 27A-31, the relatively enriched MCT1 and CD147 in hypoxic GMs and their daughter exosomes were demonstrated by immunogold EM, WB, and ELISA. A higher amount of membrane MCT1 and CD147 of hypoxic GMs-derived exosomes was further identified by Fluorescence-Activated Vesicle Sorting (FAVS) via using flow cytometry (data not shown), although its detection sensitivity was very weak. Importantly, MCT1 and CD147 levels in parent U251 cells, which were upregulated by their malignant progression, were closely correlated with those levels in daughter exosomes, revealing that exosomal MCT1 and CD147 could be faithful surrogate markers to monitor tumor progression. Particularly, in the validation experiments, the OE of MCT1 and CD147 in parent U251 GMs increased their level in daughter exosomes.

Figures 32A, 32B:
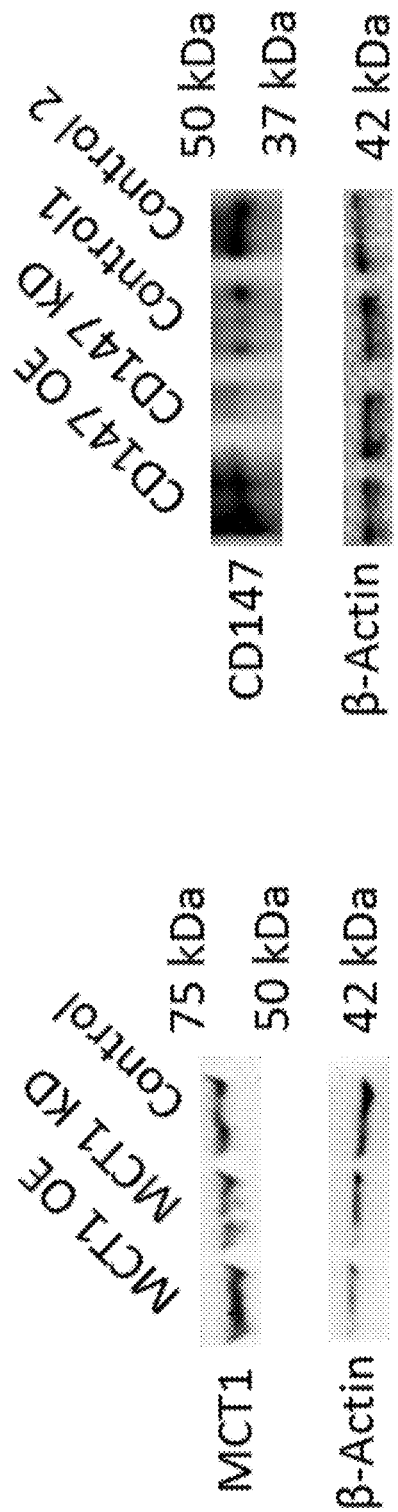
FIG. 32A is a Western Blot (WB) pattern showing the MCT1 level in U251 cells with treatment of MCT1 OE-, MCT1 KD-, or empty backbone-lentivirus.
FIG. 32B is a Western Blot (WB) pattern showing the CD147 level in U251 cells with treatment of CD147 OE, lentivirus control, CD147 KD, antisense control.

FIG. 32A shows the MCT1 level in U251 cells with treatment of MCT1 OE-, MCT1 KD-, or empty backbone-lentivirus (control) for 24 hours, as determined by WB. FIG. 32B shows the CD147 level in U251 cells with treatment of CD147 OE, control 1 (lentivirus control), CD147 KD (antisense LNA GapmeR), or control (antisense control) for 24 hours, as determined by WB. It is shown that the KD of MCT1 and CD147 in parent U251 cells reduced their level in daughter exosomes.

Figure 33B:
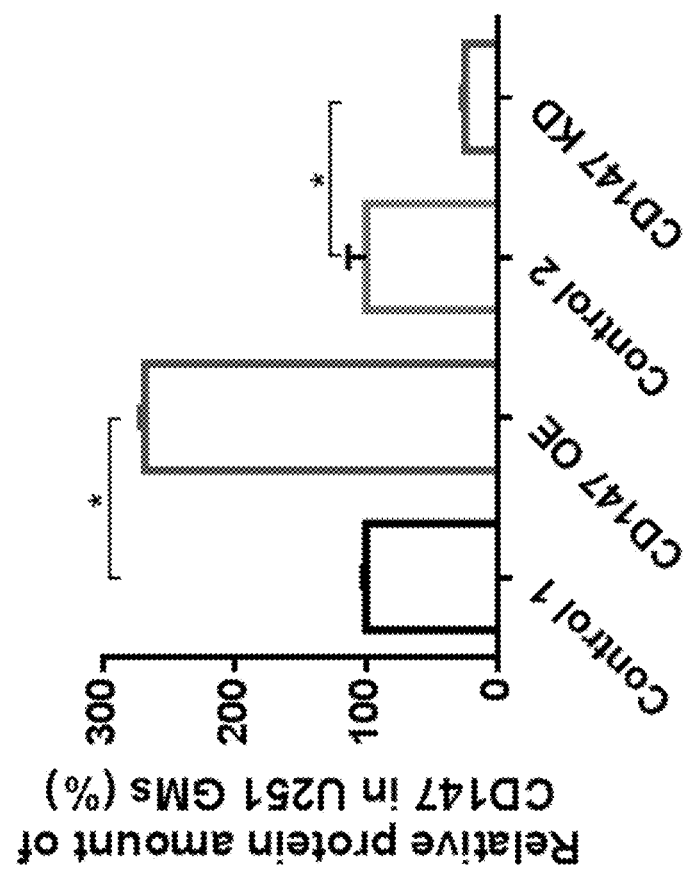
FIG. 33B is a plot showing the relative CD147 levels in the U251 GMs with the induction of MCT1 OE, MCT1 KD, CD147 OE, CD147 KD, and respective controls, as detected by ELISA.
Figure 33A:
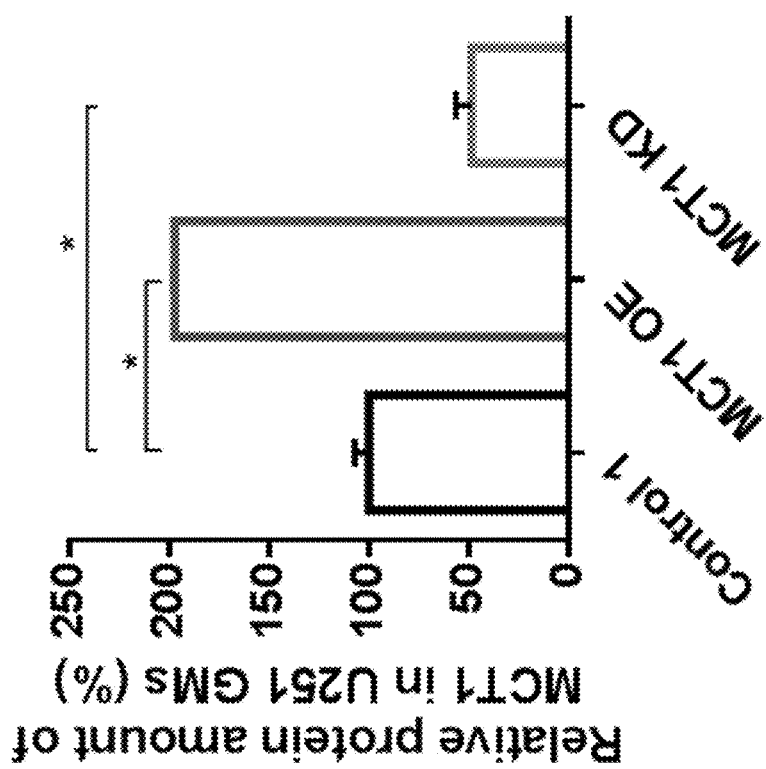
FIG. 33A is a plot showing the relative MCT1 levels in the U251 cells with the induction of MCT1 OE, MCT1 KD, CD147 OE, CD147 KD, and respective controls, as detected by ELISA.
Figure 33D:
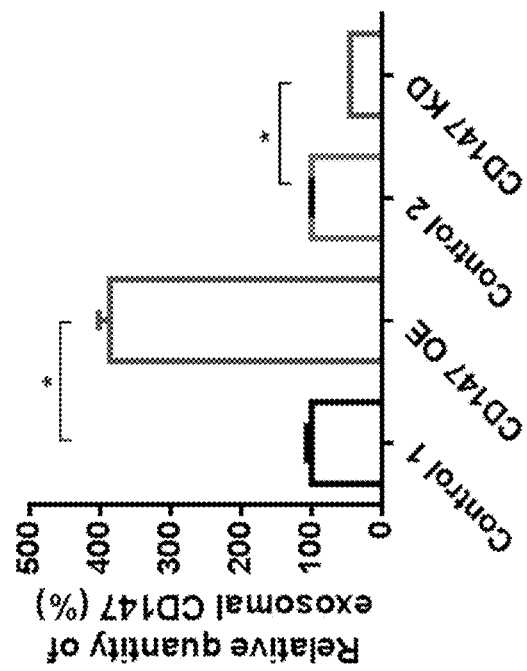
FIG. 33D is a plot showing the relative CD147 levels in the exosomes derived from the U251 cells with the induction of MCT1 OE, MCT1 KD, CD147 OE, CD147 KD, and respective controls, as detected by ELISA.
Figure 33C:
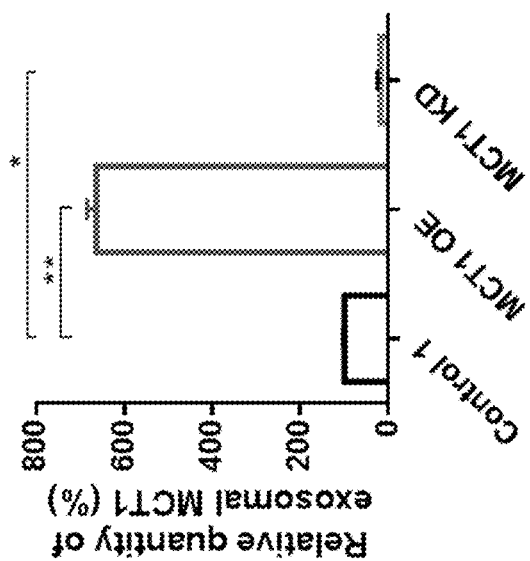
FIG. 33C is a plot showing the relative MCT1 levels in the exosomes derived from the U251 cells with the induction of MCT1 OE, MCT1 KD, CD147 OE, CD147 KD, and respective controls, as detected by ELISA.
Figure 34B:
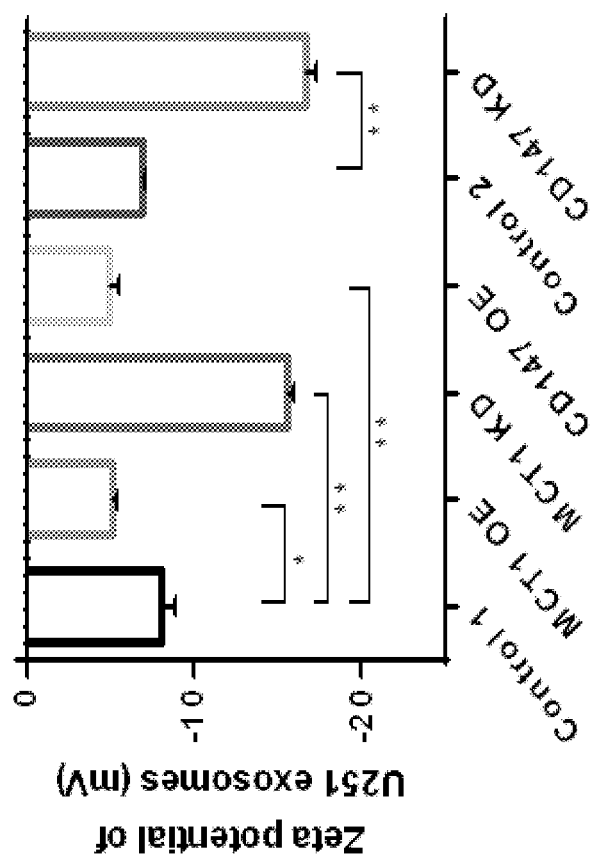
FIG. 34B is a plot showing the Zeta potential of exosomes derived from U251 cells with the induction of MCT1 OE, MCT1 KD, CD147 OE, and CD147 KD respectively.
Figure 34A:
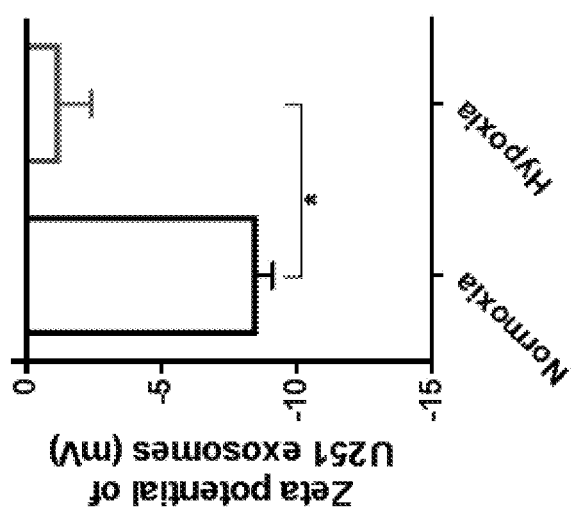
FIG. 34A is a plot showing the Zeta potential of exosomes derived from normoxic and hypoxic U251 cells.
Figure 35B:
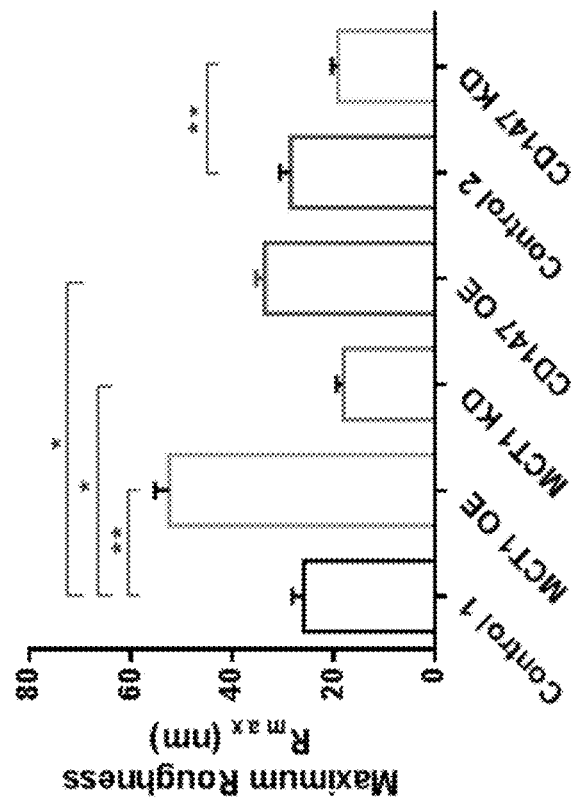
FIG. 35B is a plot showing the maximum roughness of exosomes derived from U251 cells with the induction of MCT1 OE, MCT1 KD, CD147 OE, and CD147 KD respectively.
Figure 35A:
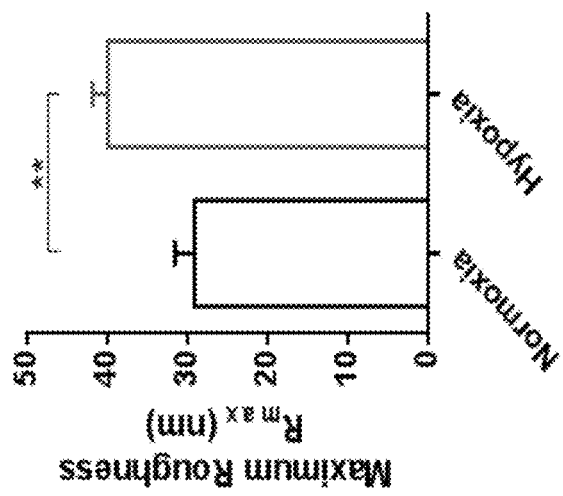
FIG. 35A is a plot showing the maximum roughness of exosomes derived from normoxic and hypoxic U251 cells.
Figure 36B:
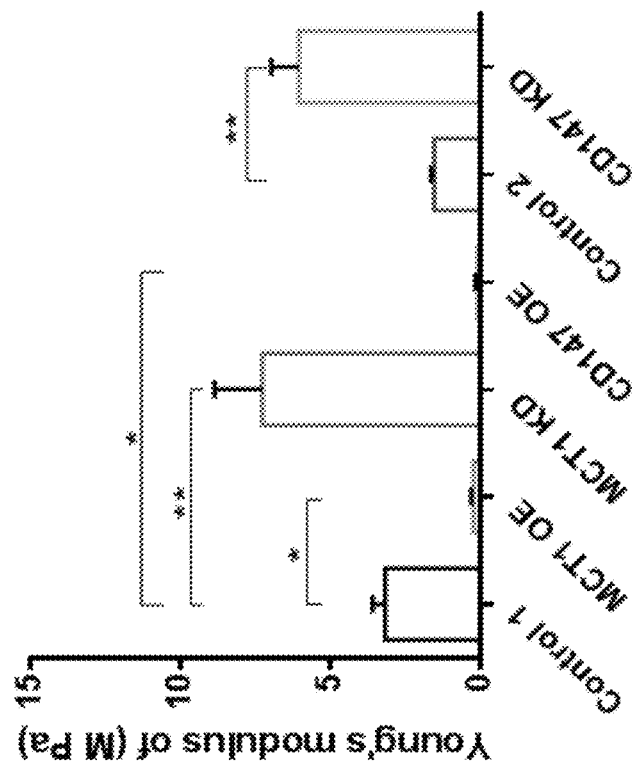
FIG. 36B is a plot showing the stiffness (Young's modulus) of exosomes derived from U251 cells with the induction of MCT1 OE, MCT1 KD, CD147 OE, and CD147 KD respectively.
Figure 36A:
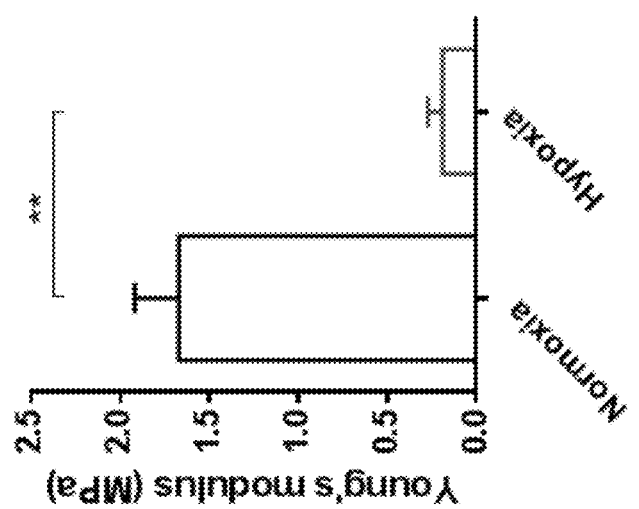
FIG. 36A is a plot showing the stiffness (Young's modulus) of exosomes derived from normoxic and hypoxic U251 cells.
Figure 37B:
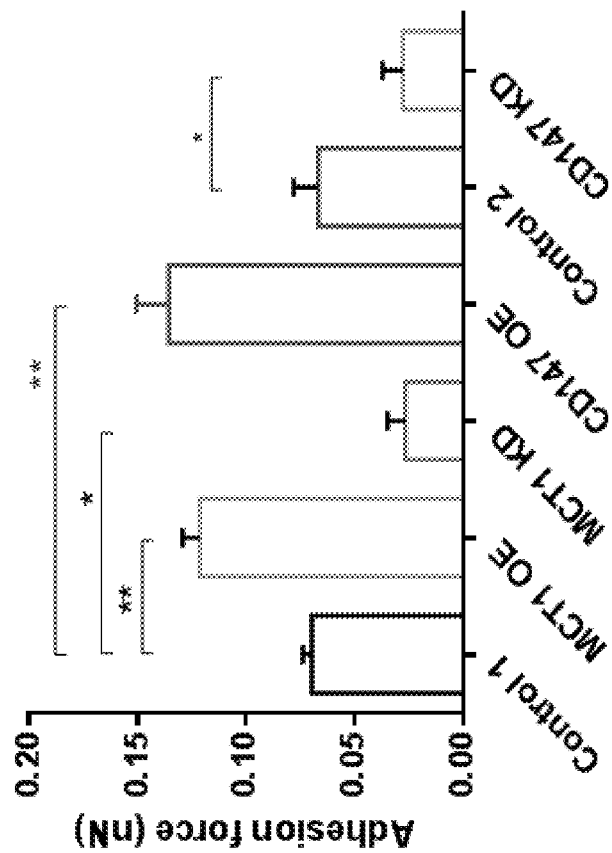
FIG. 37B is a plot showing the adhesion force of exosomes derived from U251 cells with the induction of MCT1 OE, MCT1 KD, CD147 OE, and CD147 KD respectively.
Figure 37A:
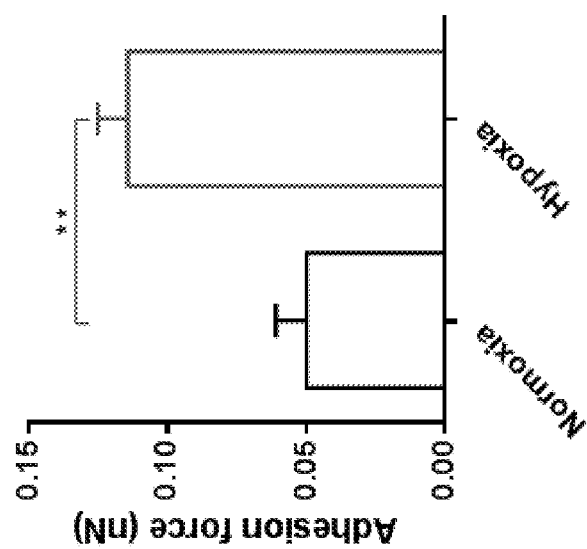
FIG. 37A is a plot showing the adhesion force of exosomes derived from normoxic and hypoxic U251 cells.

FIGS. 33A and 33B show the relative MCT1 and CD147 levels in the U251 cells with the induction of MCT1 OE, MCT1 KD, CD147 OE, CD147 KD, and respective controls, as detected by ELISA. FIGS. 33C and 33D show the relative MCT1 and CD147 levels in the exosomes derived from the U251 cells with the induction of MCT1 OE, MCT1 KD, CD147 OE, CD147 KD, and respective controls, as detected by ELISA. Significance level: **$P<0.01$, *$P<0.05$, hypoxia vs. normoxia, MCT1 OE or MCT1 KD group vs. control 1, CD147 OE and CD147 KD group vs. control 1 and 2, respectively.

FIGS. 39A-39H show the immunofluorescent staining of MCT1 in GMs which were treated with empty backbone-lentivirus (control 1) and MCT1 OE lentivirus for 24 hours, as determined immunocytochemistry (ICC). FIG. 40A-40H show the immunofluorescent staining for CD147 in GMs with treatment with antisense oligonucleotides control (control 2) and CD147 OE antisense oligonucleotides for 24 hours, as determined ICC. All data were shown as the mean±SEM. Significance level: **$P<0.01$, *$P<0.05$, hypoxia vs. normoxia. The scale bar represents 50 μm.

As a result, increasing MCT1 or CD147 in parent GMs enhanced MCT1 or CD147 in their daughter exosomes. In the same way, referring to FIGS. 33C and 33D, decreasing MCT1 or CD147 in parent GMs directly reduced MCT1 or CD147, respectively, in their daughter exosomes.

Examples 8-10 collectively demonstrate that hypoxic GMs-derived exosomes contain higher amount of MCT1 and CD147.

Example 11

Effect of MCT1 OE and MCT1 KD on Biophysical Properties

FIGS. 34A-37B show the Zeta potential, roughness, stiffness (Young's modulus), and adhesion force of exosomes derived from normoxic and hypoxic U251 GMs as well as U251 GMs with the induction of MCT1 OE, MCT1 KD, CD147 OE, and CD147 KD (as compared to a relevant control: control 1 for lentivirus; control 2 for antisense oligonucleotide). All data were expressed as the mean±SEM (N=4), Significance level: **$P<0.01$, *$P<0.05$, hypoxia vs. normoxia, MCT1 OE-, MCT1 KD-, or CD147 OE- group vs. control 1. CD147 KD group vs. control 2.

Example 12

Effect of Hypoxic GMs-Derived Exosomes on Uptake into ECs and Angiogenesis

Figure 38B:
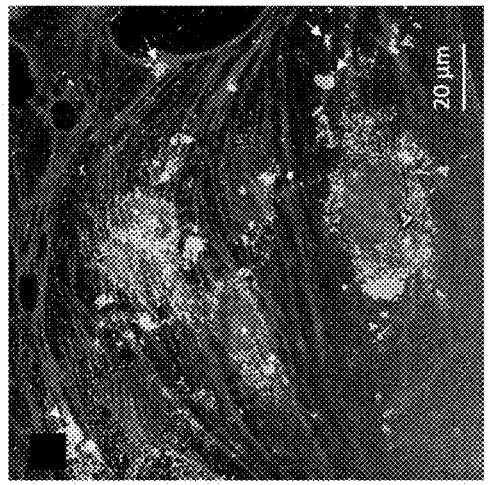
FIG. 38B is an image showing the uptake of hypoxic U251 GMs-derived exosomes by bEnd3 ECs.
Figure 38D:
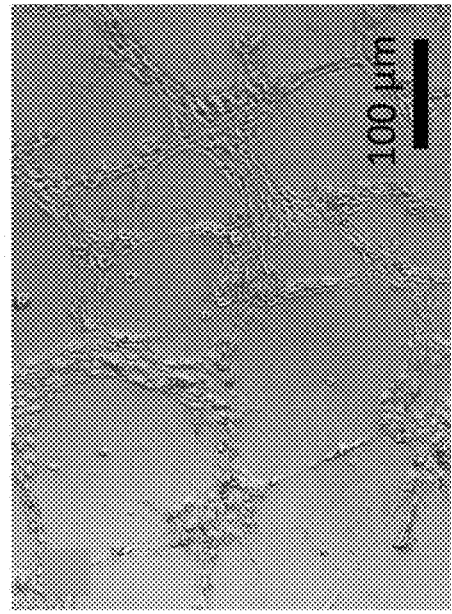
FIG. 38D is an image showing tube formation of bEnd3 ECs, as an angiogenesis assay, by the uptake hypoxia U251 GMs-derived exosomes.
Figure 38A:
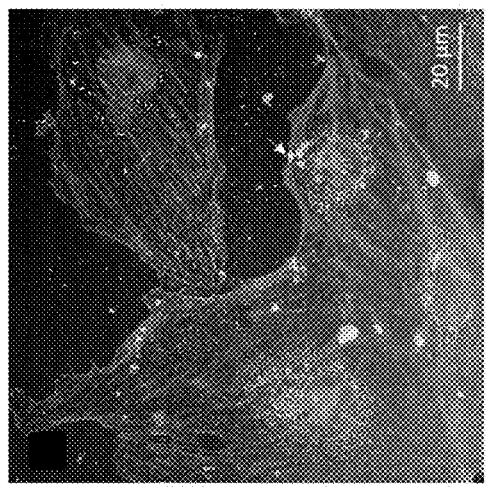
FIG. 38A is an image showing the uptake of normoxic U251 cells-derived exosomes by bEnd3 ECs.
Figure 38C:
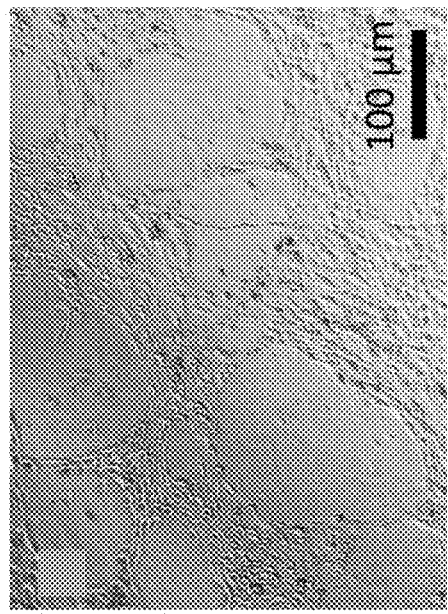
FIG. 38C is an image showing tube formation of bEnd3 ECs, as an angiogenesis assay, by the uptake normoxic U251 GMs-derived exosomes.

FIGS. 38A and 38B demonstrate the uptake of normoxic and hypoxic U251 GMs-derived exosomes by bEnd3 ECs. Blue: DAPI, Red: Phalloidin, Green: Exo-Green (hypoxic or normoxic U251 GMs-derived exosomes). FIGS. 38C and 38D show the representative images for tube formation of bEnd3 ECs, as an angiogenesis assay, by the uptake of normoxic and hypoxic U251 GMs-derived exosomes.

Recent reports demonstrated that exosomes could cross the blood-brain barriers (BBB) and blood-cerebrospinal fluid barriers (BCSFB), supporting a hypothesis that their components, including membrane proteins and microRNAs, could be utilized as surrogate biomarkers for the diagnosis and prognosis of brain disorders, including glioma, as liquid biopsies. Therefore, MCT1 and CD147 in GMs-derived exosomes could be potential biomarkers to monitor the metabolic adaptation and malignant progression of parent GMs.

As shown in the analysis of immunogold EM, MCT1 and CD147 were present mainly in the membrane of exosomes. Thus, sensitive label-free LSPR and AFM biosensors were employed to noninvasively detect exosomal MCT1 and CD147 with the SAM-AuNIs chip and silicon nitride cantilever tip, respectively, after their functionalization with anti-MCT1 antibody (AB) or anti-CD147 AB.

Example 13

Detection of Exosomal MCT1 and CD147

In order to detect exosomal MCT1 and CD147, LSPR biosensing was first performed with a functionalized SAM-AuNIs sensing chip.

The functionalized SAM-AuNIs sensing chip was prepared as follows. Dry SAM-AuNIs sensing chips in particular dry BK7 glass substrates with SAM-AuNIs, were sequentially rinsed with absolute ethanol (Sigma-Aldrich), incubated in 11-mercaptoundecanoic acid (MUA) solution (10 mM) for 30 minutes, and followed by rinsing off excess MUA molecules with absolute ethanol. Then, 2-(N-Morpholino) ethane sulfonic acid (MES) was prepared by mixing equal volume of activation chemicals 0.4M 1-ethyl-3-(3-dimethylaminopropyl) carbodiimide (ED C) and 0.15M N-Hydroxysuccinimide (NHS), then the freshly prepared MES solution was added to the SAM-AuNIs sensing chip for 20 minutes to activate the MUA carboxyl functional group.

Afterwards, 300 µl polyclonal primary antibodies in PBS (2 µg/ml; anti-MCT1 AB; dilution 1:100, and anti-CD147 antibody; dilution 1:200) were applied to the SAM-AuNIs sensing chip for 40 minutes for the immobilization of ABs. Excessive antibodies were rinsed away by PBS buffer, and non-specific sites were further blocked by treatment with 1M of ethanolamine.

The common-path interferometric sensing system and differential phase detection method were utilized to monitor the baseline phase responses during the functionalization process by adding each chemical and antibody to the chip, sequentially, and perform the label-free detection of exosomal proteins with the LSPR biosensor with the functionalized chip as described in Guangyu Qiu et al. Optical Letters Vol. 40, No. 9 May 2015 and Guangyu Qiu et al., Adv. Funct. Mater. 2018.

For the detection of exosomal MCT1 and CD147 via LSPR biosensing, phosphate-buffered saline (PBS) was employed as a basic running buffer. After rinsing SAM-AuNIs sensing chips with PBS, exosomes solutions (50 µg/ml PBS) were introduced over the antibody-functionalized surface of the sensing chip via using a peristaltic pump at constant rate of 30 µL/min. The SAM-AuNIs sensing chip was subsequently flushed again by PBS to check the binding affinity and remove the non-specific binding of exosomes to antibodies. LSPR experiments with exosomes in each experiment were performed three times independently.

For the assessment of detection sensitivity and specificity for exosomal MCT1 and CD147 with the biosensors, GMs-derived exosomes with their reduced or increased level were produced by genetic modifications such as OE or KD of MCT1 or CD147 in parent GMs.

Figure 41B:
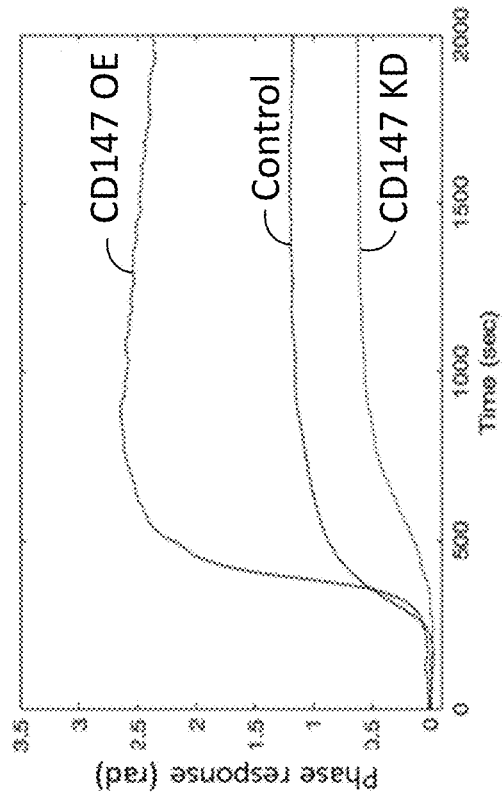
FIG. 41B shows the phase responses of the localized surface plasmon resonance (LSPR) biosensor with the functionalized SAM-AuNIs sensing chip with anti-CD147 antibody toward equal amount of daughter exosomes from parent U251 GMs with no-treatment, CD147 OE, and CD147 KD.
Figure 41A:
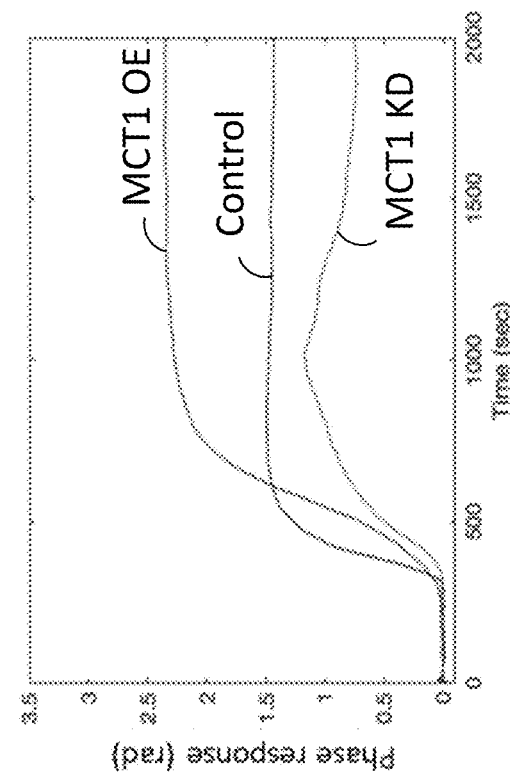
FIG. 41A is a plot showing the phase responses of the localized surface plasmon resonance (LSPR) biosensor with the functionalized SAM-AuNIs sensing chip with anti-MCT1 antibody toward equal amount of daughter exosomes from parent U251 GMs with no-treatment, MCT1 OE, and MCT1 KD.
Figures 42A, 42B:
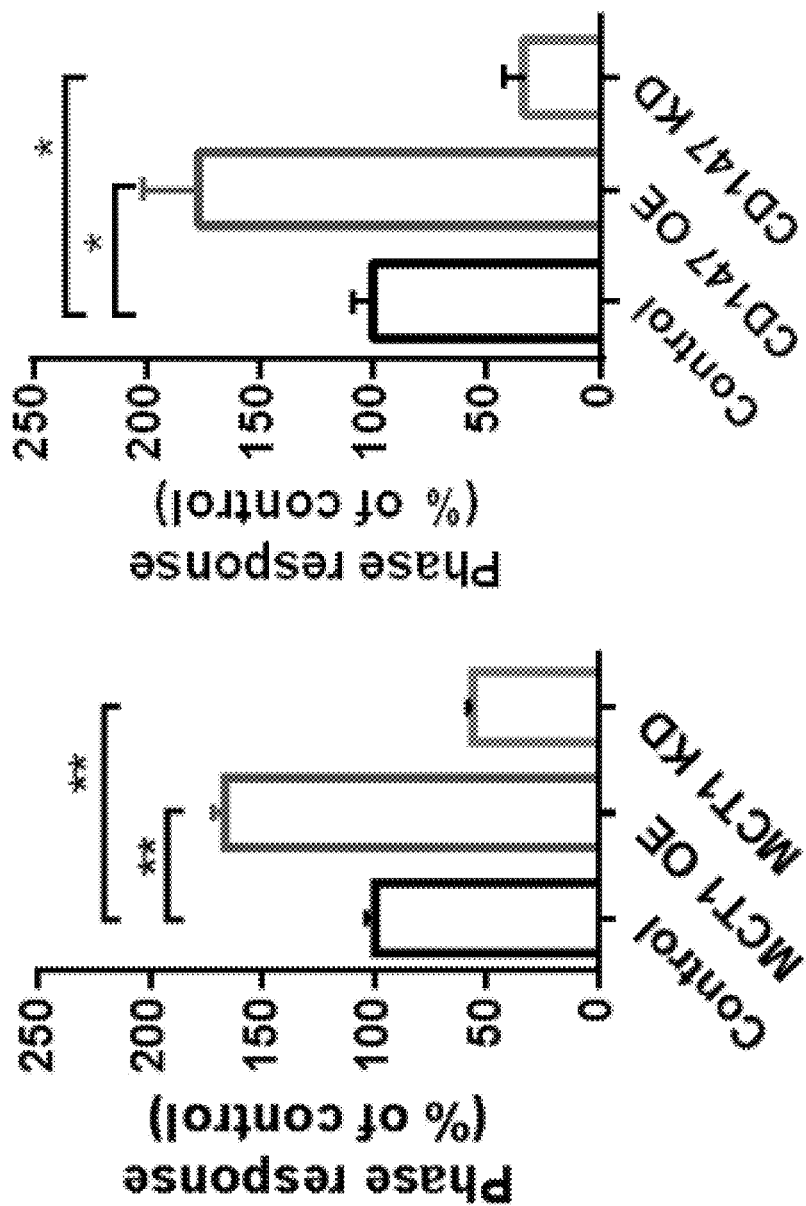
FIG. 42A is a graph showing the relative strength of localized surface plasmon resonance (LSPR) responses toward exosomal MCT1.
FIG. 42B is a graph showing the relative strength of localized surface plasmon resonance (LSPR) responses toward exosomal CD147.

FIGS. 41A and 41B show the phase responses of the LSPR biosensor with the functionalized SAM-AuNIs sensing chip with anti-MCT1 antibody or the anti-CD147 antibody toward equal amount of daughter exosomes (50 µg/ml) from parent U251 GMs with no-treatment (control), MCT1 OE, MCT1 KD, CD147 OE, and CD147 KD. The specificity of LSPR biosensing was demonstrated by the correlated LSPR phase response to the level of exosomal MCT1 and CD147. FIGS. 42A and 42B show the relative strength of LSPR responses (n=3) toward exosomal MCT1 and CD147. It is shown that, importantly, the non-invasive LSPR biosensor with the functionalized SAM-AuNIs sensing chip with anti-MCT1 antibody or anti-CD147 antibody was sensitive enough to quantitatively detect exosomal MCT1 or CD147.

FIGS. 43A and 43B show the baseline phase response of the LSPR biosensor with the functionalized SAM-AuNIs sensing chip with anti-MCT1 antibody or anti-CD147 antibody after sequential treatment with 11-MUA and EDC/NHS.

Figure 44B:
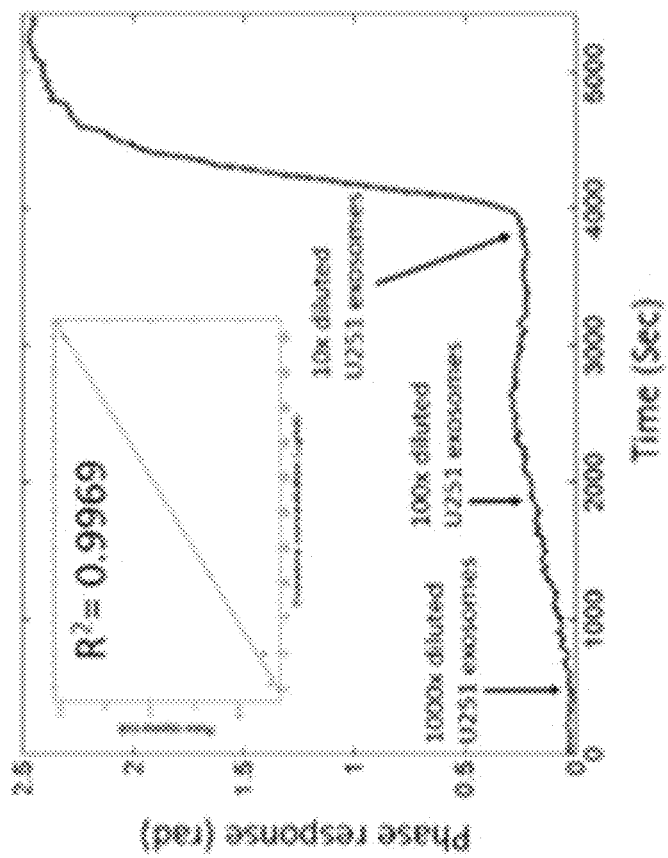
FIG. 44B is a graph showing the phase response of the localized surface plasmon resonance (LSPR) biosensor toward anti-CD147 antibody toward three different concentrations of U251 GMs-derived exosomes.
Figure 44A:
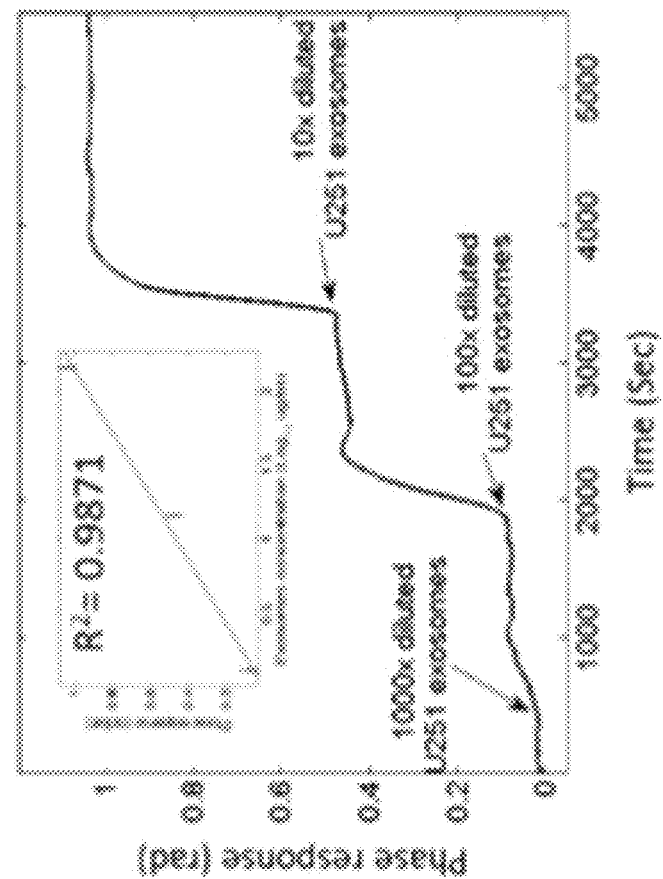
FIG. 44A is a graph showing the phase response of the localized surface plasmon resonance (LSPR) biosensor toward anti-MCT1 antibody toward three different concentrations of U251 GMs-derived exosomes.

FIGS. 44A and 44B show the phase response of the LSPR biosensor toward three different concentrations (serial dilution of 1300 µg/ml exosomes solution: 1000×, 100×, and 10×) of U251 GMs-derived exosomes. Standard curve fitting for phase responses toward anti-MCT1 antibody (R2=0.9871) or anti-CD147 antibody (R2=0.9969). It is demonstrated that, for example, the higher their level the bigger their LSPR response.

Figure 45B:
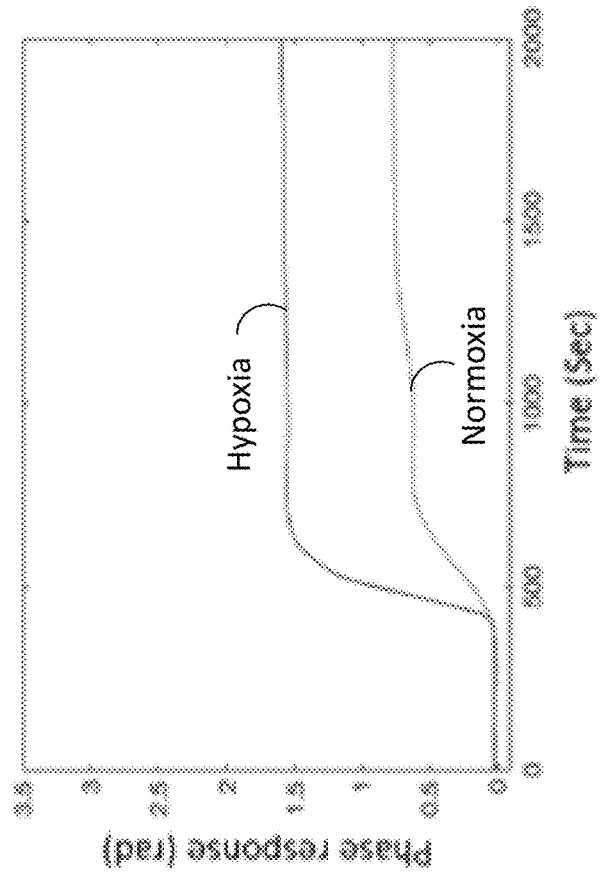
FIG. 45B is a graph showing the phase response of the localized surface plasmon resonance (LSPR) biosensor toward exosomal CD147 toward equal amount of normoxic and hypoxic GMs-derived exosomes.
Figure 45A:
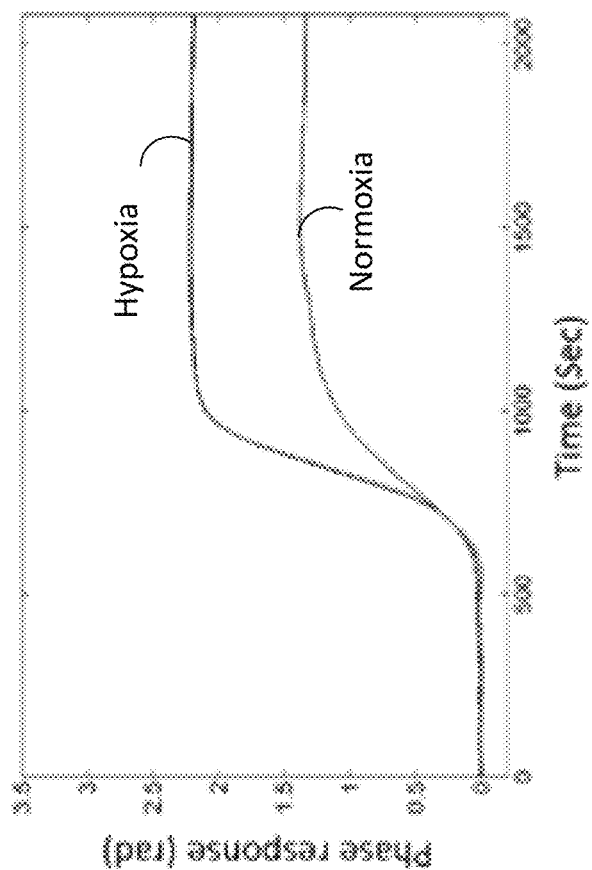
FIG. 45A is a graph showing the phase response of the localized surface plasmon resonance (LSPR) biosensor toward exosomal MCT1 toward equal amount of normoxic and hypoxic GMs-derived exosomes.
Figure 46B:
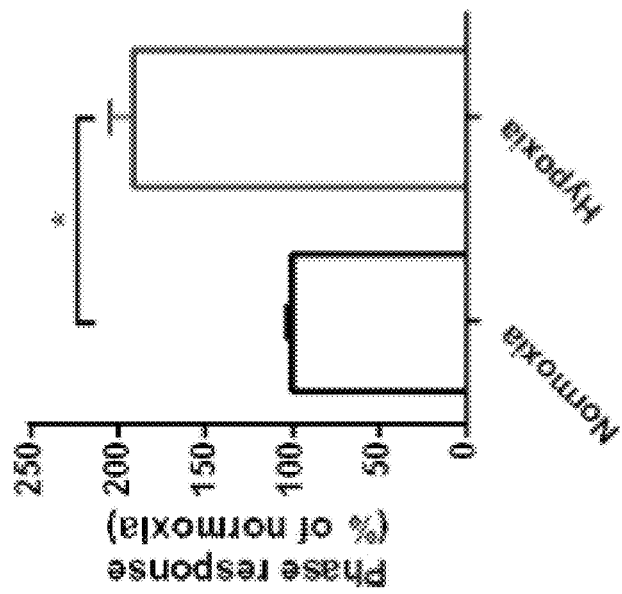
FIG. 46B is a graph showing the relative strength of localized surface plasmon resonance (LSPR) responses toward exosomal CD147 from normoxic or hypoxic GMs.
Figure 46A:
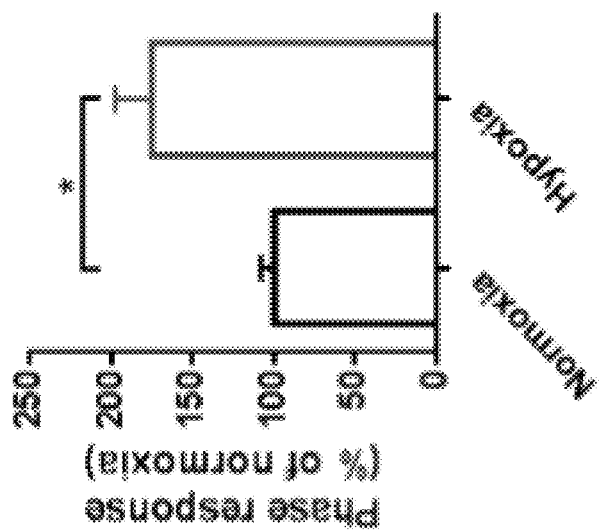
FIG. 46A is a graph showing the relative strength of localized surface plasmon resonance (LSPR) responses toward exosomal MCT1 from normoxic or hypoxic GMs.

FIGS. 45A and 45B show the phase response of the LSPR biosensor toward equal amount of normoxic and hypoxic GMs-derived exosomes (50 µg/ml). FIGS. 46A and 46B show the relative strength of LSPR responses toward exosomal MCT1 and CD147 from normoxic or hypoxic GMs (n=3). It is further determined that the LSPR biosensor precisely detected enhanced MCT1 or CD147 level in exosomes from hypoxic-GMs.

Next, the inventors conducted an atomic force microscopy (AFM) to detect MCT1 and CD147 in exosomes which were immobilized on SAM-AuNIs discs. Biosensing single molecular interaction between surface antigens of immobilized exosomes in SAM-AuNIs discs and anti-MCT1 or anti-CD147 antibodies functionalized in the sensing tip was conducted using BioScope Catalyst AFM (Bruker). The spring constant of AFM silicon nitride cantilever was calibrated to be 0.3756 N/m in the detection of exosomal proteins.

In order to capture exosomes, the surface of SAM-AuNIs sample discs of AFM was functionalized with anti-CD63 antibody as described above. 200 µl exosomes solutions (50 µg/ml PBS) were first added to the sample discs, incubated for 10 min, and replaced with 1 ml fresh PBS by mild decantation. Immunocaptured exosomes on the surface of the discs were further confirmed and analyzed by AFM scanning.

To determine exosomal MCT1 and CD147 levels by the measurement of intermolecular force between antigens and ABs, the silver nitride AFM tip (ScanAsyst-Fluid, TELTEC semiconductor pacific limited) was functionalized with either anti-MCT1 antibody or anti-CD147 antibody. In brief, primary antibodies (anti-MCT1 AB; dilution 1:100, and anti-CD147 AB; dilution 1:200) were covalently attached to the $Si_3N_4$ tip of AFM via thiol ester linkage (Bruker). The probe tip was washed with PBS, incubated in blocking solution (1% BSA-PBS) for 1 hr, and followed by washing with PBS.

All measurements of exosomal proteins via using AFM were recorded in PBS. Separation forces between MCT1 or CD147 in exosomes on SAM-AuNIs discs and anti-MCT1 or anti-CD147 antibodies on the sensing tips were measured by AFM ramp mode. Exosomal MCT1 and CD147 levels were determined and analyzed by the maximum peak of the AFM force-distance curve. Biophysical properties, including roughness, Young's modulus, and adhesion force, were recorded for exosomes captured on SAM-AuNIs discs by single ramping mode with a spring constant of 0.3801 N/m using a bare AFM sensing tip. A bare SAM-AuNIs sample discs was used as a control in the experiment. Each AFM force curve was obtained by at least three independent experiments.

Figure 47B:
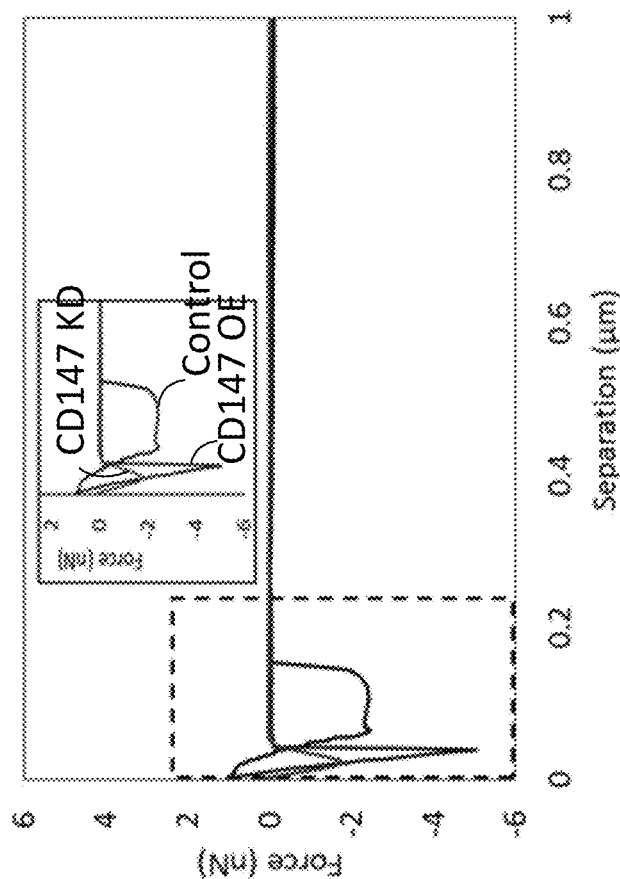
FIG. 47A shows the separation force responses of the atomic force microscopy (AFM) biosensor with the functionalized silicon nitride tip with anti-MCT1 antibody toward equal amount of daughter exosomes from parent U251 GMs with no-treatment, MCT1 OE, and MCT1 KD.
Figure 47A:
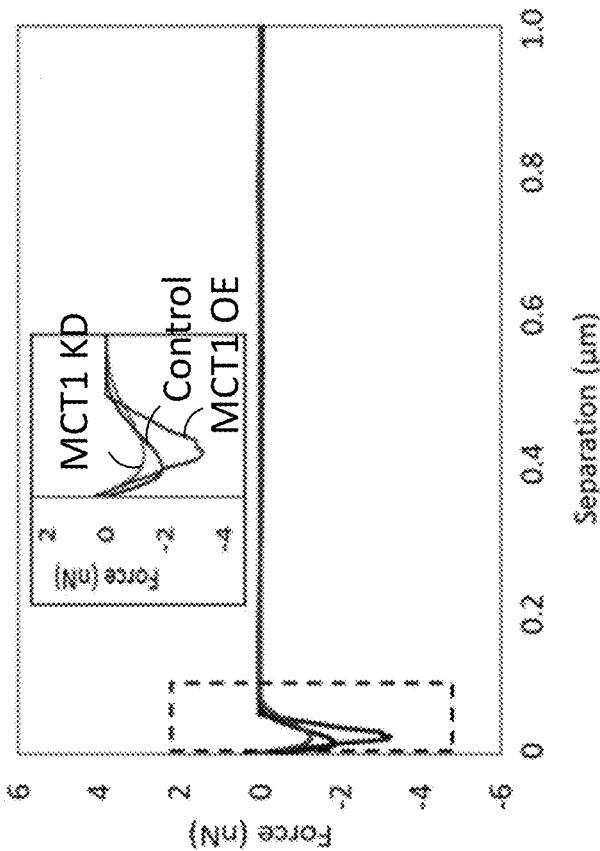
Figures 48A, 48B:
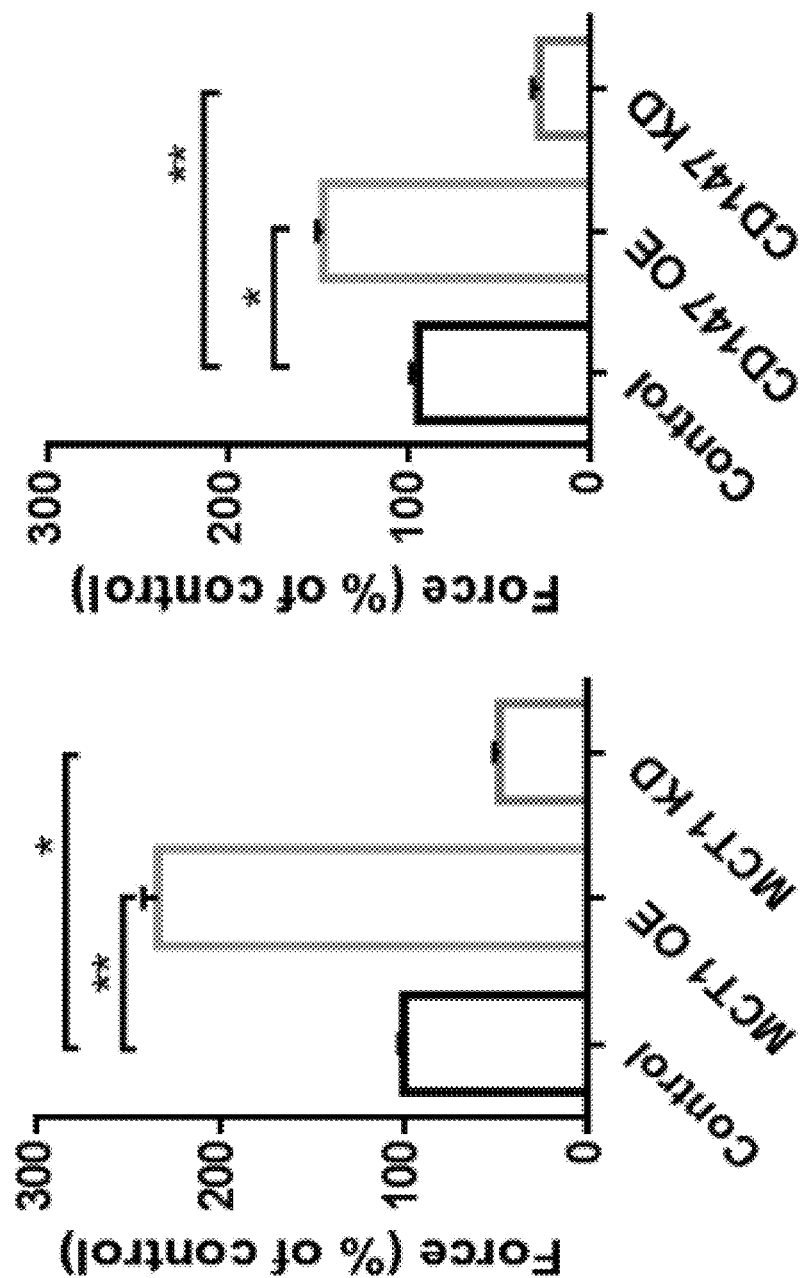

Exosomal MCT1 and CD147 were accurately detected by a high-resolution AFM biosensor. FIGS. 47A and 47B show the separation force responses of the AFM biosensor with the functionalized silicon nitride tip with anti-MCT1 antibody or the anti-CD147 antibody toward equal amount of daughter exosomes (50 µg/ml) from parent U251 cells with no-treatment (control), MCT1 OE, MCT1 KD, CD147 OE, and CD147 KD. FIGS. 48A and 48B show the relative strength of AFM forces (n=12) toward exosomal MCT1 and CD147. It is shown that a high degree of sensitivity and specificity of new AFM biosensing was established and validated via using MCT1 or CD147 deficient or enriched exosomes.

To quantitatively measure them, the spring constant of silicon nitride cantilever of the AFM biosensor was calibrated to be 0.3744 N/m. Importantly, it was first shown that the ScanAsyst-fluid mode of AFM imaging for exosomes captured on the functionalized SAM-AuNIs sample discs with anti-CD63 antibody could produce the great resolution of both two-dimensional (FIG. 49A) and three-dimensional (FIG. 49B) AFM topographic images of them, facilitating better analysis the biophysical properties of the cells.

Figure 50:
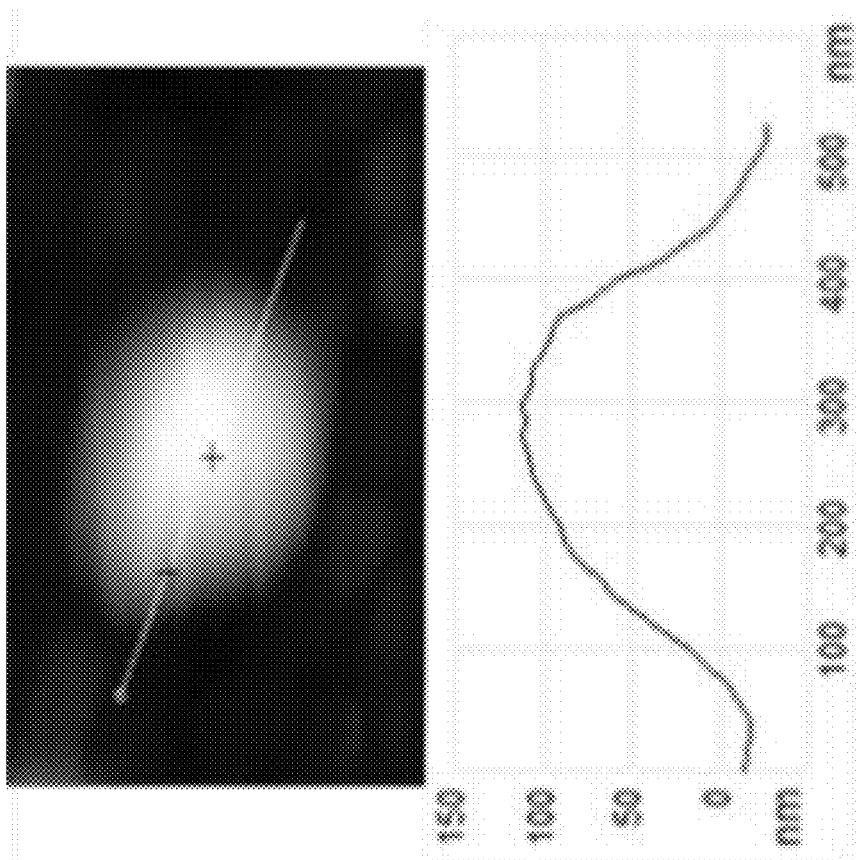

With reference to FIG. 49C and FIG. 50, height profile analysis in the three-dimensional AFM topographic image also clearly showed captured exosomes in the sample discs.

After the immobilization of exosomes on discs, the AFM biosensor was utilized to quantitatively detect exosomal MCT1 and CD147 by the functionalized cantilever tip with anti-MCT1 antibody or anti-CD147 antibody. This was the first "consecutive capture and sensing" method to detect exosomal surface proteins by AFM.

Figures 51A, 51B:
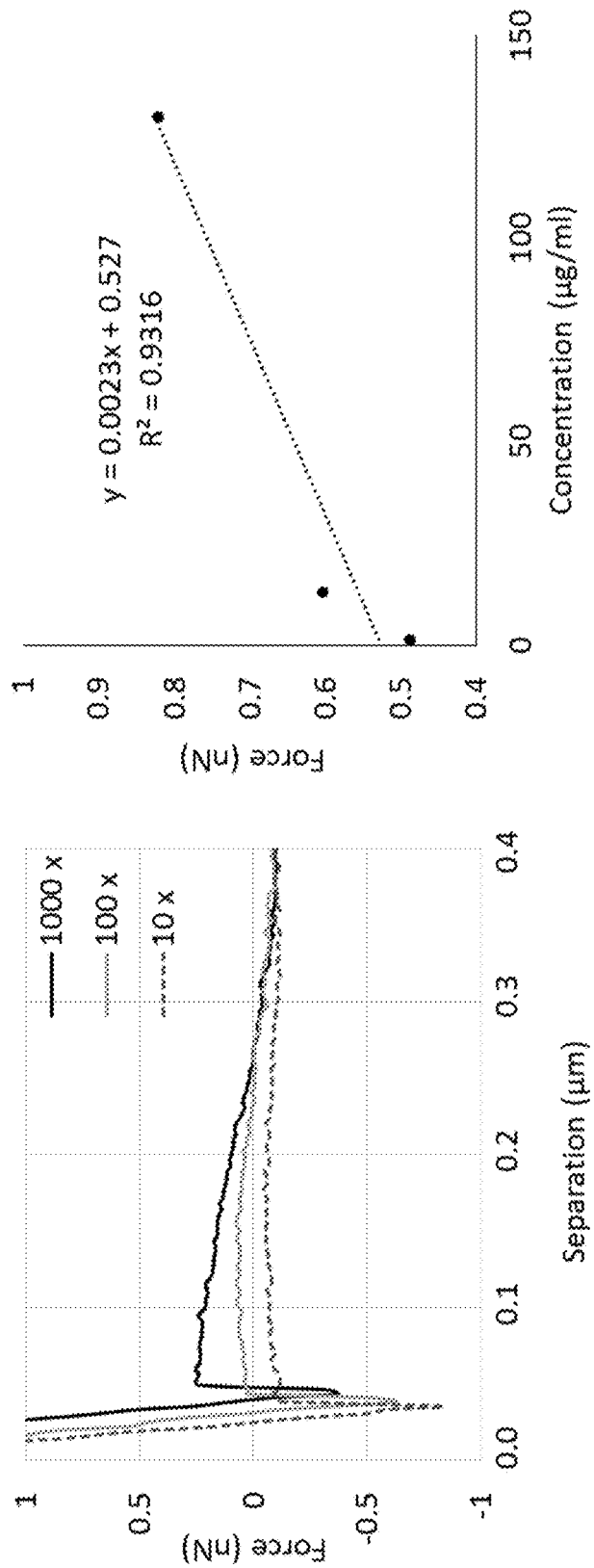

FIG. 51A shows the AFM separation curves between the functionalized sensing tip with anti-MCT1 antibody toward exosomes on the SAM-AuNIs sample discs, which were captured by anti-CD63AB, from three different concentrations of initial exosome solutions (Serial dilution: 1000×, 100×, and 10× of 500 μg/ml protein concentration) from U251 cells. FIG. 51B shows the correlation curve between exosome concentration and the strength of AFM forces toward exosomal MCT1 (for MCT1; $R2=0.9316$ and for CD147; $R2=0.8228$).

Figures 52A, 52B:
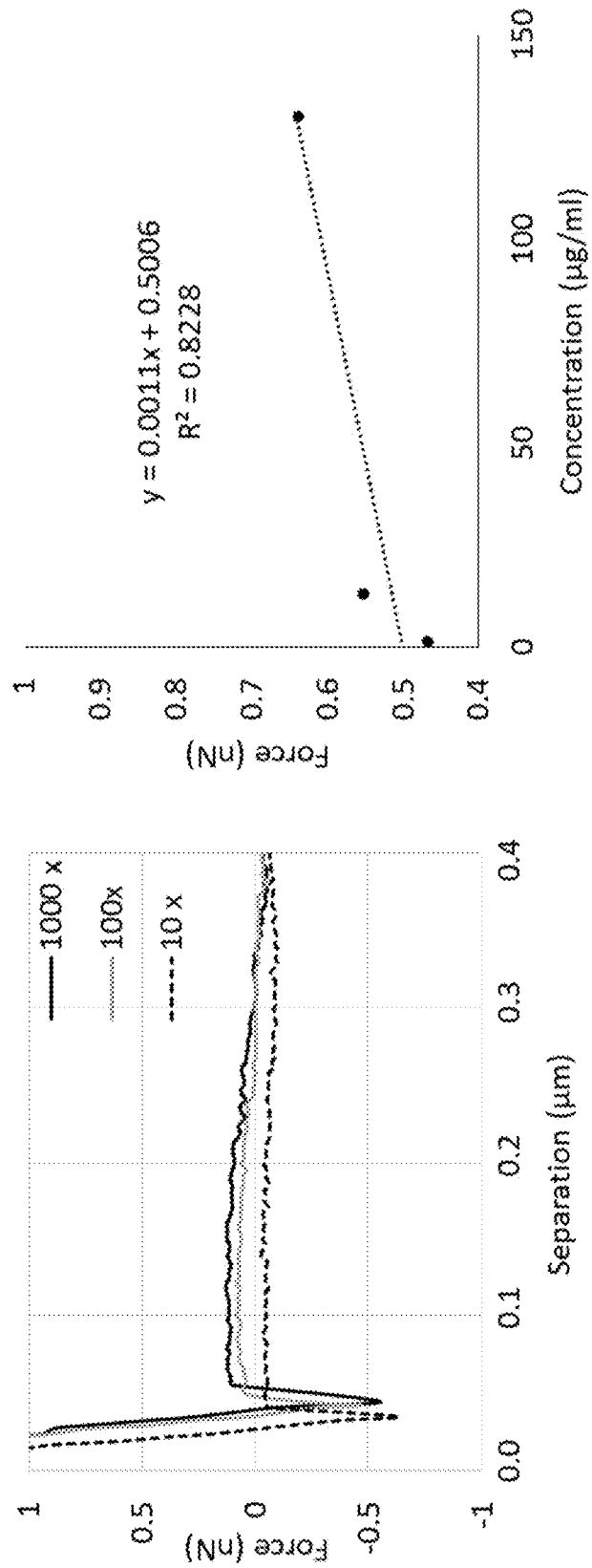

FIG. 52A shows the AFM separation curves between the functionalized sensing tip with anti-CD147 antibody toward exosomes on the SAM-AuNIs sample discs, which were captured by anti-CD63 antibody, from three different concentrations of initial exosome solutions (Serial dilution: 1000×, 100×, and 10× of 500 μg/ml protein concentration) from U251 cells. FIG. 52B shows the correlation curve between exosome concentration and the strength of AFM forces toward exosomal CD147, respectively (for MCT1; $R2=0.9316$ and for CD147; $R2=0.8228$).

FIGS. 53A and 53B show the separation force responses of the AFM biosensor with the functionalized cantilever sensing tip with anti-MCT1 AB, or anti-CD147 antibody toward equal amount (50 μg/ml) of normoxic and hypoxic GMs-derived exosomes captured on the SAM-AuNIs sample discs.

FIGS. 54A and 54B show the relative strength of AFM separation force responses toward exosomal MCT1 and CD147 from normoxic or hypoxic GMs (n=12). All data were shown as the mean±SEM. Significance level: **$P<0.01$, *$P<0.05$, hypoxia vs. normoxia.

It is demonstrated that the AFM biosensor precisely detected enhanced MCT1 or CD147 level in exosomes from hypoxic GMs.

Overall, with reference to FIGS. 55A and 55B, a strong positive correlation between the level of cellular MCT1 and CD147 and the response strength of LSPR (for MCT1; $R2=0.9247$ and CD147; $R2=0.9654$) and AFM (for MCT1; $R2=0.9996$ and CD147; $R2=0.9952$) for exosomal MCT1 and CD147 was observed, supporting the potential application of the combination of non-invasive LSPR and AFM-based detection for exosomal MCT1 and CD147 to monitor GMs' glycolytic metabolism associated with their malignant progression. The correlation analysis was performed based on the data obtained from FIGS. 41A, 41B, 47A and 47B. All data were shown as the mean±SEM. Significance level: **$P<0.01$, *$P<0.05$, MCT1 OE- and MCT1 KD- group vs. control. CD147 OE- and CD147 KD- group vs. control.

Example 13 demonstrates that exosomal MCT1 and CD147 are precisely detected by label-free LSPR and AFM biosensors. The combined use of LSPR and AFM biosensors allows a precise and accurate detection of the level of MCT1 and CD147 proteins in a sample, and allows non-invasive detection. The sample may be subjected to further analysis if needed.

Example 14

Detection of MCT1 and CD147 in Mouse Model of Glioma

MRI scan has been used as a major diagnostic method for glioma as well as in vivo glioma study. However, there is still a demand for new techniques for detecting molecular and metabolic signatures of glioma at its early stage for precise diagnosis. The method of present invention which is non-invasive liquid biopsy as described in Example 13 was used to determine the metabolic biomarkers of glioma in a mouse model.

Particularly, exosomal MCT1 and CD147 in blood serum were investigated in the course of glioma formation via using label-free LSPR and AFM biosensors. To begin with, an in vivo mouse model of glioma was established by the intracranial implantation of U251 cells or U87 cells in immuno-deficient mice.

In the course of glioma formation, MRI scan for each mouse was conducted and, consecutively, blood from the mouse was obtained for the isolation of serum-derived exosomes. Glioma formation was identified by MRI scan at approximately 10 days after the implantation of U251 cells and U87 cells into the brain (with a size range of 0.7-1.1 $mm^3$). FIGS. 56A-56C show the MRI images for the brain of sham-operated mice, U251 and U87 mouse model of glioma.

Characterization of isolated serum-derived exosomes from each mouse was conducted by NTA, TEM, and Immunogold EM. As shown in FIGS. 57A-57C, NTA demonstrated that number of serum-derived exosomes from a mouse model of glioma was significantly higher, indicating the systemic impact of glioma formation in the body. As shown in FIGS. 58A-58C, TEM results showed the heterogeneous morphology and size of serum-derived exosomes. As shown in FIGS. 59A-59F, immunogold EM revealed higher number of MCT1 and CD147 in serum-derived exosomes from a mouse model of glioma as compared to those of wild type mice, although those exosomes might be originated by various cell types in the body.

To detect the level of MCT1 and CD147 levels in the exosomes solutions, LSPR biosensing was first conducted, in particular equal amount of exosomes solutions (50 μg/ml) for each experiment were introduced into or applied on the SAM-AuNIs sensing chip at a constant rate of 30 μL/min. Then, AFM biosensing was conducted. Equal amount of exosomes solutions (50 μg/ml) for each experiment were introduced into the SAM-AuNIs sample discs, incubated for 10 min, slowly removed excess exosomes on sample discs with PBS before carrying out the detection in PBS.

With reference to FIGS. 60A-61B, LSPR and AFM responses toward exosomal MCT1 and CD147 in serum-derived exosomes from a mouse model of glioma was much bigger as compared to those from control mice. These data strongly suggested that, together with MRI images, label-free sensitive detection of exosomal MCT1 and CD147 in serum-derived exosomes could be supportive for the better diagnosis and prognosis of glioma.

Example 14 demonstrates that LSPR and AFM biosensors noninvasively detect MCT1 and CD147 in the blood serum-derived exosomes from a mouse model of glioma.

Accordingly, the present invention provides a method to detect the presence, absence and/or the relative amount of a target exosomal protein in a biological sample particularly a serum sample in a non-invasive approach. The method utilizes LSPR and AFM technologies with two specifically designed biosensors including functionalized LSPR and AFM substrates/chips for facilitating the detection. The biosensors facilitate a precise detection of exosomal proteins such as MCT1 protein and CD147 protein in the sample which in turn provides a feasible approach in glioma diagnosis. The method herein is suitable for monitoring the pathological progress of tumor or cancer, as well as for detection of a disease at early stage. The biosensors herein are applicable to be manufactured or sold in separate kits for performing the method as described herein.

The invention claimed is:

1. A method of detecting whether or not one or more exosomal proteins are present in a biological fluid sample to indicate the presence, or absence, or pathological progression of glioma or malignant glioma, the method combining localized surface plasmon resonance (LSPR) and atomic force microscopy (AFM) and comprising the steps of:
    obtaining a first result by localized surface plasmon resonance (LSPR); and obtaining a second result by atomic force microscopy (AFM) and using the second result to confirm the first result;
    the first result is obtained by step
    a) introducing, from the biological fluid sample, exosomes including at least one exosomal protein to at least a part of a first sensor having a self-assembly gold nano-islands (SAM AuNIs) functionalized with a first antibody that is capable of binding with the at least one exosomal protein to form a first sensor with immobilized exosomal proteins; measuring the LSPR's induced strength of phase response of the first sensor with immobilized exosomal proteins to generate the first result; and
    the second result is obtained by step
    b) introducing the biological fluid sample or portion of the biological fluid sample to a second sensor having self-assembly gold nano-islands (SAM AuNIs) functionalized with a anti-CD63 antibody to capture the exosomes from the biological fluid sample to form a second sensor with immobilized exosomes for AFM analysis;
    measuring separation force response of the second sensor with immobilized exosomes via atomic force microscopy (AFM) with a probe functionalized with the first antibody to generate the second result, wherein the second result further includes a two-dimensional or three-dimensional topographic image generated on the basis of the separation force response that facilitates studying cellular biophysical properties of the biological fluid sample, thereby enabling confirmation of the first result;
    wherein the at least one exosomal protein is selected from the group consisting of MCT1 protein, CD147 protein, a fragment thereof, and a combination thereof; and the first antibody is selected from the group consisting of anti-MCT1 antibody, anti-CD147 antibody and a combination thereof.

2. The method of claim 1, wherein the biological fluid sample is a serum sample comprising exosomes.

3. The method of claim 1, wherein the measuring of the LSPR's induced strength of phase response is carried out by a common-path interferometric sensing system and differential phase detection.

4. A kit designed for detecting whether or not at least one exosomal protein selected from the group consisting of MCT1 protein, CD147 protein, a fragment thereof, and a combination thereof, is present in a biological fluid sample to indicate the presence, or absence, or pathological progression of glioma or malignant glioma by way of combining localized surface plasmon resonance (LSPR) and atomic force microscopy (AFM), said kit comprising:
    a first sensor having a self-assembly gold nano-islands (SAM AuNIs) immobilized with a first antibody that is capable of binding with the exosomal protein present in the biological fluid sample to form a first sensor with immobilized exosomal proteins, wherein when subjected to an optical radiation in a certain spectral range the first sensor with immobilized exosomal proteins produces a first result including LSPR's induced strength of phase response; and
    a second sensor having a self-assembly gold nano-islands (SAM AuNIs) immobilized with a anti-CD63 antibody which captures exosomes in the biological fluid sample to form a second sensor with immobilized exosomes for AFM analysis with a probe functionalized with the first antibody, wherein a second result including separation force response of the second sensor with immobilized exosomes is obtainable via the AFM analysis, and the second result is used to confirm the first result; wherein the second result further includes a two-dimensional or three-dimensional topographic image generated on the basis of the separation force response that facilitates studying cellular biophysical properties of the biological fluid sample, thereby enabling confirmation of the first result; and
    wherein the first antibody is selected from the group consisting of anti-MCT1 antibody, anti-CD147 antibody and a combination thereof.

5. The kit of claim 4 comprising an activation agent for activating the first sensor, and a mixture containing an antibody targeting the at least one exosomal protein.

6. The kit of claim 4, wherein the probe has a cantilever tip that is made of silver nitride or silicon nitride for atomic force microscopy and functionalized with anti-MCT1 antibody or anti-CD147 antibody.

7. The method of claim 1, wherein the biological fluid sample comprises an exosome from the blood of a glioma mouse blood model, and wherein the method is for tracking metabolic reprogramming and malignant progression of cancer.

8. The method of claim 7, wherein the cancer is glioma.

9. The method of claim 1, wherein the probe includes a cantilever tip that is made of silicon nitride or silver nitride, and is functionalized with the first antibody.

* * * * *